(12) United States Patent
Blake et al.

(10) Patent No.: US 7,479,489 B2
(45) Date of Patent: Jan. 20, 2009

(54) HETEROCYCLIC ANTIVIRAL COMPOUNDS

(75) Inventors: James F. Blake, Longmont, CO (US); Jay Bradford Fell, Longmont, CO (US); John P. Fischer, Longmont, CO (US); Robert Than Hendricks, San Carlos, CA (US); John E. Robinson, Commerce City, CO (US); Stacey Renee Spencer, Lyons, CO (US); Peter J. Stengel, Longmont, CO (US)

(73) Assignee: Roche Palo Alto LLC, Palo Alto, CA (US)

( * ) Notice: Subject to any disclaimer, the term of this patent is extended or adjusted under 35 U.S.C. 154(b) by 467 days.

(21) Appl. No.: 11/208,962

(22) Filed: Aug. 22, 2005

(65) Prior Publication Data

US 2006/0040927 A1 Feb. 23, 2006

Related U.S. Application Data

(60) Provisional application No. 60/677,710, filed on May 4, 2005, provisional application No. 60/603,771, filed on Aug. 23, 2004.

(51) Int. Cl.
*C07D 417/02* (2006.01)
*A61K 31/5415* (2006.01)

(52) U.S. Cl. .................................... 514/224.2; 544/52
(58) Field of Classification Search .................. 544/52; 514/224.2
See application file for complete search history.

(56) References Cited

U.S. PATENT DOCUMENTS

| 5,550,143 | A | 8/1996 | Brion et al. |
| 5,654,323 | A | 8/1997 | Brion et al. |
| 2004/0087577 | A1 | 5/2004 | Pratt et al. |
| 2004/0097492 | A1 | 5/2004 | Pratt et al. |
| 2004/0162285 | A1 | 8/2004 | Pratt et al. |
| 2004/0167123 | A1 | 8/2004 | Pratt et al. |
| 2005/0075331 | A1 | 4/2005 | Pratt et al. |

FOREIGN PATENT DOCUMENTS

| WO | WO 00/55147 | 9/2000 |
| WO | WO 01/01933 A2 | 1/2001 |
| WO | WO 01/85172 A1 | 11/2001 |
| WO | WO 02/098424 A1 | 12/2002 |
| WO | WO 03/037262 A2 | 5/2003 |
| WO | WO 03/059356 A2 | 7/2003 |
| WO | WO 03/099801 A1 | 12/2003 |
| WO | WO 2004/041818 A1 | 5/2004 |
| WO | WO 2004/052312 A2 | 6/2004 |
| WO | WO 2004/052313 A2 | 6/2004 |
| WO | WO 2004/058150 A2 | 7/2004 |
| WO | WO 2005/019191 A2 | 3/2005 |

OTHER PUBLICATIONS

T.T. Nguyen et al., Resistance profile of a hepatitis C Virus RNA-dependent RNA polymerase benzothiadiazine inhibitor *Antimicrob. Agents and Chemother*. 2003 47(11)3525-30.
B. Gu et al., "Arresting Initiation of Hepatitis C. Virus RNA synthesis using heterocyclic derivatives" *J. Biol. Chem.* 2003 278(19): 16602-16607.
D. Dhanak et al., "Identification and Biological Characterization of Heterocyclic Inhibitors of HCV RNA-dependent RNA polymerase" *J. Biol. Chem.* 2002 277(41):38322-38327.

*Primary Examiner*—Kahsay T Habte
(74) *Attorney, Agent, or Firm*—Brian L. Buckwalter

(57) ABSTRACT

Compounds having the formula I wherein A, m and $R^1$ are herein defined are Hepatitis C virus polymerase inhibitors. Also disclosed are compositions and methods for treating diseases mediated by HCV and for inhibiting hepatitis replication. Also disclosed are processes for making the compounds and synthetic intermediates used in the process (I)

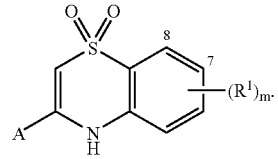

41 Claims, No Drawings

HETEROCYCLIC ANTIVIRAL COMPOUNDS

CROSS RFERENCE TO RELATED APPLICATIONS

This application claims the benefit of priority to U.S. Ser. No. 60/603,771 filed Aug. 23, 2004 and to U.S. Ser. No. 60/677,710 filed May 4, 2005 which are hereby incorporated by reference in their entirety.

FIELD OF THE INVENTION

The present invention provides non-nucleoside compounds and certain derivatives thereof which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

The invention relates to non-nucleoside derivatives as inhibitors of HCV replicon RNA replication. In particular, the invention is concerned with the use of heterocyclic compounds as inhibitors of subgenomic HCV RNA replication and pharmaceutical compositions containing such compounds.

Hepatitis C virus is the leading cause of chronic liver disease throughout the world. (Boyer, N. et al. *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae: The viruses and their replication*. In: *Fields Virology*, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukl, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown. It is believed that most of the non-structural proteins encoded by the HCV RNA genome are involved in RNA replication Currently there are a limited number of approved therapies are currently available for the treatment of HCV infection. New and existing therapeutic approaches to treating HCV and inhibition of HCV NS5B polymerase have been reviewed: R. G. Gish, *Sem. Liver. Dis.,* 1999 19:5; Di Besceglie, A. M. and Bacon, B. R., Scientific American, October: 1999 80-85; G. Lake-Bakaar, *Current and Future Therapy for Chronic Hepatitis C Virus Liver Disease, Curr. Drug Targ. Infect Dis.* 2003 3(3):247-253; P. Hoffmann et al., *Recent patents on experimental therapy for hepatitis C virus infection* (1999-2002), *Exp. Opin. Ther. Patents* 2003 13(11):1707-1723; M. P. Walker et al., *Promising Candidates for the treatment of chronic hepatitis C, Exp. Opin. investing. Drugs* 2003 12(8): 1269-1280; S.-L. Tan et al., *Hepatitis C Therapeutics: Current Status and Emerging Strategies, Nature Rev. Drug Discov.* 2002 1:867-881; J. Z. Wu and Z. Hong, *Targeting NS5B RNA-Dependent RNA Polymerase for Anti-HCV Chemotherapy, Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% or patients, it does not lower serum levels of HCV-RNA. Ribavirin also exhibits significant toxicity and is known to induce anemia. Viramidine is a ribavirin prodrug converted to in hepatocytes.

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGA-SYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release,* 2001 72:217-224).

Combination therapy of HCV with ribavirin and interferon-α currently is the optimal therapy for HCV. Combining ribavirin and PEG-IFN (infra) results in a sustained viral response in 54-56% of patients. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up be the cell and converted in vivo to a triphosphate to compete for the polymerase nucleotide binding site. This conversion to the triphosphate is commonly mediated by cellular kinases which imparts additional structural limitations on any nucleoside. In addition this limits the direct evaluation of nucleosides as inhibitors of HCV replication to cell-based assays.

Non-nucleoside allosteric inhibitors of HIV reverse transcriptase have proven effective therapeutics alone and in combination with nucleoside inhibitors and with protease inhibitors. Several classes of non-nucleoside HCV NS5B inhibitors have been described and are currently at various stages of development including: benzimidazoles, (H. Hashimoto et al. WO 01/47833, H. Hashimoto et al. WO 03/000254, P. L. Beaulieu et al. WO 03/020240 A-2; P. L. Beaulieu et al. U.S. Pat. No. 6,448,281 B1; P. L. Beaulieu et al. WO 03/007945 A-1); indoles, (P. L. Beaulieu et al. WO 03/0010141 A-2); benzothiadiazines, e.g., 1, (D. Dhanak et al. WO 01/85172 A-1; D. Dhanak et al. WO 03/037262 A-2; K. J. Duffy et al. WO03/099801 A-1, D. Chai et al. WO 2004052312, D. Chai et al. WO2004052313, D. Chai et al. WO02/098424, J. K. Pratt et al. WO 2004/041818 A-1; J. K. Pratt et al. WO 2004/087577 A-1), thiophenes, e.g., 2, (C. K. Chan et al. WO 02/100851 A-2); benzothiophenes (D. C. Young and T. R. Bailey WO 00/18231); P3-ketopyruvates (S. Attamura et al. U.S. Pat. No. 6,492,423 B1, A. Attamura et al. WO 00/06529); pyrimidines (C. Gardelli et al. WO 02/06246 A-1); pyrimidinediones (T. R. Bailey and D. C. Young WO 00/13708); triazines (K.-H. Chung et al. WO 02/079187 A-1); rhodanine derivatives (T. R. Bailey and D. C. Young WO 00/10573, J. C. Jean et al. WO 01/77091 A-2); 2,4-dioxopyrans (R. A. Love et al. EP 256628 A-2); phenylalanine derivatives (M. Wang et al. *J. Biol. Chem.* 2003 278:2489-2495).

SUMMARY OF THE INVENTION

The present invention is directed toward novel heterocyclic compounds that inhibit HCV polymerase, methods of treating a disorder mediated by HCV with said compounds and pharmaceutical compositions containing said compound which compound possesses a structure according to formula I

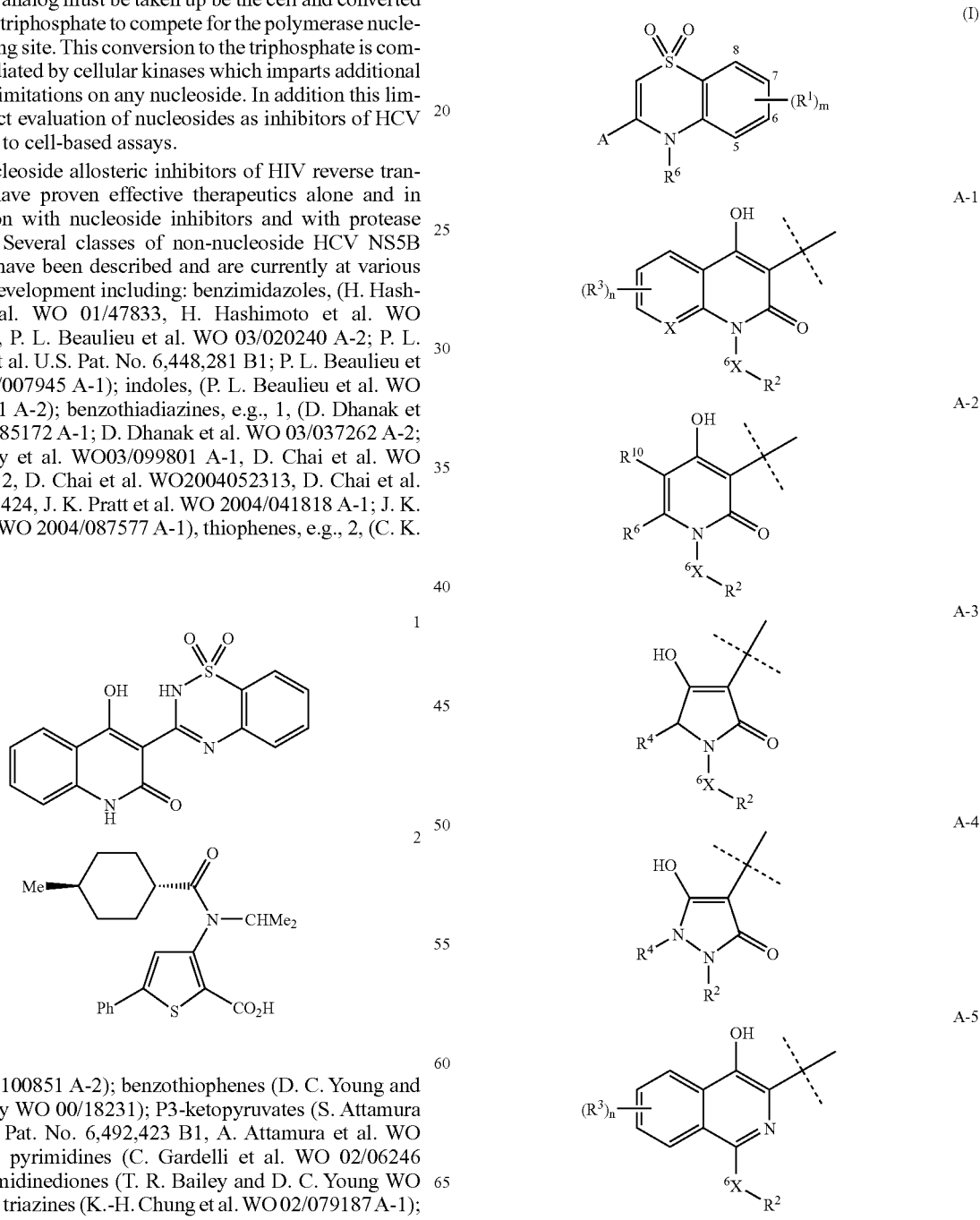

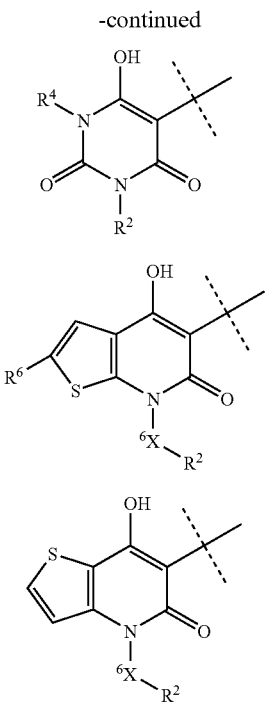

wherein:
A is selected from the grouping consisting of A-1, A-2, A-3, A-4, A-5, A-6, A-7 and A-8;
X is CH or N;
$X^6$ is —O—, —$NR^6$— or $X^6$ is absent;
$R^1$ in each incidence is independently selected from the group consisting of $C_{1-6}$ alkyl, $C_{2-6}$ alkenyl, $C_{2-6}$ alkynyl, $C_{3-7}$ cycloalkyl, $C_{3-7}$ cycloalkyl-$C_{1-4}$ alkyl, $C_{1-6}$ alkoxy, optionally substituted phenyl, optionally substituted phenyl-$C_{1-6}$ alkyl, $C_{1-6}$ hydroxyalkyl, $C_{1-3}$ alkoxy-$C_{1-6}$ alkyl, optionally substituted phenoxy, optionally substituted phenyl-$C_{1-3}$ alkoxy, $C_{1-6}$ heteroalkoxy, hydroxyl, halogen —$X^1(CH_2)_oCOR^5$, —$(CH_2)_oCOR^5$, —$X^1(CH_2)_oSO_2R^7$, —$(CH_2)_oSO_2R^7$, —$X^5C(=O)R^9$, —$NR^6SO_2R^7$, —$X^4(CH_2)_rNR^{a\prime}R^{b\prime}$, —$CO_2R^6$, $X^4NR^aR^b$, nitro, and cyano wherein said optionally substituted phenyl groups are substituted with one to three substituents independently selected from the group consisting of $C_{1-3}$ alkyl, $C_{2-4}$ alkenyl, $C_{2-4}$ alkynyl, $C_{1-3}$ alkoxy, phenoxy, $C_{1-3}$ haloalkyl, hydroxy, halogen, $NR^aR^b$, cyano and nitro;
$R^2$ is independently selected from the group consisting of $C_{1-6}$ alkyl, $C_{3-6}$ alkenyl, $C_{3-6}$ alkynyl, pyridinylmethyl, imidazolinylmethyl, $C_{3-7}$ cycloalkyl, $C_{3-7}$ cycloalkyl-$C_{1-3}$ alkyl, $C_{1-6}$ heteroalkyl and phenyl-$C_{1-3}$ alkyl said phenyl optionally substituted with one to three substituents independently selected from the group consisting of $C_{1-3}$ alkyl, $C_{2-4}$ alkenyl, $C_{2-4}$ alkynyl, $C_{1-3}$ alkoxy, phenoxy, $C_{1-3}$ haloalkyl, hydroxy, halogen, $NR^aR^b$, cyano and nitro;
$R^3$ in each incidence is independently selected from the group consisting of $C_{1-16}$ alkyl, $C_{2-6}$ alkenyl, $C_{2-6}$ alkynyl, $C_{3-7}$ cycloalkyl, $C_{3-7}$ cycloalkyl-$C_{1-4}$alkyl, $C_{1-6}$ alkoxy, halogen, hydroxyl, —$NR^aR^b$, $C_{1-6}$ acylamino, —$NR^6SO_2R^7$, cyano and nitro;
$R^4$ is hydrogen, $C_{1-6}$ alkyl, $C_{3-7}$ cycloalkyl, $C_{3-7}$ cycloalkyl-$C_{1-4}$alkyl, $C_{1-6}$ heteroalkyl, phenyl or phenyl-$C_{1-4}$ alkyl said phenyl optionally substituted independently with one to three $R^3$ radicals;
$R^5$ is hydroxyl, alkoxy, —$NR^aR^b$, phenyl or $C_{1-6}$ heteroalkoxy;
$R^6$ is hydrogen or $C_{1-6}$ alkyl;
$R^7$ is $C_{1-6}$ alkyl, $C_{3-7}$ cycloalkyl, $C_{3-7}$ cycloalkyl-$C_{1-4}$ alkyl, —$NR^aR^b$, —$NR^6(CH_2)_p$-phenyl, —NHBoc, $C_{1-6}$ heteroalkyl, —$X^2(CH_2)_oCOR^5$, optionally substituted isoxazole, phenyl or phenyl-$C_{1-3}$ alkyl wherein said phenyl and said isoxazole are each optionally substituted independently with one to three $C_{1-3}$ alkyl, $C_{1-3}$ alkoxy, halogen, nitro or cyano;
$R^8$ is $R^6$ or $C_{1-6}$ acyl;
$R^9$ is $C_{1-6}$ alkyl, $C_{3-7}$ cycloalkyl, phenyl, $NR^aR^b$ or $OR^4$ wherein $R^4$ is not hydrogen and said phenyl is optionally substituted with one to three $R^3$ radicals;
$R^{10}$ is phenyl or pyridinyl said phenyl and said pyridinyl are optionally substituted with one to three substituents selected from the group consisting of $C_{1-3}$ alkyl, $C_{1-3}$ alkoxy, $C_{1-3}$ haloalkyl, halogen, $NR^aR^b$, cyano and nitro;
$R^a$ and $R^b$ are (i) independently hydrogen, $C_{1-6}$ alkyl or $C_{1-6}$ heteroalkyl, or (ii) taken together are $(CH_2)_q$, —$(CH_2)_2OC(=O)$— or $(CH_2)_2X^3(CH_2)_2$;
$R^{a\prime}$ and $R^{b\prime}$ independently are (i) hydrogen, $C_{1-6}$ alkyl or $C_{1-6}$ heteroalkyl, or (ii) $R^a$ is —$SO_2R^4$, —$SO_2NR^aR^b$ or —$COR^9$ and $R^b$ is hydrogen; or (iii) $R^{a\prime}$ and $R^{b\prime}$ taken together are $(CH_2)_q$ or $(CH_2)_2X^3(CH_2)_2$;
$X^1$ is O, $S(O)_p$, $C(=O)$ or $NR^6$;
$X^2$ is $NR^6$ or a bond;
$X^3$ is —O—, $C=O$ or $NR^8$;
$X^4$ is $X^1$ or a bond;
$X^5$ is $NR^6$ or O;
m and n are independently zero to three;
o and r are independently one to six;
p is zero to two;
q is four to seven; and, pharmaceutically acceptable salts thereof.

The present invention is further directed a methods for inhibiting HCV polymerase in cells infected by HCV.

DETAILED DESCRIPTION OF THE INVENTION

In one embodiment of the present invention there is provided a compound of formula I wherein A, X, $X^1$-$X^6$, $R^1$-$R^{10}$, $R^a$, $R^b$, $R^{a\prime}$, $R^{b\prime}$, m, n, o, p, q and r are as defined herein above.

In another embodiment of the present invention there is provided a compound of formula I wherein A is A-1, A-2, A-3 or A-4; X is N, CH, or $CR^3$; $X^6$ is absent; $R^1$ is selected in each incidence from the group consisting of $C_{1-6}$ alkyl, $C_{2-6}$ alkenyl, $C_{2-6}$ alkynyl, $C_{1-6}$ alkoxy, optionally substituted phenyl-$C_{1-6}$ alkyl, $C_{1-6}$ hydroxyalkyl, $C_{1-3}$ alkoxy-$C_{1-6}$ alkyl, optionally substituted phenoxy, optionally substituted phenyl-$C_{1-3}$ alkoxy, $C_{1-6}$ heteroalkoxy, hydroxyl, halogen —$X^1(CH_2)_o$ $COR^5$, —$NR^6SO_2R^7$, —$X^5C(=O)R^9$, —$X^4(CH_2)_rNR^aR^b$, —$CONR^aR^b$, nitro, and cyano wherein optionally substituted phenyl groups are substituted with one to three substituents independently selected from the group consisting of $C_{1-3}$ alkyl, $C_{1-3}$ alkoxy, $C_{1-3}$ haloalkyl, halogen, $NR^aR^b$, cyano and nitro; $R^2$ is $C_{1-6}$ alkyl, $C_{3-6}$ alkenyl, $C_{3-6}$ alkynyl, optionally substituted phenyl-$C_{1-3}$ alkyl, cycloalkyl, $C_{3-7}$ cycloalkyl-$C_{1-3}$ alkyl or $C_{1-6}$ heteroalkyl; $R^3$ is $C_{1-6}$ alkyl, $C_{2-6}$ alkenyl, $C_{2-6}$ alkynyl, $C_{1-6}$ alkoxy, halogen, hydroxyl, —$NR^aR^b$, $C_{1-6}$ acylamino, —$NR^6SO_2R^7$, cyano or nitro; $R^4$ is $C_{1-6}$ alkyl, $C_{3-7}$ cycloalkyl or phenyl optionally substituted independently with one to three $R^3$ radicals; $R^5$ is hydroxyl, alkoxy, amino, —$NR^aR^b$, or $C_{1-6}$ heteroalkoxy; $R^6$ is hydrogen or $C_{1-3}$ alkyl; $R^7$ is $C_{1-6}$ alkyl, —$NR^aR^b$, $C_{1-6}$ heteroalkyl, —$X^2$ $(CH_2)_oCOR^5$, aryl $C_{1-3}$ alkyl or phenyl said phenyl optionally substituted with one to three radicals independently selected in each incidence from $C_{1-3}$ alkyl, $C_{1-3}$ alkoxy, halogen, nitro or cyano; $R^8$ is $R^6$ or $C_{1-6}$ acyl; $R^9$ is $C_{1-6}$ alkyl, $NH_2$, $NR^6R^7$, OH or $OR^7$; $R^a$ and $R^b$ are (i) independently hydrogen, $C_{1-6}$ alkyl or $C_{1-6}$ heteroalkyl, or (ii) taken together are $(CH_2)_q$ or $(CH_2)_2X^3(CH_2)_2$; $X^1$ is O, $S(O)_p$ or $NR^6$; $X^2$ is $NR^6$ or a bond; $X^3$ is —O—, C=O or $NR^8$; $X^4$ is $X^1$ or a bond; $X^5$ is $NR^6$ or O; m and n are independently zero to three; o is one to six; p is zero to two; q is four to seven; r is zero to 6; and, pharmaceutically acceptable salts thereof.

In another embodiment of the present invention there is provided a compound of formula I wherein A is A-1-A-5 or A-7; $X^6$ is absent; $R^1$ in each incidence is independently selected in each incidence from the group consisting of halogen, nitro, cyano, hydroxyl, benzyloxy, $C_{1-3}$ alkoxy, amino, $C_{1-3}$ alkylamino, $C_{1-6}$ acylamino, $C_{1-6}$ alkylsulfonylamino, $C_{1-6}$ alkylsulfonyl-$C_{1-3}$ alkylamino-$C_{3-7}$ cycloalkylsulfonylamino, amino-$C_{1-3}$ alkyl, $C_{1-3}$ alkylamino-$C_{1-3}$ alkyl, phenylsulfonylamino, benzylsulfonylamino, 3,5-dimethyl-4-isoxazol-4-yl-sulfonyl-amino, —$OCH_2CONR^cR^d$ or $O(CH_2)_2CONR^cR^d$ wherein $R^c$ and $R^d$ are independently hydrogen or $C_{1-3}$ alkyl, —$OCH_2CO_2R^c$ wherein $R^c$ is as described above, —$NHCONR^cR^d$, —$NHCO_2$'Bu, or $NHSO_2NR^eR^f$ wherein $R^e$ and $R^f$ are independently hydrogen, $C_{1-3}$ alkyl or $CO_2$-t-Boc, or $R^e$ and $R^f$ together are $(CH_2)_4$ and $(CH_2)_2OC(=O)$; $R^2$ is $C_{1-6}$ alkyl, $C_{1-3}$ alkyl-$C_{3-7}$ cycloalkyl, pyridinylmethyl or aryl-$C_{1-3}$ alkyl said aryl optionally substituted with one to three groups independently selected from halogen, cyano, $C_{1-6}$ alkyl, $C_{1-6}$ alkoxy; $R^3$ in each incidence is independently selected in each incidence from the group consisting of halogen, $C_{1-6}$ alkyl, $C_{1-6}$ haloalkyl or $C_{1-6}$ alkoxy; and, m and n are independently zero to two.

In another embodiment of the present invention there is provided a compound of formula I wherein A is A-1; X, $X^1$-$X^6$, $R^1$-$R^3$, $R^5$-$R^9$, $R^a$, $R^b$, $R^{a'}$, $R^{b'}$, m, n, o, p, q and r are as defined herein above.

In another embodiment of the present invention there is provided a compound of formula I wherein A is A-1 X is CH; $X^1$ is O; $X^6$ is absent; $R^1$ in each incidence is independently hydroxyl, halogen —$X^1(CH_2)_oCOR^5$, —$(CH_2)_oCOR^5$, —$X^1(CH_2)_oSO_2R^7$, —$(CH_2)_oSO_2R^7$, —$NR^6SO_2R^7$, —$X^4(CH_2)_r NR^{a'}R^{b'}$, —$X^5C(=O)R^9$, $CONR^aR^b$, —$CO_2R^6$, $NR^aR^b$ or nitro; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; and $R^5$-$R^9$, $R^a$, $R^b$, $R^{a'}$, $R^{b'}$ $X^2$-$X^5$, m, n, o, p, q and r are as defined hereinabove.

In another embodiment of the present invention there is provided a compound of formula I wherein A is A-1; X is CH; $X^1$ is O; $X^6$ is absent; $R^1$ in each incidence is independently —$X^1(CH_2)_oCOR^5$, —$NR^6SO_2R^7$, —$X^4(CH_2)_rNR^{a'}R^{b'}$, —$X^5C(=O)R^9$, nitro, $NR^aR^b$, halogen or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; and $R^5$-$R^9$, $R^a$, $R^b$, $R^{a'}$, $R^{b'}$ $X^2$-$X^5$, m, n, o, p, q and r are as defined hereinabove.

In another embodiment of the present invention there is provided a compound of formula I wherein A is A-1; X is CH; $X^1$ is O; $X^6$ is absent; m is one or two and the seven- and/or eight-positions are substituted; $R^1$ in each incidence is independently —$X^1(CH_2)_oCOR^5$, —$(CH_2)_oCOR^5$, —$X^1(CH_2)_o SO_2R^7$, —$(CH_2)_oSO_2R^7$, —$NR^6SO_2R^7$, —$X^4(CH_2)_r NR^{a'}R^{b'}$, —$X^5C(=O)R^9$, $CONR^aR^b$, —$CO_2R^6$, $NR^aR^b$, halogen, nitro, or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; and, $X^2$-$X^5$, $R^5$-$R^9$, $R^a$, $R^b$, $R^{a'}$, $R^{b'}$, n, o, p, q and r are as defined herein above.

In another embodiment of the present invention there is provided a compound of formula I wherein A is A-1; X is CH; $X^1$ is O; $X^6$ is absent; m is one or two and the 7 and/or 8-positions is(are) substituted; $R^1$ in each incidence is independently —$X^1(CH_2)_oCOR^5$, —$NR^6SO_2R^7$, —$X^4(CH_2)_r NR^{a'}R^{b'}$, —$X^5C(=O)R^9$, nitro, —$NR^aR^b$, halogen or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; and $X^2$-$X^5$, $R^5$-$R^9$, $R^a$, $R^b$, $R^{a'}$, $R^{b'}$ n, o, p, q and r are as defined hereinabove.

In another embodiment of the present invention there is provided a compound of formula I wherein A is A-1; X is CH; $X^1$ is O; $X^6$ is absent; m is one and the seven-position is substituted; $R^1$ is —$X^1(CH_2)_oCOR^5$, —$(CH_2)_oCOR^5$, —$X^1(CH_2)_oSO_2R^7$, —$(CH_2)_oSO_2R^7$, —$NR^6SO_2R^7$, —$X^4(CH_2)_r NR^{a'}R^{b'}$, —$X^5C(=O)R^9$, $CONR^aR^b$, —$CO_2R^6$, $NR^aR^b$, halogen, nitro, or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; and, $X^2$-$X^5$, $R^5$-$R^9$, $R^a$, $R^b$, $R^{a'}$, $R^{b'}$, n, o, p, q and r are as defined herein above.

In another embodiment of the present invention there is provided a compound of formula I wherein A is A-1; X is CH; $X^1$ is O; $X^6$ is absent; m is one and the seven-position is substituted; $R^1$ is —$X^1(CH_2)_oCOR^5$, —$NR^6SO_2R^7$, $X^4(CH_2)_r NR^{a'}R^{b'}$, —$X^5C(=O)R^9$, nitro, $NR^aR^b$, halogen or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; $X^2$-$X^5$, $R^5$-$R^9$, $R^a$, $R^b$, $R^{a'}$, $R^{b'}$, n, o, p, q and r are as defined herein above.

In another embodiment of the present invention there is provided a compound of formula I wherein A is A-1; X is CH; $X^1$ is O; $X^6$ is absent; m is one and the seven-position is substituted; $R^1$ is —$NR^6SO_2R^7$, nitro, $NR^aR^b$; $R^2$ is $C_{1-6}$ alkyl, $C_{3-7}$ cycloalkyl-$C_{1-3}$ alkyl or optionally substituted phenyl-$C_{1-3}$ alkyl; $R^3$ in each incidence is independently $C_{1-6}$ alkyl, $C_{1-6}$ alkoxy, halogen, —$NR^aR^b$, $C_{1-6}$ acylamino, $NR^6SO_2R^7$, cyano or nitro; $X^2$-$X^5$, $R^5$-$R^9$, $R^a$, $R^b$, $R^{a'}$, $R^{b'}$, n, o, p, q and r are as defined herein above.

In another embodiment of the present invention there is provided a compound of formula I wherein A is A-3; $X^1$-$X^6$, $R^1$, $R^2$, $R^4$-$R^9$, $R^a$, $R^b$, $R^{a'}$, $R^{b'}$, m, o, p, q and r are as defined herein above.

In another embodiment of the present invention there is provided a compound of formula I wherein A is A-3; $R^1$ in each incidence is independently selected from the group consisting of —$X^1(CH_2)_oCOR^5$, —$(CH_2)_oCOR^5$, —$X^1(CH_2)_o SO_2R^7$, —$(CH_2)_oSO_2R^7$, —$NR^6COR^5$, —$NR^6SO_2R^7$, —$X^4 (CH_2)_rNR^{a'}R^{b'}$, —$X^5C(=O)R^9$, —$CONR^aR^b$, —$CO_2R^6$, $NR^aR^b$, halogen, nitro and hydroxyl; $R^2$ is $C_{1-6}$ alkyl, $C_{3-7}$ cycloalkyl-$C_{1-3}$ alkyl or optionally substituted phenyl-$C_{1-3}$ alkyl; $X^6$ is absent; $X^1$ is O; $X^2$-$X^5$, $R^5$-$R^9$, $R^a$, $R^b$, $R^{a'}$, $R^{b'}$, m, o, p, q and r are as defined herein above.

In another embodiment of the present invention there is provided a compound of formula I wherein A is A-3; $R^1$ in each incidence is independently selected from the group consisting of —$X^1(CH_2)_oCOR^5$, —$(CH_2)_oCOR^5$, —$X^1(CH_2)_o SO_2R^7$, —$(CH_2)_oSO_2R^7$, —$NR^6COR^5$, —$NR^6SO_2R^7$, —$X^4 (CH_2)_rNR^{a'}R^{b'}$, —$X^5C(=O)R^9$, —$CONR^aR^b$, —$CO_2R^6$, $NR^aR^b$, halogen, nitro and hydroxyl; $R^2$ is $C_{1-6}$ alkyl, $C_{3-7}$ cycloalkyl-$C_{1-3}$ alkyl or optionally substituted phenyl-$C_{1-3}$ alkyl; $R^4$ is $C_{1-6}$ alkyl or $C_{3-7}$ cycloalkyl; $X^6$ is absent; $X^1$ is O; $X^2$-$X^5$, $R^5$-$R^9$, $R^a$, $R^b$, $R^{a'}$, $R^{b'}$, m, o, p, q and r are as defined herein above.

In another embodiment of the present invention there is provided a compound of formula I wherein A is A-3; m is one or two and the seven- and/or eight-position(s) is(are) substituted; $R^1$ in each incidence is independently selected from the group consisting of —$X^1(CH_2)_oCOR^5$, —$(CH_2)_oCOR^5$, —$X^1(CH_2)_oSO_2R^7$, —$(CH_2)_oSO_2R^7$, —$NR^6SO_2R^7$, —$X^4 (CH_2)_rNR^{a'}R^{b'}$, —$X^5C(=O)R^9$, —$CONR^aR^b$, —$CO_2R^6$, $NR^aR^b$, halogen, nitro, or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $X^6$ is absent; $X^1$ is O; $X^2$-$X^5$, $R^5$-$R^9$, $R^a$, $R^b$, $R^{a'}$, $R^{b'}$, o, p, q and r are as defined herein above.

In another embodiment of the present invention there is provided a compound of formula I wherein A is A-3; m is one or two and the seven- and/or eight-position(s) is(are) substituted; $R^1$ in each incidednce is independently selected from the group consisting of —$X^1(CH_2)_oCOR^5$, —$NR^6SO_2R^7$, —$X^4(CH_2)_rNR^{a'}R^{b'}$, —$X^5C(=O)R^9$, $NR^aR^b$, nitro, halogen or hydroxyl; $R^2$ is $C_{1-6}$ alkyl, $C_{3-7}$ cycloalkyl-$C_{1-3}$ alkyl or optionally substituted phenyl-$C_{1-3}$ alkyl; $X^6$ is absent; $X^1$ is O; $X^2$-$X^5$, $R^5$-$R^9$, $R^a$, $R^b$, $R^{a'}$, $R^{b'}$, o, p, q and r are as defined herein above.

In another embodiment of the present invention there is provided a compound of formula I wherein A is A-3; m is one, the seven-position is substituted; $R^1$ is —$NR^6SO_2R^7$, $NR^aR^b$ or nitro; $R^2$ is $C_{1-6}$ alkyl, $C_{3-7}$ cycloalkyl-$C_{1-3}$ alkyl or optionally substituted phenyl-$C_{1-3}$ alkyl; $X^6$ is absent; $X^1$ is O; $X^2$-$X^5$, $R^6$-$R^9$, $R^a$, $R^b$, o, p, q and r are as defined herein above.

In another embodiment of the present invention there is provided a compound of formula I wherein A is A-2; $R^{10}$ is phenyl optionally substituted with one to three substituents independently selected from the group consisting of $C_{1-3}$ alkyl, $C_{1-3}$ alkoxy, $C_{1-3}$haloalkyl, halogen, $NR^aR^b$, cyano and nitro; $X^1$-$X^6$, $R^1$, $R^2$, $R^5$-$R^9$, $R^a$, $R^b$, $R^{a'}$, $R^{b'}$, m, o, p, q and r are as defined herein above.

In another embodiment of the present invention there is provided a compound of formula I wherein A is A-2; $R^1$ in each incidence is independently selected from the group consisting of —$X^1(CH_2)_oCOR^5$, —$NR^6SO_2R^7$, —$X^4(CH_2)_rNR^{a'}R^{b'}$, —$X^5C(=O)R^9$, $NR^aR^b$, nitro, halogen and hydroxyl; $R^2$ is $C_{1-6}$ alkyl, phenyl-$C_{1-4}$ alkyl or $C_{3-7}$ cycloalkyl-$C_{1-4}$ alkyl; $R^{10}$ is phenyl optionally substituted with one to three substituents independently selected from the group consisting of $C_{1-13}$ alkyl, $C_{1-13}$ alkoxy, $C_{1-3}$ haloalkyl, halogen, $NR^aR^b$, cyano and nitro; $X^1$ is O, and, $X^6$ is absent; $X^2$-$X^5$, $R^5$-$R^9$, $R^a$, $R^b$, m, o, p, q and r are as defined hereinabove.

In another embodiment of the present invention there is provided a compound of formula I wherein A is A-4; and, $X^1$-$X^5$, $R^1$, $R^2$, $R^4$-$R^9$, $R^a$, $R^b$, $R^{a'}$, $R^{b'}$, m, o, p, q and r are as defined hereinabove.

In another embodiment of the present invention there is provided a compound of formula I wherein A is A-4; $R^1$ in each incidence is independently selected from the group consisting of —$X^1(CH_2)_oCOR^5$, —$NR^6SO_2R^7$, —$X^4(CH_2)_rNR^{a'}R^{b'}$, —$X^5C(=O)R^9$, halogen and hydroxyl; $R^2$ is $C_{1-6}$ alkyl, phenyl-$C_{1-4}$ alkyl or $C_{3-7}$ cycloalkyl-$C_{1-4}$ alkyl; $X^1$ is O; and $X^2$-$X^5$, $R^4$-$R^9$, $R^a$, $R^b$, m, o, p, q and r are as defined hereinabove.

In another embodiment of the present invention there is provided a compound of formula I wherein A is A-5; and $X^1$-$X^6$, $R^1$-$R^3$, $R^5$-$R^9$, $R^a$, $R^b$, $R^{a'}$, $R^{b'}$, m, n, o, p, q and r are as defined hereinabove In another embodiment of the present invention there is provided a compound of formula I wherein A is A-5; $R^1$ in each incidence is independently selected from the group consisting of —$X^1(CH_2)_oCOR^5$, —$(CH_2)_oCOR^5$, —$X^1(CH_2)_o SO_2R^7$, —$(CH_2)_oSO_2R^7$, —$NR^6SO_2R^7$, —$X^4(CH_2)_r NR^{a'}R^{b'}$, $X^5C(=O)R^9$, $CONR^aR^b$, —$CO_2R^6$, $NR^aR^b$, halogen, nitro, and hydroxyl; $R^2$ is $C_{1-6}$ alkyl, optionally substituted aryl-$C_{1-4}$ alkyl or $C_{3-7}$ cycloalkyl-$C_{1-4}$ alkyl; $R^3$ is $C_{1-6}$ alkyl, $C_{1-6}$ alkoxy, halogen, —$NR^aR^b$, $C_{1-6}$ acylamino, $NR^6SO_2R^7$, cyano or nitro; $X^1$ is O; $X^6$ is absent; and $X^2$-$X^5$, $R^5$-$R^9$, $R^a$, $R^b$, $R^{a'}$, $R^{b'}$, m, n, o, p, q and r are as defined herein above.

In another embodiment of the present invention there is provided a compound of formula I wherein A is A-6; and, $X^1$-$X^5$, $R^1$, $R^2$, $R^4$-$R^9$, $R^a$, $R^b$, $R^{a'}$, $R^{b'}$, m, o, p, q and r are as defined herein above.

In another embodiment of the present invention there is provided a compound of formula I wherein A is A-7 or A-8; and, $X^1$-$X^5$, $R^1$, $R^2$, $R^4$-$R^9$, $R^a$, $R^b$, $R^{a'}$, $R^{b'}$, m, o, p, q and r are as defined herein above.

In another embodiment of the present invention there is provided a compound of formula I wherein A is A-7 or A-8; $X^1$ is O; $X^6$ is absent; $R^1$ in each incidence is independently hydroxyl, halogen —$X^1(CH_2)_oCOR^5$, —$(CH_2)_oCOR^5$, —$X^1 (CH_2)_oSO_2R^7$, —$(CH_2)_oSO_2R^7$, —$NR^6SO_2R^7$, —$X^4(CH_2)_r NR^{a'}R^{b'}$, —$X^5C(=O)R^9$, —$CONR^aR^b$, —$CO_2R^6$, $NR^aR^b$ or nitro; $R^2$ is $C_{1-6}$ alkyl, $C_{3-7}$ cycloalkyl-$C_{1-3}$ alkyl or optionally substituted phenyl-$C_{1-3}$ alkyl; and $R^5$-$R^9$, $R^a$, $R^b$, $R^{a'}$, $R^{b'}$ $X^2$-$X^5$, m, o, p, q and r are as defined hereinabove.

In another embodiment of the present invention there is provided a compound of formula I wherein A is A-7 or A-8; $X^1$ is O; $X^6$ is absent; $R^1$ in each incidence is independently hydroxyl, halogen —$X^1(CH_2)_oCOR^5$, —$NR^6SO_2R^7$, —$X^4 (CH_2)_rNR^{a'}R^{b'}$, —$X^5C(=O)R^9$, —$N^aR^b$ or nitro; $R^2$ is $C_{1-6}$ alkyl, $C_{3-7}$ cycloalkyl-$C_{1-3}$ alkyl or optionally substituted phenyl-$C_{1-3}$ alkyl; and $R^5$-$R^9$, $R^a$, $R^b$, $R^{a'}$, $R^{b'}$ $X^2$-$X^5$, m, o, p, q and r are as defined hereinabove.

In another embodiment of the present invention there is provided a compound of formula I wherein A is A-7 or A-8; $X^1$ is O; $X^6$ is absent; m is one or two and the seven- and/or eight-position(s) is(are) substituted; $R^1$ in each incidence is independently hydroxyl, halogen —$X^1(CH_2)_oCOR^5$, —$(CH_2)_oCOR^5$, —$X^1(CH_2)_oSO_2R^7$, —$(CH_2)_oSO_2R^7$, —$NR^6SO_2R^7$, —$X^4(CH_2)_rNR^{a'}R^{b'}$, —$X^5C(=O)R^9$, —$CONR^aR^b$, —$CO_2R^6$, $NR^aR^b$ or nitro; $R^2$ is $C_{1-6}$ alkyl, $C_{3-7}$ cycloalkyl-$C_{1-3}$ alkyl or optionally substituted phenyl-$C_{1-3}$ alkyl; and $R^5$-$R^9$, $R^a$, $R^b$, $R^{a'}$, $R^{b'}$ $X^2$-$X^5$, o, p, q and r are as defined hereinabove.

In another embodiment of the present invention there is provided a compound of formula I wherein A is A-7 or A-8; $X^1$ is O; $X^6$ is absent; m is one or two and the seven- and/or eight-position(s) is(are) substituted; $R^1$ in each incidence is independently hydroxyl, halogen —$X^1(CH_2)_oCOR^5$, —$NR^6SO_2R^7$, —$X^4(CH_2)_rNR^{a'}R^{b'}$, —$X^5C(=O)R^9$, —$NR^aR^b$ or nitro; $R^2$ is $C_{1-6}$ alkyl, $C_{3-7}$ cycloalkyl-$C_{1-3}$ alkyl or optionally substituted phenyl-$C_{1-3}$ alkyl; and $R^5$-$R^9$, $R^a$, $R^b$, $R^{a'}$, $R^{b'}$ $X^2$-$X^5$, o, p, q and r are as defined hereinabove.

In another embodiment of the present invention there is provided a compound of formula I wherein A is A-7 or A-8; $X^1$ is O; $X^6$ is absent; m is one and the seven-position is substituted; $R^1$ is hydroxyl, halogen —$X^1(CH_2)_oCOR^5$, —$(CH_2)_oCOR^5$, —$X^1(CH_2)_oSO_2R^7$, —$(CH_2)_oSO_2R^7$, —$NR^6SO_2R^7$, —$X^4(CH_2)_rNR^{a'}R^{b'}$, —$X^5C(=O)R^9$, —CONR$^a$R$^b$, —CO$_2$R$^6$, NR$^a$R$^b$ or nitro; R$^2$ is C$_{1-6}$ alkyl, C$_{3-7}$ cycloalkyl-C$_{1-3}$ alkyl or optionally substituted phenyl-C$_{1-3}$ alkyl; and R$^5$-R$^9$, R$^a$, R$^b$, R$^{a\prime}$, R$^{b\prime}$ X$^2$-X$^5$, o, p, q and r are as defined hereinabove.

In another embodiment of the present invention there is provided a compound of formula I wherein A is A-7 or A-8; X$^1$ is O; X$^6$ is absent; m is one and the seven-position is substituted; R$^1$ is hydroxyl, halogen —X$^1$(CH$_2$)$_o$COR$^5$, —NR$^6$SO$_2$R$^7$, —X$^4$(CH$_2$)$_r$NR$^a$R$^{b\prime}$, —X$^5$C(=O)R$^9$, —NR$^a$R$^b$ or nitro; R$^2$ is C$_{1-6}$ alkyl, C$_{3-7}$ cycloalkyl-C$_{1-3}$ alkyl or optionally substituted phenyl-C$_{1-3}$ alkyl; and R$^5$-R$^9$, R$^a$, R$^b$, R$^{a\prime}$, R$^{b\prime}$ X$^2$-X$^5$, o, p, q and r are as defined hereinabove.

In another embodiment of the present invention there is provided a compound of formula I wherein A is A-7 or A-8; X$^1$ is O; X$^6$ is absent; m is one and the seven-position is substituted; R$^1$ is —NR$^6$SO$_2$R$^7$, —NR$^a$R$^b$ or nitro; R$^2$ is C$_{1-6}$ alkyl, C$_{3-7}$ cycloalkyl-C$_{1-3}$ alkyl or optionally substituted phenyl-C$_{1-3}$ alkyl; and R$^5$-R$^9$, R$^a$, R$^b$, R$^{a\prime}$, R$^{b\prime}$ X$^2$-X$^5$, o, p, q and r are as defined hereinabove.

In another embodiment of the present invention there is provided a compound selected from the following:

3-(1,1-Dioxo-1,4-dihydro-1λ$^6$-benzo[1,4]thiazin-3-yl)-4-hydroxy-1-(3-methyl-butyl)-1H-quinolin-2-one;

1-(2-Cyclopropyl-ethyl)-3-(1,1-dioxo-1,4-dihydro-1λ$^6$-benzo[1,4]thiazin-3-yl)-6-fluoro-4-hydroxy-1H-quinolin-2-one;

6-Chloro-3-(1,1-dioxo-1,4-dihydro-1λ$^6$-benzo[1,4]thiazin-3-yl)-4-hydroxy-1-(3-methyl-butyl)-1H-quinolin-2-one;

1-(2-Cyclopropyl-ethyl)-3-(1,1-dioxo-1,4-dihydro-1λ$^6$-benzo[1,4]thiazin-3-yl)-4-hydroxy-6-methyl-1H-quinolin-2-one;

1-(2-Cyclopropyl-ethyl)-3-(1,1-dioxo-1,4-dihydro-1λ$^6$-benzo[1,4]thiazin-3-yl)-4-hydroxy-6-methoxy-1H-quinolin-2-one;

6-Chloro-1-(2-cyclopropyl-ethyl)-3-(1,1-dioxo-1,4-dihydro-1λ$^6$-benzo[1,4]thiazin-3-yl)-4-hydroxy-1H-quinolin-2-one;

3-(6-Chloro-1,1-dioxo-1,4-dihydro-1λ$^6$-benzo[1,4]thiazin-3-yl)-4-hydroxy-1-(3-methyl-butyl)-1H-quinolin-2-one;

3-(1,1-Dioxo-1,4-dihydro-1λ$^6$-benzo[1,4]thiazin-3-yl)-1-(2-fluoro-benzyl)-4-hydroxy-1H-quinolin-2-one;

3-(1,1-Dioxo-1,4-dihydro-1λ$^6$-benzo[1,4]thiazin-3-yl)-1-(4-fluoro-benzyl)-4-hydroxy-1H-quinolin-2-one;

3-(1,1-Dioxo-1,4-dihydro-1λ$^6$-benzo[1,4]thiazin-3-yl)-1-(4-fluoro-benzyl)-4-hydroxy-1H-quinolin-2-one, sodium salt;

1-(2-Cyclopropyl-ethyl)-3-(1,1-dioxo-1,4-dihydro-1λ$^6$-benzo[1,4]thiazin-3-yl)-4-hydroxy-1H-[1,8]naphthyridin-2-one;

3-(1,1-Dioxo-1,4-dihydro-1λ$^6$-benzo[1,4]thiazin-3-yl)-4-hydroxy-1-(3-methyl-butyl)-1H-[1,8]naphthyridin-2-one;

3-(1,1-Dioxo-1,4-dihydro-1λ$^6$-benzo[1,4]thiazin-3-yl)-6-fluoro-4-hydroxy-1-(3-methyl-butyl)-1H-[1,8]naphthyridin-2-one;

3-(1,1-Dioxo-1,4-dihydro-1λ$^6$-benzo[1,4]thiazin-3-yl)-6-fluoro-1-(4-fluoro-benzyl)-4-hydroxy-1H-quinolin-2-one;

3-(1,1-Dioxo-1,4-dihydro-1λ$^6$-benzo[1,4]thiazin-3-yl)-6-fluoro-1-(4-fluoro-benzyl)-4-hydroxy-1H-quinolin-2-one, sodium salt;

3-(1,1-Dioxo-1,4-dihydro-1λ$^6$-benzo[1,4]thiazin-3-yl)-1-(4-fluoro-benzyl)-4-hydroxy-6-methyl-1H-quinolin-2-one;

3-(1,1-Dioxo-1,4-dihydro-1λ$^6$-benzo[1,4]thiazin-3-yl)-1-(4-fluoro-benzyl)-4-hydroxy-6-methyl-1H-quinolin-2-one, sodium salt;

1-(2-Cyclopropyl-ethyl)-6-fluoro-4-hydroxy-3-(7-nitro-1,1-dioxo-1,4-dihydro-1λ$^6$-benzo[1,4]thiazin-3-yl)-1H-quinolin-2-one;

3-(6-Cyano-1,1-dioxo-1,4-dihydro-1λ$^6$-benzo[1,4]thiazin-3-yl)-4-hydroxy-1-(3-methyl-butyl)-1H-quinolin-2-one;

3-(6-Aminomethyl-1,1-dioxo-1,4-dihydro-1λ$^6$-benzo[1,4]thiazin-3-yl)-4-hydroxy-1-(3-methyl-butyl)-1H-quinolin-2-one;

6-Fluoro-1-(4-fluoro-benzyl)-4-hydroxy-3-(7-hydroxy-1,1-dioxo-1,4-dihydro-1λ$^6$-benzo[1,4]thiazin-3-yl)-1H-quinolin-2-one;

3-(7-Benzyloxy-1,1-dioxo-1,4-dihydro-1λ$^6$-benzo[1,4]thiazin-3-yl)-6-fluoro-1-(4-fluoro-benzyl)-4-hydroxy-1H-quinolin-2-one;

2-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yloxy}-acetamide;

3-(7-Amino-1,1-dioxo-1,4-dihydro-1λ$^6$-benzo[1,4]thiazin-3-yl)-1-(2-cyclopropyl-ethyl)-4-hydroxy-1H-quinolin-2-one;

3-(7-Amino-1,1-dioxo-1,4-dihydro-1λ$^6$-benzo[1,4]thiazin-3-yl)-6-fluoro-1-(4-fluoro-benzyl)-4-hydroxy-1H-quinolin-2-one;

N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-acetamide;

N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide, sodium salt;

1-(3,4-Difluoro-benzyl)-3-(1,1-dioxo-1,4-dihydro-1λ$^6$-benzo[1,4]thiazin-3-yl)-6-fluoro-4-hydroxy-1H-quinolin-2-one;

1-(3,4-Difluoro-benzyl)-3-(1,1-dioxo-1,4-dihydro-1λ$^6$-benzo[1,4]thiazin-3-yl)-6-fluoro-4-hydroxy-1H-quinolin-2-one, sodium salt;

3-(1,1-Dioxo-1,4-dihydro-1λ$^6$-benzo[1,4]thiazin-3-yl)-6-fluoro-1-(4-fluoro-3-methyl-benzyl)-4-hydroxy-1H-quinolin-2-one;

3-(1,1-Dioxo-1,4-dihydro-1λ$^6$-benzo[1,4]thiazin-3-yl)-6-fluoro-1-(4-fluoro-3-methyl-benzyl)-4-hydroxy-1H-quinolin-2-one, sodium salt;

3-[3-(1,1-Dioxo-1,4-dihydro-1λ$^6$-benzo[1,4]thiazin-3-yl)-6-fluoro-4-hydroxy-2-oxo-2H-quinolin-1-ylmethyl]-benzonitrile;

3-[3-(1,1-Dioxo-1,4-dihydro-1λ$^6$-benzo[1,4]thiazin-3-yl)-6-fluoro-4-hydroxy-2-oxo-2H-quinolin-1-ylmethyl]-benzonitrile, sodium salt;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-methanesulfonamide, sodium salt;

Propane-1-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-amide;

Propane-1-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-amide, sodium salt;

6-Fluoro-1-(4-fluoro-benzyl)-4-hydroxy-3-(7-methoxy-1,1-dioxo-1,4-dihydro-1λ$^6$-benzo[1,4]thiazin-3-yl)-1H-quinolin-2-one;

{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-acetic acid methyl ester;

Ethanesulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

Cyclopropanesulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

2-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-N,N-dimethyl-acetamide;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-N-methyl-methanesulfonamide;

3,5-Dimethyl-isoxazole-4-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-benzenesulfonamide;

1-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-3-methyl-urea;

3-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yloxy}-propionamide;

N-{3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-sulfamide (I-40);

Pyrrolidine-1-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide (I-65);

2-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-N-methyl-acetamide;

Ethanesulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

N-[3-(4-Hydroxy-1-methyl-2-oxo-1,2-dihydro-quinolin-3-yl)-1,1-dioxo-1,4-dihydro-1λ⁶-benzo[1,4]thiazin-7-yl]-methanesulfonamide;

N-{3-[1-(4-Fluoro-benzyl)-4-hydroxy-6-methyl-2-oxo-1,2-dihydro-quinolin-3-yl]-1,1-dioxo-1,4-dihydro-1λ⁶-benzo[1,4]thiazin-7-yl}-methanesulfonamide;

Propane-1-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

N-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-N-methyl-methanesulfonamide;

N-{3-[6-Fluoro-1-(4-fluoro-3-methyl-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-{3-[1-(3-Chloro-4-fluoro-benzyl)-6-fluoro-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-[3-(6-Fluoro-4-hydroxy-2-oxo-1-pyridin-3-ylmethyl-1,2-dihydro-quinolin-3-yl)-1,1-dioxo-1,4-dihydro-1λ⁶-benzo[1,4]thiazin-7-yl]-methanesulfonamide;

N-[3-(1-Cyclohexylmethyl-6-fluoro-4-hydroxy-2-oxo-1,2-dihydro-quinolin-3-yl)-1,1-dioxo-1,4-dihydro-1λ⁶-benzo[1,4]thiazin-7-yl]-methanesulfonamide;

N-{3-[6-Fluoro-4-hydroxy-1-(3-methyl-butyl)-2-oxo-1,2-dihydro-quinolin-3-yl]-1,1-dioxo-1,4-dihydro-1λ⁶-benzo[1,4]thiazin-7-yl}-methanesulfonamide;

Cyclopropanesulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

N-{3-[1-(3,4-Difluoro-benzyl)-6-fluoro-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-{3-[6-Fluoro-1-(4-fluoro-3-trifluoromethyl-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-C-phenyl-methanesulfonamide;

2-Oxo-oxazolidine-3-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

N-{3-[1-(4-Fluoro-benzyl)-4-hydroxy-6-methoxy-2-oxo-1,2-dihydro-quinolin-3-yl]-1,1-dioxo-1,4-dihydro-1λ⁶-benzo[1,4]thiazin-7-yl}-methanesulfonamide;

N-{3-[6-Chloro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide;

Propane-2-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

Butane-1-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

N-{3-[1-(4-Fluoro-benzyl)-6-fluoro-4-hydroxy-2-oxo-1,2-dihydro-quinolin-3-yl]-1,1-dioxo-1,4-dihydro-1λ⁶-benzo[1,4]thiazin-7-yl}-sulfamide (I-64);

1-{3-[1-(4-Fluoro-benzyl)-6-fluoro-4-hydroxy-2-oxo-1,2-dihydro-quinolin-3-yl]-1,1-dioxo-1,4-dihydro-1λ⁶-benzo[1,4]thiazin-7-yl}-3,3-dimethyl-sulfamide (I-62);

N-{3-[6,7-Difluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-[3-(6-Fluoro-4-hydroxy-2-oxo-1-pyridin-4-ylmethyl-1,2-dihydro-quinolin-3-yl)-1,1-dioxo-1,4-dihydro-1λ⁶-benzo[1,4]thiazin-7-yl]-methanesulfonamide; compound with trifluoro-acetic acid;

N-{3-[7-Chloro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide;

6-Fluoro-1-(4-fluoro-benzyl)-4-hydroxy-3-(7-methoxymethyl-1,1-dioxo-1,4-dihydro-1λ⁶-benzo[1,4]thiazin-3-yl)-1H-quinolin-2-one;

5-(7-Amino-1,1-dioxo-1,4-dihydro-1λ⁶-benzo[1,4]thiazin-3-yl)-7-(4-fluoro-benzyl)-4-hydroxy-2-methyl-7H-thieno[2,3-b]pyridin-6-one;

N-{3-[7-(4-Fluoro-benzyl)-4-hydroxy-2-methyl-6-oxo-6,7-dihydro-thieno[2,3-b]pyridin-5-yl]-1,1-dioxo-1,4-dihydro-1λ⁶-benzo[1,4]thiazin-7-yl}-methanesulfonamide;

N-{3-[7-(4-Fluoro-benzyl)-4-hydroxy-6-oxo-6,7-dihydro-thieno[2,3-b]pyridin-5-yl]-1,1-dioxo-1,4-dihydro-1λ⁶-benzo[1,4]thiazin-7-yl}-methanesulfonamide;

(S)-5-tert-Butyl-3-(1,1-dioxo-1,4-dihydro-1λ⁶-benzo[1,4]thiazin-3-yl)-4-hydroxy-1-(3-methyl-butyl)-1,5-dihydro-pyrrol-2-one;

(S)-5-Cyclohexyl-3-(1,1-dioxo-1,4-dihydro-1λ⁶-benzo[1,4]thiazin-3-yl)-4-hydroxy-1-(3-methyl-butyl)-1,5-dihydro-pyrrol-2-one;

(S)-5-((S)-sec-Butyl)-3-(1,1-dioxo-1,4-dihydro-1λ⁶-benzo[1,4]thiazin-3-yl)-4-hydroxy-1-(3-methyl-butyl)-1,5-dihydro-pyrrol-2-one;
(S)-1-Benzyl-5-((S)-sec-butyl)-3-(1,1-dioxo-1,4-dihydro-1λ⁶-benzo[1,4]thiazin-3-yl)-4-hydroxy-1,5-dihydro-pyrrol-2-one;
(S)-3-(1,1-Dioxo-1,4-dihydro-1λ⁶-benzo[1,4]thiazin-3-yl)-1-(4-fluoro-benzyl)-4-hydroxy-5-isobutyl-1,5-dihydro-pyrrol-2-one;
(S)-5-Cyclohexyl-3-(1,1-dioxo-1,4-dihydro-1λ⁶-benzo[1,4]thiazin-3-yl)-1-(4-fluoro-benzyl)-4-hydroxy-1,5-dihydro-pyrrol-2-one;
(S)-5-Cyclohexyl-3-(1,1-dioxo-1,4-dihydro-1λ⁶-benzo[1,4]thiazin-3-yl)-1-(4-fluoro-benzyl)-4-hydroxy-1,5-dihydro-pyrrol-2-one; sodium salt;
N-{3-[(S)-5-tert-Butyl-1-(4-fluoro-benzyl)-4-hydroxy-2-oxo-2,5-dihydro-1H-pyrrol-3-yl]-1,1-dioxo-1,4-dihydro-1λ⁶-benzo[1,4]thiazin-7-yl}-methanesulfonamide;
N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1,4-dihydro-1λ⁶-benzo[1,4]thiazin-7-yl}-methanesulfonamide;
N-{3-[(S)-5-tert-Butyl-1-(4-fluoro-3-methoxy-benzyl)-4-hydroxy-2-oxo-2,5-dihydro-1H-pyrrol-3-yl]-1,1-dioxo-1,4-dihydro-1λ⁶-benzo[1,4]thiazin-7-yl}-methanesulfonamide;
N-{3-[(S)-5-tert-Butyl-1-(3-chloro-4-fluoro-benzyl)-4-hydroxy-2-oxo-2,5-dihydro-1H-pyrrol-3-yl]-1,1-dioxo-1,4-dihydro-1λ⁶-benzo[1,4]thiazin-7-yl}-methanesulfonamide;
(S)-5-tert-Butyl-1-(4-fluoro-benzyl)-4-hydroxy-3-(7-nitro-1,1-dioxo-1,4-dihydro-1λ⁶-benzo[1,4]thiazin-3-yl)-1,5-dihydro-pyrrol-2-one;
(S)-3-(7-Amino-1,1-dioxo-1,4-dihydro-1λ⁶-benzo[1,4]thiazin-3-yl)-5-tert-butyl-1-(4-fluoro-benzyl)-4-hydroxy-1,5-dihydro-pyrrol-2-one;
N-{3-[(S)-5-tert-Butyl-1-(4-fluoro-benzyl)-4-hydroxy-2-oxo-2,5-dihydro-1H-pyrrol-3-yl]-1,1-dioxo-1,4-dihydro-1λ⁶-benzo[1,4]thiazin-7-yl}-sulfamide (II-14);
(S)-3-(7-Amino-1,1-dioxo-1,4-dihydro-1λ⁶-benzo[1,4]thiazin-3-yl)-5-tert-butyl-1-(2-cyclopropyl-ethyl)-4-hydroxy-1,5-dihydro-pyrrol-2-one;
N-{3-[(S)-5-tert-Butyl-1-(2-cyclopropyl-ethyl)-4-hydroxy-2-oxo-2,5-dihydro-1H-pyrrol-3-yl]-1,1-dioxo-1,4-dihydro-1λ⁶-benzo[1,4]thiazin-7-yl}-methanesulfonamide;
1-tert-Butyl-4-(1,1-dioxo-1,4-dihydro-1λ⁶-benzo[1,4]thiazin-3-yl)-2-(4-fluoro-benzyl)-5-hydroxy-1,2-dihydro-pyrazol-3-one;
N-{3-[4-(4-Fluoro-benzyl)-7-hydroxy-5-oxo-4,5-dihydro-thieno[3,2-b]pyridin-6-yl]-1,1-dioxo-1,4-dihydro-1λ⁶-benzo[1,4]thiazin-7-yl}-methanesulfonamide; or,
N-{3-[2-Ethyl-7-(4-fluoro-benzyl)-4-hydroxy-6-oxo-6,7-dihydro-thieno[2,3-b]pyridin-5-yl]-1,1-dioxo-1,4-dihydro-1λ⁶-benzo[1,4]thiazin-7-yl}-methanesulfonamide.

In another embodiment of the present invention there is provided a method for treating a disease caused by the Hepatitis C Virus (HCV) virus comprising administering to a patient in need thereof, a therapeutically effective quantity of a compound according to formula I wherein A, X, $X^1$-$X^6$, $R^1$-$R^{10}$, $R^a$, $R^b$, $R^{a'}$, $R^{b'}$, m, n, o, p, q and r are as defined herein above.

In another embodiment of the present invention there is provided a method for treating a disease caused by the Hepatitis C Virus (HCV) virus comprising administering to a patient in need thereof, a therapeutically effective quantity of a compound according to formula I wherein A is A-1, A-7 or A-8 and X, $X^1$-$X^6$, $R^1$-$R^3$, $R^5$-$R^9$, $R^a$, $R^b$, $R^{a'}$, $R^{b'}$, m, n, o, p, q and r are as defined herein above.

In another embodiment of the present invention there is provided a method for treating a disease caused by the Hepatitis C Virus (HCV) virus comprising administering to a patient in need thereof, a therapeutically effective quantity of a compound according to formula I wherein A is A-3, X, $X^1$-$X^6$, $R^1$, $R^2$, $R^4$-$R^9$, $R^a$, $R^b$, $R^{a'}$, $R^{b'}$, m, o, p, q and r are as defined herein above.

In another embodiment of the present invention there is provided a method for treating a disease caused by the Hepatitis C Virus (HCV) virus comprising administering to a patient in need thereof, a therapeutically effective quantity of a compound according to formula I wherein A, X, $X^1$-$X^5$, $R^1$-$R^{10}$, $R^a$, $R^b$, m, n, o, p, q and r are as defined in claim 2.

In another embodiment of the present invention there is provided a method for treating a disease caused by the Hepatitis C Virus (HCV) virus co-comprising administering to a patient in need thereof, a therapeutically effective quantity of a compound according to formula I wherein A, X, $X^1$-$X^6$, $R^1$-$R^{10}$, $R^a$, $R^b$, $R^{a'}$, $R^{b'}$, m, n, o, p, q and r are as defined herein above; and, at least one immune system modulator and/or at least one antiviral agent that inhibits replication of HCV In another embodiment of the present invention there is provided a method for treating a disease caused by the Hepatitis C Virus (HCV) virus co-comprising administering to a patient in need thereof, a therapeutically effective quantity of a compound according to formula I wherein A, X, $X^1$-$X^6$, $R^1$-$R^{10}$, $R^a$, $R^b$, $R^{a'}$, $R^{b'}$, m, n, o, p, q and r are as defined herein above; and, an interferon, interleukin, tumor necrosis factor or colony stimulating factor In another embodiment of the present invention there is provided a method for treating a disease caused by the Hepatitis C Virus (HCV) virus co-comprising administering to a patient in need thereof, a therapeutically effective quantity of a compound according to formula I wherein A, X, $X^1$-$X^6$, $R^1$-$R^{10}$, $R^a$, $R^b$, $R^{a'}$, $R^{b'}$, m, n, o, p, q and r are as defined herein above; and, an interferon or chemically derivatized interferon.

In another embodiment of the present invention there is provided a method for treating a disease caused by the Hepatitis C Virus (HCV) virus co-comprising administering to a patient in need thereof, a therapeutically effective quantity of a compound according to formula I wherein A, X, $X^1$-$X^6$, $R^1$-$R^{10}$, $R^a$, $R^b$, $R^{a'}$, $R^{b'}$, m, n, o, p, q and r are as defined herein above; and an HCV protease inhibitor, another HCV polymerase inhibitor, a HCV helicase inhibitor, a HCV primase inhibitor or a HCV fusion inhibitor.

In another embodiment of the present invention there is provided a method for inhibiting replication of the HCV virus comprising exposing the virus to a compound according to formula I wherein A, X, $X^1$-$X^6$, $R^1$-$R^{10}$, $R^a$, $R^b$, $R^{a'}$, $R^{b'}$, m, n, o, p, q and r are as defined herein above.

In another embodiment of the present invention there is provided a pharmaceutical composition for treating a disease caused by the HCV comprising co-administering to a patient in need thereof, a therapeutically effective quantity of a compound of formula I wherein A, X, $X^1$-$X^6$, $R^1$-$R^{10}$, $R^a$, $R^b$, $R^{a'}$, $R^{b'}$, m, n, o, p, q and r are as defined herein above admixed with at least one pharmaceutically acceptable carrier, diluent or excipient.

In another embodiment of the present invention there is provided a pharmaceutical composition for treating a disease caused by the HCV comprising co-administering to a patient in need thereof, a therapeutically effective quantity of a compound of formula I wherein A, X, $X^1$-$X^5$, $R^1$-$R^{10}$, $R^a$, $R^b$, m, n, o, p, q and r are as defined in claim 2 admixed with at least one pharmaceutically acceptable carrier, diluent or excipient.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition for each group as provided in the Summary of the Invention.

The terms "optional" or "optionally" as used herein means that a described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like.

Compounds of the present invention may have asymmetric centers located on substituents linked to the heterocyclic scaffold that produce enantiomers or diastereomers. All stereoisomers of compounds of the instant invention are contemplated, either in admixture or in pure or substantially pure form. The definition of the compounds according to the invention embraces all both isolated optical isomers enantiomers and their mixtures including the racemic form. The pure optical isomer can be prepared by stereospecific synthesis or by resolution of the racemic form by physical methods, such as, for example, fractional crystallization of diastereomeric salts, separation or crystallization of diastereomeric derivatives or separation by chiral column chromatography.

The term "alkyl" as used herein denotes an unbranched or branched chain hydrocarbon residue containing 1 to 18 carbon atoms. The term "lower alkyl" denotes an unbranched or branched chain hydrocarbon residue containing 1 to 6 carbon atoms. Representative lower alkyl groups include methyl, ethyl, propyl, i-propyl, n-butyl, i-butyl, t-butyl or pentyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below.

The term "alkylene" as used herein denotes a divalent saturated linear hydrocarbon radical of 1 to 6 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, and 2-ethylbutylene.

The term "acylamino" as used herein denotes a group of formula —NHC(=O)R wherein R is hydrogen or lower alkyl as defined herein The terms "alkylsulfonylamino", "cycloalkylsulfonylamino" and "arylsulfonylamino" as used herein denotes a group of formula —NR'S(=O)$_2$R wherein R is alkyl, cycloalkyl or aryl respectively, R' is hydrogen or $C_{1-3}$ alkyl, and alkyl, cycloalkyl and aryl are as defined herein.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl and 2,2,2-trifluoroethyl. The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "alkenyl" as used herein denotes an unsubstituted or substituted hydrocarbon chain radical having from 2 to 18 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes an unsubstituted hydrocarbon chain radical having from 2 to 18 carbon atoms, preferably 2 to 4 carbon atoms, and having one or where possible two triple bonds. Examples are ethynyl, 1-propynyl, 2-propynyl, 1-butynyl, 2-butynyl or 3-butynyl.

The term "alkoxy" as used herein denotes an unsubstituted unbranched or branched chain alkyloxy group wherein the "alkyl" portion is as defined above such as methoxy, ethoxy, n-propyloxy, i-propyloxy, n-butyloxy, i-butyloxy, t-butyloxy, pentyloxy, hexyloxy, heptyloxy including their isomers. "Lower alkoxy" as used herein denotes an alkoxy group with a "lower alkyl" group as previously defined.

The term "alkylthio" or "thioalkyl" as used herein denotes an unbranched or branched chain (alkyl)S-group wherein the "alkyl" portion is as defined above. Examples are methylthio, ethylthio, n-propylthio, i-propylthio, n-butylthio, i-butylthio or t-butylthio.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, and propyloxypentyl including their isomers.

The term "hydroxyalkyl" as used herein denotes an unbranched or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "heteroalkyl" as used herein means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, or alkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "heteroalkoxy" as used herein means an —O-(heteroalkyl) group wherein heteroalkyl is defined herein. "C$_{1-10}$ heteroalkoxy" as used herein refers to an —O-(heteroalkyl) wherein heteroalkyl is C$_{1-10}$. Representative examples include, but are not limited to, 2-dimethylaminoethoxy and 3-sulfonamido-1-propoxy.

The term "aryl" as used herein denotes an optionally substituted monocyclic or polycyclic-aromatic group comprising carbon and hydrogen atoms. Examples of suitable aryl groups include, but are not limited to, phenyl and naphthyl (e.g. 1-naphthyl or 2-naphthyl). Examples of suitable substituents for aryl include, but are limited to, alkyl, alkenyl, alkynyl, aryloxy, cycloalkyl, acyl, acylamino, alkoxy, amino, alkylamino, dialkylamino, halogen, haloalkyl, hydroxy, nitro and cyano. The term "(het)aryl" or "(hetero)aryl" refers to a denotes a moiety which can be either an aryl group or a heteroaryl group.

The term "arylheteroalkyl" as used herein denotes the radical R'R"— wherein R' is an aryl radical as defined herein, and R" is a heteroalkylene radical. A heteroalkylene radical is alkylene radical as defined herein wherein one, two or three hydrogen atoms have been replaced with a substituent independently selected from the group consisting of —OR$^a$, —NR$^b$R$^c$, and —S(O)$_n$R$^d$ wherein R$^a$-R$^d$ are as defined for the heteroalkyl group.

The term "sulfamide" as used herein refers to the sulfuric acid diamide, RRNSO$_2$NR'R' where R and R' are independently selected. Thus, Et-NH—SO$_2$—NH-Me would be designated N-ethyl-N'-methylsulfamide or 1-ethyl-3-methyl sulfamide.

The terms pyridinylmethyl and imidazolinylmethyl as used herein refer to substituents (i) and (ii), respectively.

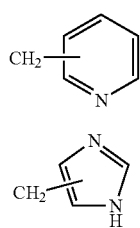

The term "isatoic anhydride" as used herein refers to a 3H-[1,3]oxazine-2,6-dione compound of formula (iii) wherein the 4 and 5 positions optionally are fused to an aryl or a heteroaryl ring.

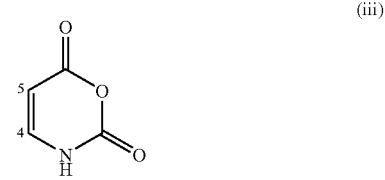

The term "arylalkyl" or "aralkyl" as used herein denotes the radical R'R"—, wherein R' is an aryl radical as defined herein, and R" is an alkylene radical as defined herein with the understanding that the attachment point of the arylalkyl moiety will be on the alkylene radical. Examples of arylalkyl radicals include, but are not limited to, benzyl, phenylethyl, 3-phenylpropyl.

The term "aryloxy" as used herein denotes an O-aryl group, wherein aryl is as defined above. An aryloxy group can be unsubstituted or substituted with one or two suitable substituents. The term "phenoxy" refers to an aryloxy group wherein the aryl moiety is a phenyl ring.

The term "aryl-alkoxy" as used herein denotes alkoxy group as defined herein wherein one hydrogen atom has been replaced with an optionally substituted aryl substituents where aryl is as defined herein.

The term "acyl" ("alkylcarbonyl") as used herein denotes a group of formula C(=O)R wherein R is hydrogen, unbranched or branched alkyl containing 1 to 7 carbon atoms or a phenyl group.

The term halogen stands for fluorine, chlorine, bromine or iodine, preferably fluorine, chlorine, bromine.

The term "combination" as used herein in reference in administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent includes peginterferon-α-2a (PEGASYS®) and peginterferon-α-2b (PEGINTRON®).

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomer usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇆ —C(—OH)=CH—), amide/imidic acid (—C(=O)—NH— ⇆ —C(—OH)=N—) and amidine (—C(=NR)—NH— ⇆ —C(—NHR)=N—) tautomers. The latter two are particularly common in heteroaryl and heterocyclic rings and the present invention encompasses all tautomeric forms of the compounds. The thiazine ring I is capable of existing as a tautomer Ia and the heterocyclic groups $A^1$-$A^6$ are capable of existing in a tautomeric keto form.

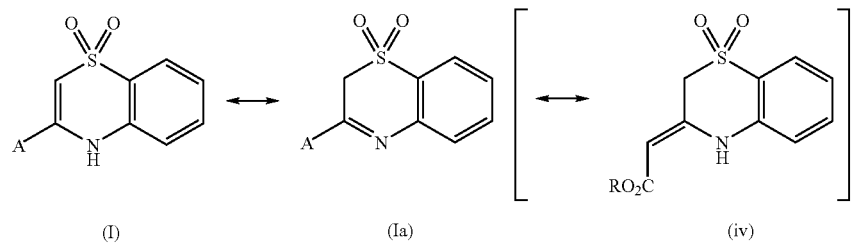

(I)　　　　　　(Ia)　　　　　　(iv)

Compounds of formula I wherein A is $CH_2CO_2R$ and R is alkyl can exist in an additional tautomeric form corresponding to (iv) and any reference to one of those tautomeric forms is made with the intent that any of the interconvertable tautomeric forms could be present.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e.g., channels) that have a guest molecule (e.g.), a solvent or water) trapped within.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), N-methyl-morpholine (NMM), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium dichromate (PDC), pyridinium chlorochromate (PCC), N,N'-dicyclohexylcarbodiimide (DCC), dichloromethane (DCM), propyl (Pr), diethyl azodicarboxylate (DEAD), phenyl (Ph), di-iso-propylazodicarboxylate (DIAD), pounds per square inch (psi), diethyl iso-propylamine (DIPEA), pyridine (pyr), di-iso-butylaluminumhydride (DIBAL-H), room temperature (rt or RT), N,N-dimethyl acetamide (DMA), tert-butyldimethylsilyl or t-BuMe$_2$Si (TBDMS), 4-N,N-dimethylaminopyridine (DMAP), triethylamine (Et$_3$N or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et$_2$O), trimethylsilyl or Me$_3$Si (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be recognized by one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and including, but not limited to mass spectrometry, nuclear magnetic resonance spectroscopy and infrared spectroscopy.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. One skilled in the art will be able to identify optimal reaction conditions for each transformation without undue experimentation.

While the following schemes often depict specific compounds; the reaction conditions are exemplary and can readily be adapted to other reactants. Alternative conditions also are well known. The reaction sequences in the following examples are not meant to limit the scope of the invention as set forth in the claims.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

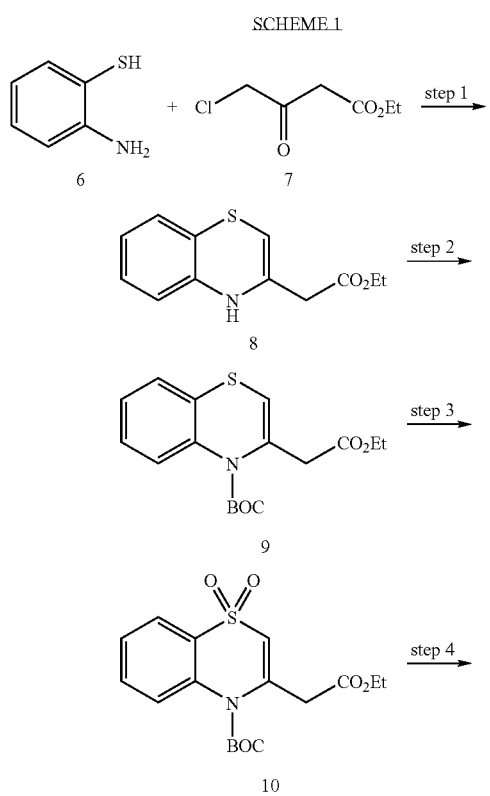

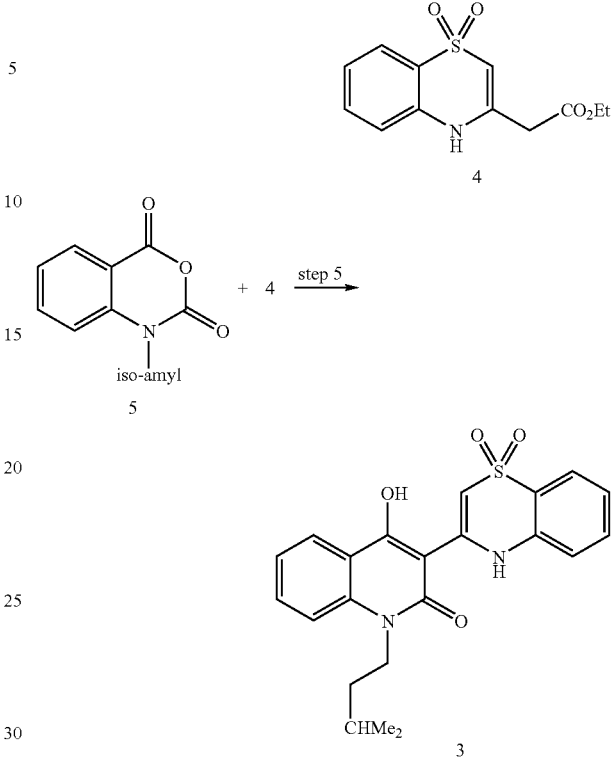

The preparation of 4-hydroxy-1-alkyl-3-aryl-1H-quinolin-2-ones by condensation of isatoic acid anhydrides with aryl acetic esters was reported by G. M. Coppola (*Synth. Commun.* 1985 15(2): 135-139). The 3-(1,1-dioxo-1,4-dihydro-benzo [1,4]thiazin-3-yl)-4-hydroxy-1H-quinolin-2-one compounds 3 (see TABLE 1) of the present invention were prepared by condensing an optionally substituted ethyl [1,1-dioxo-1,4-dihydro-2H-benzo[1,4]thiazin-(3E)-ylidene]-acetate 4 with an (optionally substituted) isatoic anhydride 5 as depicted in SCHEME 1. Esters other than ethyl esters can be used interchangeably in the depicted schemes. Ethyl (1,1-dioxo-1,4-dihydro-benzo[1,4]thiazin-3-yl)-acetate 4 was prepared by alkylation and cyclization of 2-aminothiophenol (6) and ethyl 3-chloroacetoacetate (7) to afford ethyl [4H-benzo[1,4]thiazin-(3E)-ylidene]-acetate (8). The alkylation of thiols and amines is optionally carried out in a solvent or mixture of solvents such as DCM, DMF, PhH, toluene, chlorobenzene, THF, PhH/THF, dioxane, MeCN or sulfolane with an alkylating agent such as an alkyl 3-chloroacetoacetate, optionally in the presence of a tertiary organic base or in the presence of an inorganic base, conveniently at temperatures between 0 and 150° C., preferably at temperatures between 0 and 100° C. Cyclization of the intermediate aminoketone cyclizes to affords 8. Protection of the amine (8→9), oxidation of the sulfide to the corresponding sulfone (9→10) and deprotection (10→11) utilizing standard protocols affords 4. Ortho-aminothiopyridines (M. H. Norman et al., *J. Med. Chem.* 1996, 39(24):4692-4703) afford the corresponding compounds in which the thiazine is fused to a pyridine moiety. Examples of 2-amino-thiophene-3-thiols are depicted in Examples 20 and 21.

N-substituted isatoic anhydrides are available by alkylation of isatoic anhydride or by cyclization of an N-substituted anthranilic acid with phosgene or a phosgene equivalent.

N-substituted anthranilic acids can be prepared by displacement or coupling of 2-chlorobenzoic acid with amines or by reductive amination of anthranilic acid (G. E. Hardtmann et al., *J. Heterocyclic Chem.* 1975 12:565). Aryl substituted isatoic acids are commercially available or can be prepared from substituted anthranilic acid derivatives. 1H-Pyrido[2,3-d][1,3]oxazine-2,4-diones useful for the preparation of compounds of formula I-A-1 where X is nitrogen can be prepared by known procedures (see, e.g., G. M. Coppola et al., *J. Het. Chem.* 1985 22:193-206, or D. J. LaCount and D. J. Dewsbury, *Synthesis* 1982 972).

Some embodiments of the present invention are substituted on the benzo[1,4]thiazinyl radical. Example 7 provides a method for introducing a nitrogen-containing functional group onto the 5, 6, 7 or 8 positions of the ortho-phenylene moiety. The synthetic steps parallel those depicted in SCHEME 1 to which is added a step that introduces of 4-nitro substituent. One skilled in the art will appreciate that substituted 2-amino-benzenethiols are available from a variety of precursors which are useful for the preparation of compounds of the present invention.

Ethyl (7-Nitro-1,1-dioxo-1,4-dihydro-1$\lambda^6$-benzo[1,4]thiazin-3-yl)-acetic acid (27d) is a particularly versatile synthetic intermediate which can be prepared from 27a (example 7) via a three-step sequence comprising protection of the secondary amino contained in the thiazine ring, oxidation od the sulfur atom and deprotection of the resulting sulfone. Examples of this sequence are described in steps 2-4 of example 1.

There is considerable flexibility in the sequence of steps used to prepare compounds of the present invention. For example, the sequence depicted in example 7 introduces an amino-methylsulfonamide substituent prior to formation of the linkage between the thiazine and the hydroxyquinolone rings. The linkage can also be introduced with thiazine 27d to afford a nitro substituted compound which is a versatile advance intermediate for the production of compounds of the present invention by reduction of the nitro group and further elaboration of the resulting amine (e.g. alkylation, acylation, sulfonylation and Michael addition, see, e.g. example 20).

Similarly, example 6 illustrates the preparation of a 7-hydroxy compound of the present invention. This sequence embarks from a simple substituted aniline and introduces the requisite thiol via a 2-chloro-2$\lambda^4$-benzo[1,2,3]dithiazole 19 which is fragmented under basic reductive conditions to afford the ortho-amino thiol which is cyclized without further isolation. The reaction similarly affords a general route for introduction of one or more substituents onto the 1,1-dioxo-1,4-dihydro-1$\lambda^6$-benzo[1,4]thiazin-3-yl fragment. Further elaboration of the hydroxy group by alkylation of the oxygen atom affords other compounds of the present invention.

TABLE 1

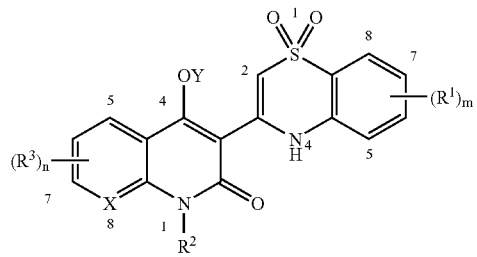

(I-A-1)

| No. | $R^1$ | $R^2$ | $R^3$ | X | Y | ms | mp |
|---|---|---|---|---|---|---|---|
| I-1 | H | iso-amyl | H | CH | H | 410.49 | 411 |
| I-2 | | —(CH$_2$)$_2$-c-C$_3$H$_5$ | 6-F | CH | H | 426.47 | 427 | 188-189 |
| I-3 | H | iso-amyl | 6-Cl | CH | H | 444.94 | 445 | 194-197 |
| I-4 | H | —(CH$_2$)$_2$-c-C$_3$H$_5$ | 6-Me | CH | H | 422.50 | 421 (M − H) | 93-103 |
| I-5 | H | —(CH$_2$)$_2$-c-C$_3$H$_5$ | 6-OMe | CH | H | 438.50 | 439 (MH) | 220-221 |
| I-6 | H | —(CH$_2$)$_2$-c-C$_3$H$_5$ | 6-Cl | CH | H | 442.92 | 441 (M − H) | 227-229 |
| I-7 | 6-Cl | iso-amyl | H | CH | H | 444.94 | 443 (M − H) | 90-110 |
| I-8 | H | —CH$_2$-o-C$_6$H$_4$F | H | CH | H | 448.47 | 449 (MH) | >200 |
| I-9 | H | —CH$_2$-p-C$_6$H$_4$F | H | CH | H | 448.47 | 447 (M − H) | 237-238 |
| I-9a | H | —CH$_2$-p-C$_6$H$_4$F | H | CH | Na | 470.46 | 447 (M − H) | >250 |
| I-10 | H | —(CH$_2$)$_2$-c-C$_3$H$_5$ | H | N | H | 409.46 | 410 (MH) | |
| I-11 | H | iso-amyl | H | N | H | 411.48 | 410 (M − H) | |
| I-12 | H | iso-amyl | 6-F | N | H | 429.47 | 430 (MH) | 90-112 |
| I-13 | H | —CH$_2$-p-C$_6$H$_4$F | 6-F | CH | H | 466.46 | 465 (M − H) | 233-2354 |
| I-13a | H | —CH$_2$-p-C$_6$H$_4$F | 6-F | CH | Na | 488.45 | 465 (M − H) | >250 |
| I-14 | H | —CH$_2$-p-C$_6$H$_4$F | 6-Me | CH | H | 462.50 | 461 (M − H) | 247-249 |
| I-14a | H | —CH$_2$-p-C$_6$H$_4$F | 6-Me | CH | Na | 484.48 | 461 (M − H) | >250 |
| I-15 | 7-NO$_2$ | —(CH$_2$)$_2$-c-C$_3$H$_5$ | 6-F | CH | H | 471.63 | | |
| I-16 | 6-CN | iso-amyl | H | CH | H | 435.50 | 434 (M − H) | >250 |
| I-17 | 6-CH$_2$NH$_2$ | iso-amyl | H | CH | H | 439.53 | 440 (MH) | |
| I-18 | 7-OH | —CH$_2$-p-C$_6$H$_4$F | 6-F | CH | H | 482.46 | 481 (M − H) | 185[1] |
| I-19 | 7-OBn | —CH$_2$-p-C$_6$H$_4$F | 6-F | CH | H | 572.59 | 571 (M − H) | 242-244 |
| I-20 | 7-OCH$_2$CONH$_2$ | —CH$_2$-p-C$_6$H$_4$F | 6-F | CH | H | 539.52 | 538 (M − H) | 145[1] |
| I-21 | 7-NH$_2$ | —(CH$_2$)$_2$-c-C$_3$H$_5$ | H | CH | H | 423.49 | 424 (MH) | >250 |
| I-22 | 7-NH$_2$ | —CH$_2$-p-C$_6$H$_4$F | 6-F | CH | H | 481.48 | 480 (M − H) | >250 |
| I-23 | 7-NHAc | —CH$_2$-p-C$_6$H$_4$F | 6-F | CH | H | 523.52 | 522 (M − H) | >250 |
| I-24 | 7-NHSO$_2$Me | —CH$_2$-p-C$_6$H$_4$F | 6-F | CH | H | 559.57 | 558 (M − H) | >250 |
| I-24a | 7-NHSO$_2$Me | —CH$_2$-p-C$_6$H$_4$F | 6-F | CH | Na | 581.55 | 558 (M − H) | >250 |
| I-25 | H | 3,4-di-F—C$_6$H$_3$CH$_2$ | 6-F | CH | H | 484.46 | 483 (M − H) | 230-235 |
| I-25a | H | 3,4-di-F—C$_6$H$_3$CH$_2$ | 6-F | CH | Na | 506.44 | 483 (M − H) | 230-235 |

TABLE 1-continued

| | | | | | | | | |
|---|---|---|---|---|---|---|---|---|
| I-26 | H | 3-Me-4-F—C₆H₃CH₂ | 6-F | CH | H | 480.49 | 479 (M − H) | 225-230 |
| I-26a | H | 3-Me-4-F—C₆H₃CH₂ | 6-F | CH | Na | 502.49 | 479 (M − H) | >250 |
| I-27 | H | 3-CN—C₆H₄CH₂ | 6-F | CH | H | 473.48 | 474 (MH) | >250 |
| I-27a | H | 3-CN—C₆H₄CH₂ | 6-F | CH | Na | 495.47 | 474 (MH) | >250 |
| I-28 | 7-NHSO₂Me | —(CH₂)₂-c-C₃H₅ | 6-F | CH | H | 519.57 | 520 (MH) | |
| I-28a | 7-NHSO₂Me | —(CH₂)₂-c-C₃H₅ | 6-F | CH | Na | 541.56 | 520 (MH) | >250 |
| I-29 | 7-NHSO₂-n-Pr | —(CH₂)₂-c-C₃H₅ | 6-F | CH | H | 547.63 | 548 (MH) | 145-150 |
| I-29a | 7-NHSO₂-n-Pr | —(CH₂)₂-c-C₃H₅ | 6-F | CH | Na | 569.61 | 548 (MH) | >250 |
| I-30 | 7-OMe | —CH₂-p-C₆H₄F | 6-F | CH | H | 496.49 | 497 (M − H) | >250 |
| I-31 | 7-OCH₂CO₂Me | —CH₂-p-C₆H₄F | 6-F | CH | H | 554.53 | 555 (MH) | 200-207 |
| I-32 | 7-NHSO₂Et | —(CH₂)₂-c-C₃H₅ | 6-F | CH | H | 533.60 | 534 (MH) | 140-142 |
| I-33 | 7-NHSO₂-c-C₃H₅ | —(CH₂)₂-c-C₃H₅ | 6-F | CH | H | 545.61 | 546 (MH) | 145-155 |
| I-34 | 7-OCH₂CONMe₂ | —CH₂-p-C₆H₄F | 6-F | CH | H | 567.57 | 566 (M − H) | >250 |
| I-35 | 7-N(Me)SO₂Me | —(CH₂)₂-c-C₃H₅ | 6-F | CH | H | 533.60 | | 208-212 |
| I-36 | 7-NH—SO₂-(3,5-diMe-isoxazol-4-yl) | —(CH₂)₂-c-C₃H₅ | 6-F | CH | H | 600.65 | | 150-157 |
| I-37 | 7-NHSO₂Ph | —(CH₂)₂-c-C₃H₅ | 6-F | CH | H | 581.64 | 582 (MH) | >200 |
| I-38 | 7-NHC(=O)NHMe | —(CH₂)₂-c-C₃H₅ | 6-F | CH | H | 498.33 | 499 (MH) | >220 |
| I-39 | 7-O(CH₂)₂CONH₂ | —(CH₂)₂-c-C₃H₅ | 6-F | CH | H | 513.54 | 514 (MH) | >250 |
| I-40 | 7-NHSO₂NH₂ | —(CH₂)₂-c-C₃H₅ | 6-F | CH | H | 520.56 | 519 (M − H) | 183-186 |
| I-42 | 7-OCH₂CONHMe | —CH₂-p-C₆H₄F | 6-F | CH | H | 553.54 | 552 (M − H) | >240 |
| I-43 | 7-NHSO₂Et | —CH₂-p-C₆H₄F | 6-F | CH | H | 573.61 | 572 (M − H) | |
| I-44 | 7-NHSO₂Me | Me | H | CH | H | 447.49 | 448 (MH) | |
| I-45 | 7-NHSO₂Me | —CH₂-p-C₆H₄F | 6-Me | CH | H | 555.01 | 556 (MH) | |
| I-46 | 7-NHSO₂-n-C₃H₉ | —CH₂-p-C₆H₄F | 6-F | CH | H | 587.62 | 588 (MH) | |
| I-47 | 7-N(Me)SO₂Me | —CH₂-p-C₆H₄F | 6-F | CH | H | 573.6 | | 214-218 |
| I-48 | 7-NHSO₂Me | CH₂—(4-F-3-Me—C₆H₃) | 6-F | CH | H | 573.6 | | 201-217 |
| I-49 | 7-NHSO₂Me | CH₂—(4-F-3-Cl—C₆H₃) | 6-F | CH | H | 594.01 | | 166-174 |
| I-50 | 7-NHSO₂Me | pyrid-3-ylmethyl | 6-F | CH | H | 542.57 | | 174-186 |
| I-51 | 7-NHSO₂Me | —CH₂-c-C₆H₁₁ | 6-F | CH | H | 547.63 | | 184-203 |
| I-52 | 7-NHSO₂Me | isoamyl | 6-F | CH | H | 521.59 | | 205-219 |
| I-53 | 7-NHSO₂-c-C₃H₅ | CH₂-p-C₆H₄F | 6-F | CH | H | 585.61 | 584 (M − H) | |
| I-54 | 7-NHSO₂Me | CH₂—(3,4-di-F—C₆H₃) | 6-F | CH | H | 577.56 | | 148.2-149.4 |
| I-55 | 7-NHSO₂Me | CH₂—(4-F-3-CF₃—C₆H₃) | 6-F | CH | H | 627.57 | | 185.8-187 |
| I-56 | 7-NHSO₂CH₂Ph | CH₂-p-C₆H₄F | 6-F | CH | H | 635.67 | 634 (M − H) | |
| I-57 | 7-NH—SO₂-N(oxazolidin-2-one) | CH₂-p-C₆H₄F | | | | 630.6 | 629 (M − H) | |
| I-58 | 7-NHSO₂Me | CH₂-p-C₆H₄F | 6-OMe | CH | H | 571.6 | 570 (M − H) | |
| I-59 | 7-NHSO₂Me | CH₂-p-C₆H₄F | 6-Cl | CH | H | 576.02 | 574 (M − H) | |
| I-60 | 7-NHSO₂-i-Pr | CH₂-p-C₆H₄F | 6-F | CH | H | 587.62 | 586 (M − H) | |
| I-61 | 7-NHSO₂-n-C₄H₉ | CH₂-p-C₆H₄F | 6-F | CH | H | 601.65 | 600 (M − H) | |
| I-62 | 7-NHSO₂NMe₂ | CH₂-p-C₆H₄F | 6-F | CH | H | 588.61 | 587 (M − H) | |
| I-63 | 7-NHSO₂NH-Boc | CH₂-p-C₆H₄F | 6-F | CH | H | 660.67 | 659 (M − H) | |
| I-64 | 7-NHSO₂NH₂ | CH₂-p-C₆H₄F | 6-F | CH | H | 560.56 | 559 (M − H) | |
| I-65 | 7-NH—SO₂-N(pyrrolidinyl) | CH₂-p-C₆H₄F | 6-F | CH | H | 614.65 | 613 (M − H) | |
| I-66[2] | 7-NHSO₂Me | pyridin-4-yl-methyl | 6-F | CH | H | 542.47 | 543 (M + H) | 167-169 |
| I-67 | 7-NHSO₂Me | CH₂-p-C₆H₄F | 7-Cl | CH | H | 576.03 | 576 (M − H) 574 (M − H) | — |
| I-68 | 7-CH₂OMe | CH₂-p-C₆H₄F | 6-F | CH | H | 510.52 | 509 (M − H) | |
| I-69 | 7-NHSO₂Me | CH₂-p-C₆H₄F | 6,7-di-F | CH | H | 577.56 | 576 (M − H) | |
| I-70 | 7-NHSO₂Me | pyridin-2-yl-methyl | 6-F | CH | H | 542.57 | | 172-215 |
| I-71 | 7-NH₂ | CH₂—(4-F-3-Me—C₆H₃) | 6-Cl | CH | H | 511.96 | 512 (M + H) 510 (M − H) | |
| I-72 | 7-Br | CH₂-p-C₆H₄F | 7_F | CH | H | 545.36 | 543 & 545 (M − H) | |

TABLE 1-continued

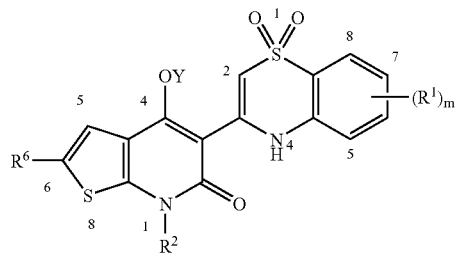

(I-A-7)

| No. | $R^1$ | $R^2$ | $R^6$ | Y | mw | ms | mp |
|---|---|---|---|---|---|---|---|
| I-73 | 7-NH$_2$ | CH$_2$-p-C$_6$H$_4$F | Me | — | H | 483.54 | 484 (M + H) |
| I-74 | 7-NHSO$_2$Me | CH$_2$-p-C$_6$H$_4$F | Me | — | H | 561.64 | 562 (M + H) |
| I-75 | 7-NHSO$_2$Me | CH$_2$-p-C$_6$H$_4$F | H | — | H | 547.61 | 546 (M − H) |
| I-76 | 7-NHSO$_2$Me | CH$_2$-p-C$_6$H$_4$F | Et | — | H | 575.66 | 576 (M + H) |

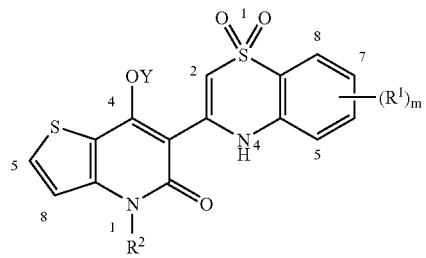

(I-A-8)

| No. | $R^1$ | $R^2$ | Y | mw | ms | mp |
|---|---|---|---|---|---|---|
| I-77 | 7-NHSO$_2$Me | CH$_2$-p-C$_6$H$_4$F | H | 547.61 | 548 (M + H) | |

[1] decomposition
[2] TFA salt

4-Hydroxy-1,5-dihydro-pyrrol-2-ones (I-A-3; TABLE 2) of the present invention can be prepared by base-catalyzed intramolecular cyclization of 2-(alkyl-(hetero)aryl-acetylamino)-alkanoic esters. The cyclization has been utilized for the solid phase synthesis of tetramic acids (J. Matthews and R. A. Rivero, *J. Org. Chem.* 1998 63(14):4808-4810). Amides 12 were prepared by condensation of either 4a or 4b with an N-substituted α-amino acid ester. One skilled in the art will appreciate that amino acids with a diverse substitution at the α-position are very accessible and can be used to prepare compounds within the scope of the present invention.

SCHEME 2

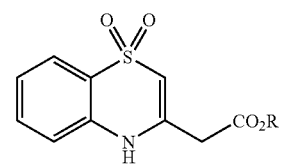

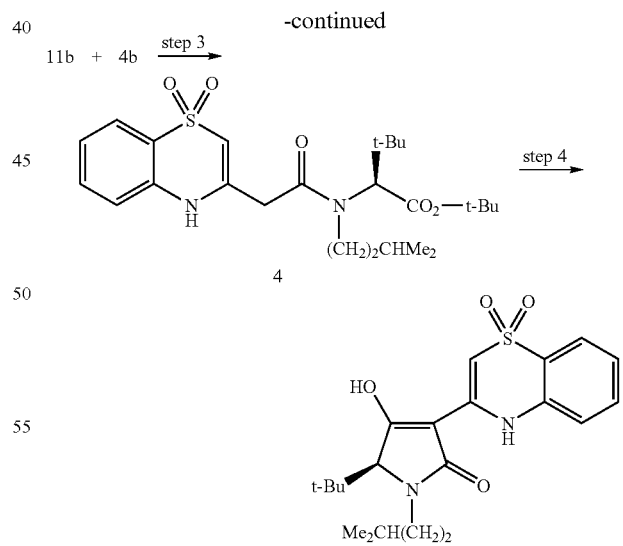

Acylation of 11b is carried out by standard methodology. Such acylations are conveniently carried out with a corresponding acyl halide or acid anhydride in a solvent such as methylene chloride, chloroform, carbon tetrachloride, ether, THF, dioxane, benzene, toluene, MeCN, DMF, aqueous sodium hydroxide solution or sulfolane optionally in the presence of an inorganic or organic base at temperatures between −20 and 200° C., but preferably at temperatures between −10 and 160° C. Typical organic bases, e.g., tertiary amines, include but are not limited to TEA, pyridine. Typical inorganic bases include but are not limited to $K_2CO_3$ and $NaHCO_3$.

The acylation may however also be carried out with the free acid optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, DCC, DCC/HOBt or HOBt, N,N'-carbonyldiimidazole, O-(benzotriazol-1-yl)-N,N,N',N'-tetramethyl-uronium tetrafluoroborate/NMM, O-(benzotriazol-1-yl)-N,N,N',N'-tetramethyl-uronium tetrafluoroborate/DIPEA, N,N'-thionyldiimidazole or $Ph_3P/CCl_4$, at temperatures between −20 and 200° C., but preferably at temperatures between −10 and 160° C.

The N-substituent on the pyrrolidone ring can be introduced by alkylation or reductive alkylation. These processes afford significant flexibility in the selection and introduction of an N-substituent. Reductive amination is preferably carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7 optionally in the presence of a dehydrating agent, such as molecular sieve or $Ti(IV)(O-i-Pr)_4$ to facilitate formation of the intermediate imine at ambient temperature. Alternatively, formation of the imine in the presence of hydrogen and a hydrogenation catalyst, e.g. in the presence of palladium/charcoal, at a hydrogen pressure of 1 to 5 bar, preferably at temperatures between 20° C. and the boiling temperature of the solvent used. It may also be advantageous to protect reactive groups during the reaction using conventional protecting groups which are cleaved again by conventional methods after the reaction. Reductive amination procedures have been reviewed: R. M. Hutchings and M. K. Hutchings *Reduction of C=N to CHNH by Metal Hydrides in Comprehensive Organic Synthesis* col. 8, I. Fleming (Ed) Pergamon, Oxford 1991 pp. 47-54.

Sodium tert-butoxide induced intramolecular cyclization of 12 affords the 4-hydroxy-1-(3-methyl-butyl)-1,5-dihydro-pyrrol-2-one (13). While the cyclization is herein exemplified with sodium tert-butoxide, a variety of strong bases including potassium tert-butoxide, lithium diisopropyl amide (and other lithium dialkylamides), lithium hexamethyldisilazane and sodium hydride could be used interchangeably. The reaction is commonly carried out in ethereal solvents such as THF, dioxane or DME. Sodium or potassium alkoxides in alcoholic solvents can also be used in the cyclization. The reaction can be accomplished between −70 and 60° C.

TABLE 2

(I-A-3)

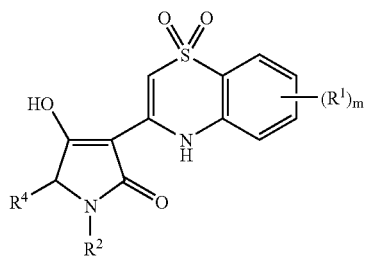

| Cpd. No | $R^1$ | $R^2$ | $R^4$ | mw | ms | mp |
|---|---|---|---|---|---|---|
| II-1 | H | $(CH_2)_2CMe_2$ | t-Bu | 404.53 | 405 (MH) | 85-87 |
| II-2 | H | $(CH_2)_2CMe_2$ | c-$C_6H_{11}$ | 430.57 | 429 (M − H) | 98-100 |
| II-3 | H | $(CH_2)_2CMe_2$ | CHMe(Et) | 404.53 | 403 (M − H) | 72-80 |
| II-4 | H | $CH_2Ph$ | CHMe(Et) | 424.52 | 423 (M − H) | 88-95 |
| II-5 | H | —$CH_2$-p-$C_6H_4F$ | $CH_2CHMe_2$ | 442.51 | | 160 (d) |
| II-6 | H | —$CH_2$-p-$C_6H_4F$ | -c-$C_6H_{11}$ | 468.55 | 467 (M − H) | 180 (d) |
| II-7[1] | H | —$CH_2$-p-$C_6H_4F$ | -c-$C_6H_{11}$ | 468.55 | | >250 |
| II-8 | 7-$NHSO_2Me$ | —$CH_2$-p-$C_6H_4F$ | t-Bu | 535.61 | 534 (M − H) | 165-172 |
| II-9 | 7-$NHSO_2Me$ | 4-F-3-Me-$C_6H_3CH_2$— | t-Bu | 549.64 | 548 (M − H) | 173-176 |
| II-10 | 7-$NHSO_2Me$ | 4-F-3-MeO—$C_6H_3CH_2$— | t-Bu | 565.64 | 564 (M − H) | 175-180 |
| II-11 | 7-$NHSO_2Me$ | 4-F-3-Cl—$C_6H_3CH_2$— | t-Bu | 570.06 | | 165-170 |
| II-12 | 7-$NO_2$ | —$CH_2$-p-$C_6H_4F$ | t-Bu | 487.51 | | 138-147 |
| II-13 | 7-$NH_2$ | —$CH_2$-p-$C_6H_4F$ | t-Bu | 457.52 | | 146-155 |
| II-14 | 7-$NHSO_2NH_2$ | —$CH_2$-p-$C_6H_4F$ | t-Bu | 536.60 | | 150-156 |
| II-15 | 7-$NH_2$ | —$(CH_2)_2$-c-$C_3H_5$ | t-Bu | 417.53 | | 105-110 |
| II-16 | 7-$NHSO_2Me$ | —$(CH_2)_2$-c-$C_3H_5$ | t-Bu | 495.62 | | 140-145 |

TABLE 2-continued

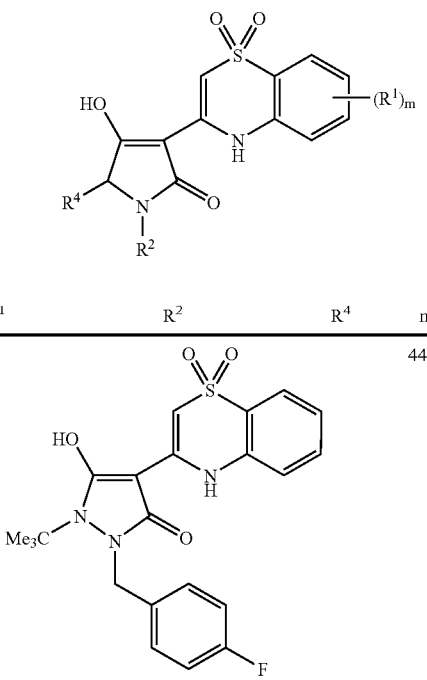

(I-A-3)

| Cpd. No | R¹ | R² | R⁴ | mw | ms | mp |
|---|---|---|---|---|---|---|
| II-17 | | | | 443.49 | | |

Pyridone compounds (15, TABLE 3) of the present invention are prepared by condensation of 24 with a 1,3-oxazine-2,5-diones 14 in analogy with the preparation of 4-hydroxy-1-alkyl-3-aryl-1H-quinolin-2-ones starting with an isatoic acid anhydrides. The synthesis of oxazinediones has been described by E. M. Beccalli et al. *J. Org. Chem.* 1987 52(15): 3426-3434; *Tetrahedron Lett.* 1986 27(5):627-630 and by J. H. MacMillan and S. S. Washburn *J. Het. Chem.* 1975 12:1215-1220.

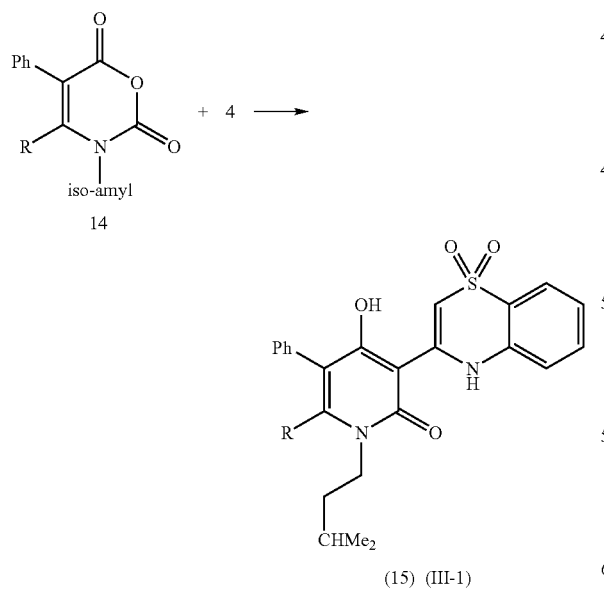

TABLE 3

(I-A-2)

| Cpd. No. | R¹ | R² | R³ | R⁵ | mw | ms | mp |
|---|---|---|---|---|---|---|---|
| III-1 | H | (CH₂)₂CMe₂ | H | Me | 450.56 | 449 (M − H) | 118-121 |

Isoquinoline compounds (TABLE 4) of the present invention are prepared as depicted in SCHEME 3. The key step in the preparation is the condensation of a deprotonated ortho-substituted methylsulfonyl aniline 34 and an alkyl-(4-(ar)alkyl)-4-methoxyisoquinoline-3-carboxylate 33 and subsequent intermolecular condensation of the resulting amino ketone to afford the 4H-benzo[1,4]thiazine 1,1-dioxide ring. Deprotonation of the sulfone is accomplished with an alkyl lithium in an non-protic solvent. Etheral solvents such as THF, diethyl ether, DME and dioxane are commonly used for this purpose; however, other solvents with in which the lithiated sulfone is soluble and which do not react with the alkyl lithium can be used interchangeably. In addition to alkyl lithium, non-nucleophilic dialkyl amide bases, e.g., lithium diisopropylamide and lithium hexamethyl disilazane, sodium and potassium hydride also can be used.

SCHEME 3

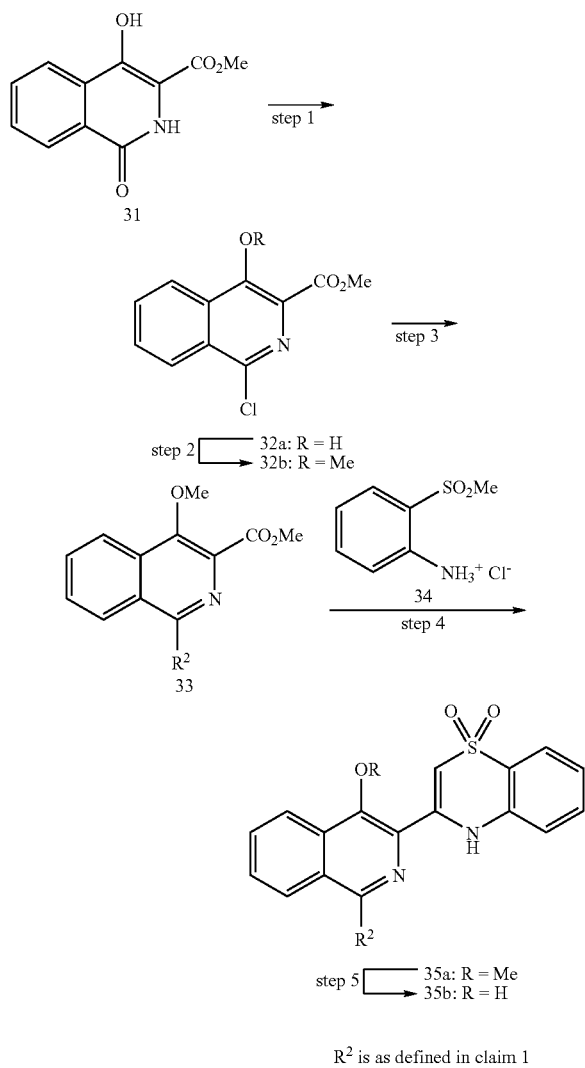

step 5 ⎡ 35a: R = Me
       ⎣ 35b: R = H

R² is as defined in claim 1

The requisite alkyl-(4-(ar)alkyl)-4-methoxyisoquinoline-3-carboxylate precursors can be prepared from an appropriately substituted 4-hydroxy-3-carbomethoxy-1(2H)-isoquinolone (31). The isoquinolones can be prepared by the Gabriel-Colman rearrangement of phthalimidoacetic acids (Gabriel and Colman, Chem Ber. 1902 35:2421; L. R. Caswell and P. C. Atkinson; J. Heterocyclic Chem. 1966 3:328-332; W. Gensler, Isoquinoline in Heterocyclic Compounds, R. C. Elderfield, ed. John Wiley & Sons, NY 1952, pp. 376-379). Chlorination of the 1-oxo-1,2-dihydro-isoquinoline moiety is readily accomplished with POCl₃ or PCl₅. Protection of the phenol as an alkyl ether is readily accomplished by treating the phenol with an alkylating agent in the presence of a basic capable of deprotonating the phenol. Alkyl halides, dialkyl sulfates and sulfonate esters of alcohols are commonly used alkylating agents while alkali metal salts, e.g., K₂CO₃, Na₂CO₃ or Cs₂CO₃, alkali metal alkoxides or hydrides are convenient bases. Deprotection of the methyl ether was achieved with boron tribromide in CH₂Cl₂ maintained at 0° C. Numerous alternative protecting groups and protocols for alkylation and dealkylation are known in the art and can be employed to prepare compounds of the present invention. Reagents and protocols for deprotection are described in T. W. Greene and P. G. M. Wuts, Protective Groups in Organic Synthesis, Wiley & Sons, New York 1999.

Introduction of the substiuent at the 1-position (SCHEME 3; step 3) was accomplished utilizing a palladium-catalyzed coupling. The Negishi coupling of organozinc halides or dialkylzinc with haloarenes and aryl triflates is an effective means for attachment of an alkyl group to an arene. The reaction is catalyzed by palladium Pd(0) and palladium is preferably ligated to a bidentate ligand including Pd(dppf)Cl₂ and Pd(dppe)Cl₂. (J. M. Herbert Tetrahedron Lett. 2004 45:817-819). Typically the reaction is run an inert aprotic solvent and common ethereal solvents include dioxane, DME and THF are suitable. The reaction is commonly run at elevated temperature.

TABLE 4

(I-A-5)

| | R¹ | R³ | R² | R⁶ | mw | mp | ms |
|---|---|---|---|---|---|---|---|
| IV-1 | H | H | —CH₂-p-C₆H₄F | H | 432.47 | 267-269 | |
| IV-2 | H | H | —CH₂-p-C₆H₄F | Me | 446.5 | 115-120 | |
| IV-3 | Cl | H | —CH₂-p-C₆H₄F | Me | 480.94 | >275 | |
| IV-4 | Cl | F | —CH₂-p-C₆H₄F | Me | 498.94 | 254-256 | |

Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Examples of the preparation and testing of representative compounds encompassed by the present invention and within the scope of the invention are provided in the following examples. These examples and preparations which follow are provided to enable those skilled in the art to more clearly understand and to practice the present invention. They should not be considered as limiting the scope of the invention, but merely as being illustrative and representative thereof.

EXAMPLE 1

3-(1,1-Dioxo-1,4-dihydro-1λ⁶-benzo[1,4]thiazin-3-yl)-4-hydroxy-1-(3-methyl-butyl)-1H-quinolin-2-one (I-1, SCHEME 1)

step 1—To a solution of 2-aminothiophenol (4.96 g, 39.6 mmol) in MeOH (200 mL) was added the ethyl 4-chloroacetoacetate (6.2 g, 38 mmol). After stirring at room temperature for 2 h the MeOH was removed under reduced pressure. The residue was dissolved in Et$_2$O and washed with HCl (1N), saturated NaHCO$_3$, and brine. The organic phase was dried over MgSO$_4$, filtered and the solvent was removed under reduced pressure. The product was obtained from a minimum of EtOH to afford 5.0 g (54%) of 8: LCMS RT 3.7 min, M+H.

step 2—To a solution of 8 (1.0 g, 4.3 mmol) in THF (50 mL) was added the di-tert-butyl dicarbonate (1.86 g, 8.5 mmol) and DMAP (1.0 g, 8.5 mmol). After stirring at rt for 1 h, the solvent was removed under reduced pressure. The residue was dissolved in DCM and washed with 1N HCl. The organic phase was concentrated and the product was purified by column chromatography on SiO$_2$ eluting with EtOAc/hexanes to afford 1.4 g (985) of 9: LCMS RT 3.7 min, M+H.

step 3—The BOC protected thiazine 9 (1.4 g, 4.2 mmol) was dissolved in DCM (50 mL) and MCPBA (4.8 g, 21 mmol) was added. This mixture was stirred vigorously for 1 h at rt. An aqueous solution of sodium thiosulfate (1 eq) was added and stirring continued for 15 minutes. The organics were separated and washed with NaOH (1N), HCl (1N), saturated NaHCO$_3$, and brine. The organics were dried over MgSO$_4$, filtered and the solvent was removed under reduced pressure to afford 1.3 g of 10: LCMS RT 3.27 min, M+H$_2$O.

step 4—A solution of the BOC thiazine-1,1-dioxide 10 (1 g, 2.7 mmol) and 50% TFA/DCM was stirred for 18 h and the TFA was removed under reduced pressure. The residue was dissolved in ethyl acetate and washed sequentially with saturated NaHCO$_3$ and brine. The organics were dried over MgSO$_4$, filtered and the solvent was removed under reduced pressure to afford 0.7 g (97%) of 4: LCMS RT 2.07 min, M+H.

step 5—The thiazine 4 (0.20 g, 0.75 mmol) and 1-isoamyl isatoic anhydride (5, 0.17 g, 0.75 mmol) were dissolved in EtOAc (2 ml) and THF (2 mL). To this mixture was added DBU (0.23 g, 1.5 mmol). The reaction mixture was heated at reflux for 30 minutes. After cooling to rt, acetic acid (1 mL), 1N HCl (5 mL) and water were added sequentially and the product was extracted into EtOAc. The organics were washed with saturated NaHCO$_3$ and brine. The organic phase was dried over MgSO$_4$, filtered and the solvent was removed under reduced pressure. The product was purified by column chromatography on SiO$_2$ eluting with EtOAc/hexanes to afford 0.08 g (26%) of I-1: LCMS RT 3.86 min, M+H.

Using the same procedure but replacing 1-isoamyl-isatoic anhydride with 1-(2-cyclopropylethyl)-6-fluoro-isoatoic anhydride in the final step there was obtained 0.032 g (9%) of 1-(2-cyclopropyl-ethyl)-3-(1,1-dioxo-1,4-dihydro-1λ⁶-benzo[1,4]thiazin-3-yl)-6-fluoro-4-hydroxy-1H-quinolin-2-one (I-2): LCMS RT 3.69 min, M+H.

Using the same procedure but replacing 1-isoamyl-isatoic anhydride with 1-isoamyl-6-chloro-isoatoic anhydride in the final step there was obtained 0.104 g (31%) of 1-isoamyl-3-(1,1-dioxo-1,4-dihydro-1λ⁶-benzo[1,4]thiazin-3-yl)-6-chloro-4-hydroxy-1H-quinolin-2-one (I-3): LCMS RT 4.13 min, M+H.

Using the same procedure but replacing 1-isoamyl-isatoic anhydride with 1-(2-cyclopropylethyl)-6-methyl-isoatoic anhydride in the final step there was obtained 0.040 g (36%) of 1-(2-cyclopropyl-ethyl)-3-(1,1-dioxo-1,4-dihydro-1λ⁶-benzo[1,4]thiazin-3-yl)-6-methyl-4-hydroxy-1H-quinolin-2-one (I-4): LCMS RT 2.90 min, M–H.

Using the same procedure but replacing 1-isoamyl-isatoic anhydride with 1-(2-cyclopropylethyl)-6-methoxy-isoatoic anhydride in the final step there was obtained 0.055 g (22%) of 1-(2-cyclopropyl-ethyl)-3-(1,1-dioxo-1,4-dihydro-1λ⁶-benzo[1,4]thiazin-3-yl)-6-methoxy-4-hydroxy-1H-quinolin-2-one (I-5): LCMS RT 3.61 min, M+H.

Using the same procedure but replacing 1-isoamyl-isatoic anhydride with 1-(2-cyclopropylethyl)-6-chloro-isoatoic anhydride in the final step there was obtained 0.028 g (6%) of 1-(2-cyclopropyl-ethyl)-3-(1,1-dioxo-1,4-dihydro-1λ⁶-benzo[1,4]thiazin-3-yl)-6-chloro-4-hydroxy-1H-quinolin-2-one (I-6): LCMS RT 2.67 min, M–H.

Using the same procedure but replacing 1-isoamyl-isatoic anhydride with 1-(2-fluorobenzyl)-6-isoatoic anhydride in the final step there was obtained 0.070 g (17%) of 3-(1,1-dioxo-1,4-dihydro-1λ⁶-benzo[1,4]thiazin-3-yl)-1-(2-fluorobenzyl)-4-hydroxy-1H-quinolin-2-one (I-8): LCMS RT 2.49 min, M+H.

Using the same procedure but replacing 1-isoamyl-isatoic anhydride with 1-(4-fluorobenzyl)-6-isoatoic anhydride in the final step there was obtained 0.018 g (7%) of 3-(1,1-dioxo-1,4-dihydro-1λ⁶-benzo[1,4]thiazin-3-yl)-1-(4-fluorobenzyl)-4-hydroxy-1H-quinolin-2-one (I-9): LCMS RT 2.45 min, M–H. The sodium salt I-9a was prepared by suspending I-9 (22 mg, 0.05 mmol) in MeCN (1 mL) and adding 0.1N NaOH (490 µL). The resulting mixture was stirred for 5 minutes to give a homogeneous solution. The mixture was lyophilized to afford 23 mg (100%) of I-9a as a light yellow solid: LCMS RT 2.37 min, M–H.

Using the same procedure but replacing 1-isoamyl-isatoic anhydride with 8-aza-1-(2-cyclopropylethyl) isatoic anhydride in the final step there was obtained 0.083 g (31%) of 1-(2-cyclopropyl-ethyl)-3-(1,1-dioxo-1,4-dihydro-1λ⁶-benzo[1,4]thiazin-3-yl)-4-hydroxy-1H-[1,8]naphthyridin-2-one (I-10): LCMS RT 3.59 min, M+H.

Using the same procedure but replacing 1-isoamyl-isatoic anhydride with 8-aza-1-isoamyl-isatoic anhydride in the final step there was obtained 0.080 g (30%) of 1-isoamyl-3-(1,1-dioxo-1,4-dihydro-1λ⁶-benzo[1,4]thiazin-3-yl)-4-hydroxy-1H-[1,8]naphthyridin-2-one (I-11): LCMS RT 2.39 min, M–H.

Using the same procedure but replacing 1-isoamyl-isatoic anhydride with 8-aza-6-fluoro-1-isoamyl-isatoic anhydride in the final step there was obtained 0.150 g (49%) of 3-(1,1-dioxo-1,4-dihydro-1λ6-benzo[1,4]thiazin-3-yl)-6-fluoro-4-hydroxy-1-(3-methyl-butyl)-1H-[1,8]naphthyridin-2-one (I-12): LCMS RT 3.94 min, M+H.

Using the same procedure but replacing 1-isoamyl-isatoic anhydride with 6-fluoro-1-(3,4-difluorobenzyl-isatoic anhydride in the final step there was obtained 0.120 g (51%) of 1-(3,4-difluoro-benzyl)-3-(1,1-dioxo-1,4-dihydro-1λ⁶-benzo[1,4]thiazin-3-yl)-6-fluoro-4-hydroxy-1H-quinolin-2-one (I-25): ms [M–H]=483.3. The sodium salt I-25a was prepared as described above for I-9a.

Using the same procedure but replacing 1-isoamyl-isatoic anhydride with 6-fluoro-1-(4-fluoro-3-methyl-benzyl-isatoic anhydride in the final step there was obtained 0.065 g (27.3%) of 3-(1,1-dioxo-1,4-dihydro-1λ⁶-benzo[1,4]thiazin-3-yl)-6- fluoro-1-(4-fluoro-3-methyl-benzyl)-4-hydroxy-1H-quinolin-2-one (I-26): ms [M−H]=479.3. The sodium salt I-26a was prepared as described above for I-9a.

Using the same procedure but replacing 1-isoamyl-isatoic anhydride with 6-fluoro-1-(3-cyano-benzyl-isatoic anhydride in the final step there was obtained 0.140 g (58.5%) of 3-[3-(1,1-dioxo-1,4-dihydro-1$\lambda^6$-benzo[1,4]thiazin-3-yl)-6-fluoro-4-hydroxy-2-oxo-2H-quinolin-1-ylmethyl]-benzonitrile (I-27): ms [M−H]=472.3. The sodium salt I-27a was prepared as described above for I-9a.

EXAMPLE 2

3-(1,1-Dioxo-1,4-dihydro-1$\lambda^6$-benzo[1,4]thiazin-3-yl)-6-fluoro-1-(4-fluoro-benzyl)-4-hydroxy-1H-quinolin-2-one (I-13)

To a solution of thiazine acetic acid ester 4 (0.20 g, 0.69 mmol) in THF was added NaH (0.11 g, 60% in oil, 2.8 mmol). After 10 min, 1-(4-fluorobenzyl)-6-fluoro-isatoic anhydride (22) was added. The reaction mixture was heated at reflux for 30 min and then the mixture was cooled to rt. HOAc (1 mL) was added and the mixture was heated again at reflux for 30 min. The solvent was removed under reduced pressure and 1N HCl (10 mL) was added to the residue. The mixture was extracted with Et$_2$O. The combined organic phase was washed with brine and dried (MgSO$_4$), filtered and the solvent was removed under reduced pressure. The residue was dissolved in DCM and then concentrated under reduced pressure. This process was repeated. The resulting solid was dried under vacuum. The product was triturated with Et$_2$O, which required sonication, and the resulting precipitate collected by filtration, and dried in vacuo to afford 200 mg (62%) of I-13: LCMS RT 2.46 min, M−H.

3-(1,1-Dioxo-1,4-dihydro-1$\lambda^6$-benzo[1,4]thiazin-3-yl)-6-fluoro-1-(4-fluoro-benzyl)-4-hydroxy-1H-quinolin-2-one, sodium salt (I-13a) was prepared using a procedure similar to that described for I-8a. The mixture was lyophilized to afford 31 mg (100%) of I-13a as a light yellow solid: LCMS RT 2.50 min, M−H.

Using the procedure of Example 2 but replacing 1-isoamyl-isatoic anhydride with 1-(4-fluorobenzyl)-6-methyl-isatoic anhydride there was obtained 0.186 g (57%) of 3-(1,1-dioxo-1,4-dihydro-1$\lambda^6$-benzo[1,4]thiazin-3-yl)-1-(4-fluoro-benzyl)-4-hydroxy-6-methyl-1H-quinolin-2-one (I-14): LCMS RT 2.48 min, M−H. The sodium salt I-14a was prepared as described for I-9a (supra) and afforded 0.031 g (100%): LCMS RT 2.48 min, M−H.

Using the procedure of Example 2 but replacing ethyl benzothiazine acetate with ethyl 6-chlorobenzthiazine acetate there was obtained 0.050 g (33%) of 3-(6-chloro-1,1-dioxo-1,4-dihydro-1$\lambda^6$-benzo[1,4]thiazin-3-yl)-4-hydroxy-1-(3-methyl-butyl)-1H-quinolin-2-one (I-7): LCMS RT 2.7 min, M−H.

EXAMPLE 3

3-(6-Fluoro-4-hydroxy-1-isobutyl-2-oxo-1,2-dihydro-quinolin-3-yl)-1,1-dioxo-1,4-dihydro-1$\lambda^6$-benzo[1,4]thiazine-6-carbonitrile (I-16)

A tube was charged with I-7 (0.400 g, 0.9 mmol), Zn(CN)$_2$ (63 mg, 0.54 mmol), DPPF (100 mg, 0.18 mmol), zinc dust (35 mg, 0.54 mmol), and Pd$_2$(dba)$_3$ (82 mg, 0.89 mmol). The tube was purged with N$_2$, sealed and heated to 120° C. for 3.5 h. After cooling, the mixture was poured into 10% aqueous NH$_4$OH. The solution was washed with ether. The product was extracted into EtOAc. The organic phase was washed with brine and dried over MgSO$_4$. The product was purified by column chromatography on SiO$_2$ eluting with EtOAc/MeOH to afford 0.115 g (29%) of I-16: LCMS RT 2.65 min, M−H.

EXAMPLE 4

3-(6-Aminomethyl-1,1-dioxo-1,4-dihydro-1$\lambda^6$-benzo[1,4]thiazin-3-yl)-6-fluoro-4-hydroxy-1-isobutyl-1H-quinolin-2-one (I-17)

The nitrile I-16 (110 mg, 0.25 mmol) from Example 3 was dissolved in MeOH (5 mL). CoCl$_2$ (120 mg, 0.5 mmol) was added. The resulting suspension was stirred at rt until the CoCl$_2$ dissolved. The mixture was cooled to 0 C. and NaBH$_4$ (95 mg, 2.5 mmol) was added. Upon addition, the mixture turned black and gas evolution was observed. The reaction mixture was stirred at RT for 30 min and then cooled to 0° C. The pH was adjusted to 2 by addition of 1N HCl. The resulting solution was stirred at 0° C. for 30 min and then neutralized with saturated NaHCO$_3$. The solution was washed with ether and then made basic with a Na$_2$CO$_3$ solution and the resulting mixture was extracted into EtOAc which was dried (MgSO$_4$) filtered and evaporated to afford 0.11 g (10%) of I-17: LCMS RT 2.62 min, M+H.

EXAMPLE 5

(S)-5-tert-Butyl-3-(1,1-dioxo-1,4-dihydro-1$\lambda^6$-benzo[1,4]thiazin-3-yl)-4-hydroxy-1-(3-methyl-butyl)-1,5-dihydro-pyrrol-2-one (II-1, SCHEME 2)

step 1—The ester 4a (250 mg, 0.93 mmol) was dissolved in a solution of 50% ethanol containing 50% 1N NaOH (3 mL total volume) and heated to 80° C. After 15 min the reaction mixture was cooled to RT and washed with Et$_2$O. The aqueous solution was acidified with 1N HCl and extracted with ether. The combined Et$_2$O extracts were washed with brine and dried (MgSO$_4$) and the solvents were removed under reduced pressure to afford 0.120 g (54%) of 4b: LCMS RT 1.25 min.

step 2—To a solution of O(t-Bu)-t-butylglycine HCl (11a, 2 g, 8.9 mmol) in MeOH containing 10% acetic acid was added 3-methyl butyraldehyde (1.5 g, 18 mmol) and NaCNBH$_3$ (1.1 g, 18 mmol). This mixture stirred at room temperature for 1 h. The reaction mixture was poured into 1N NaOH. The product was extracted into EtOAc. The organic layer was washed with 1N HCl and brine, dried (MgSO$_4$) and volatile solvents removed under reduced pressure to afford 2.0 g (87%) of 11b: LCMS RT 2.49 min, M+H.

step 3—To a solution of 4b (120 mg, 0.5 mmol) in DCM (5 mL) and DMF (1 mL) was added 11b (130 mg, 0.5 mmol). To this mixture was added DCC (63 mg, 0.5 mmol). The reaction stirred at RT for 30 min, diluted with DCM and washed with 1N NaOH and brine. The combined organic phases were dried (MgSO$_4$) and the volatile solvents were removed under reduced pressure. The crude product was purified by column chromatography on SiO$_2$ eluting with EtOAc/hexanes to afford 0.100 g (41%) of 12: LCMS RT 3.81, 4.03 min, M+H.

step 4—A mixture of 12 (100 mg, 0.21 mmol) and t-BuONa (50 mg, 0.52 mmol) in IPA (5 mL) was stirred at RT for 2 h. The reaction was quenched by the addition of 1 N HCl (10 mL). The product was extracted into DCM and the organic layer was washed with brine and dried (MgSO$_4$). The solvent was removed under reduced pressure and the product was purified using column chromatography on SiO$_2$ eluting with EtOAc/hexane to afford 0.045 g (54%) of 13 (II-1): LCMS RT 3.82 min, M+H.

Using the procedure of Example 6 but replacing O(t-Bu)-t-butylglycine HCl in step 2 with O(t-Bu) cyclohexyl glycine there was obtained 0.085 g (32%) of (S)-5-Cyclohexyl-3-(1,1-dioxo-1,4-dihydro-1λ$^6$-benzo[1,4]thiazin-3-yl)-4-hydroxy-1-isobutyl-1,5-dihydro-pyrrol-2-one (II-2): LCMS RT 3.08 min, M–H.

Using the procedure of Example 6 but replacing O(t-Bu)-t-butylglycine HCl in step 2 with O(t-Bu) isoleucine there was obtained 0.135 g (53%) of (S)-5-((S)-sec-Butyl)-3-(1,1-dioxo-1,4-dihydro-1λ$^6$-benzo[1,4]thiazin-3-yl)-4-hydroxy-1-isobutyl-1,5-dihydro-pyrrol-2-one (II-3): LCMS RT 2.89 min, M–H.

Using the procedure of Example 6 but replacing O(t-Bu)-t-butylglycine HCl in step 2 with O(t-Bu) isoleucine and 3-methyl-butyraldehyde with benzaldehyde there was obtained 0.354 g (56%) of 1-benzyl-5-sec-butyl-3-(1,1-dioxo-1,4-dihydro-1λ$^6$-benzo[1,4]thiazin-3-yl)-4-hydroxy-1,5-dihydro-pyrrol-2-one (II-4): LCMS RT 2.60 min, M–H.

Using the procedure of Example 6 but replacing O(t-Bu)-t-butylglycine HCl in step 2 with O(t-Bu)leucine and 3-methyl-butyraldehyde with 4-fluoro-benzaldehyde (S)-3-(1,1-dioxo-1,4-dihydro-1λ$^6$-benzo[1,4]thiazin-3-yl)-1-(4-fluoro-benzyl)-4-hydroxy-5-isobutyl-1,5-dihydro-pyrrol-2-one (II-5).

Using the procedure of Example 6 but replacing O(t-Bu)-t-butylglycine HCl in step 2 with O(t-Bu)cyclohexylglycine and 3-methyl-butyraldehyde with 4-fluoro-benzaldehyde (S)-5-cyclohexyl-3-(1,1-dioxo-1,4-dihydro-1λ$^6$-benzo[1,4]thiazin-3-yl)-1-(4-fluoro-benzyl)-4-hydroxy-1,5-dihydro-pyrrol-2-one (II-6).

EXAMPLE 6

6-Fluoro-1-(4-fluoro-benzyl)-4-hydroxy-3-(7-hydroxy-1,1-dioxo-1,4-dihydro-1λ6-benzo[1,4]thiazin-3-yl)-1H-quinolin-2-one (I-18) and 2-{3-[6-Fluoro-1-(4-fluoro-benzyl)-4-hydroxy-2-oxo-1,2-dihydroquinolin-3-yl]-1,1-dioxo-1,4-dihydro-1$^6$-benzo[1,4]thiazin-7-yloxy}-acetamide (I-20)

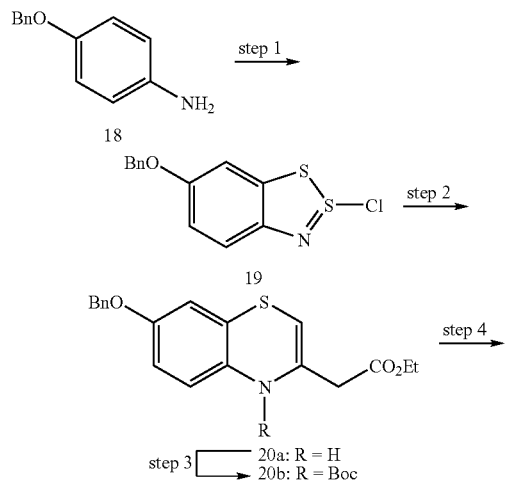

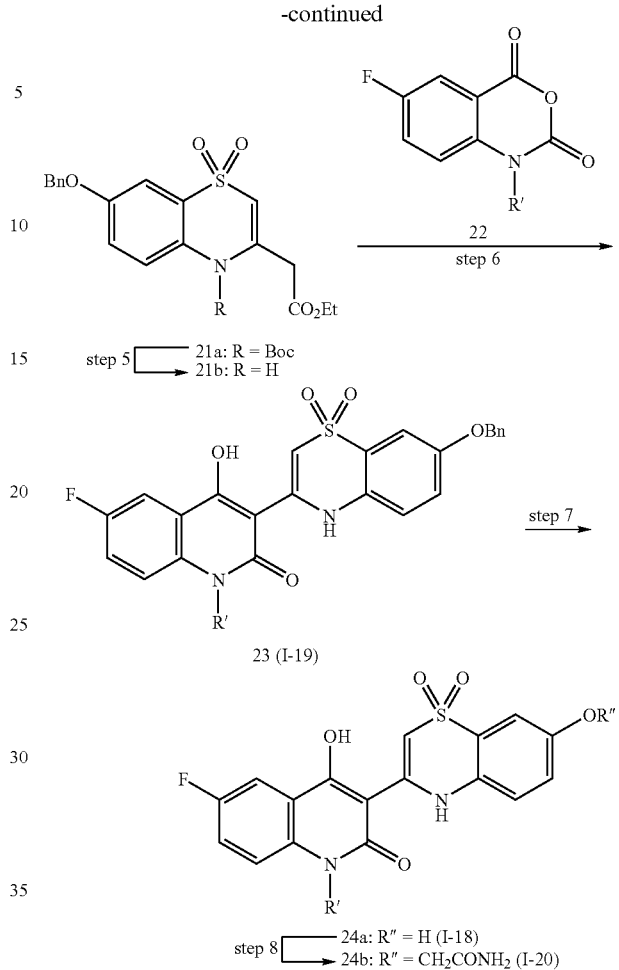

step 1—To a solution of 4-benzyloxyaniline (18, 10.0 g, 50 mmol) in HOAc (50 mL) was added sulfur monochloride (16.9 g, 125 mmol). After stirring at RT for 1 h the mixture was heated to 75° C. for 2 h. The mixture was cooled to RT and toluene (150 mL) was added. The resulting red solid was collected, washed with toluene and dried under reduced pressure to afford 12 g (81%) of 19: LCMS RT 3.33 min.

step 2—To a suspension of 19 (9.0 g, 30 mmol) in water (50 mL) was added Na$_2$S$_2$O$_4$ (8.1 g, 40 mmol). The mixture adjusted to pH 12 using 1N NaOH. This mixture was stirred at 50° C. for 2 h. Dioxane (50 mL) and chloroacetoacetate (10 g, 61 mmol) were added sequentially and the temperature was maintained at 50° C. for 1 h. The mixture was cooled to RT and the dioxane was removed under in vacuo. The aqueous phase was extracted into EtOAc and the combined aqueous phase was washed with brine and dried over MgSO$_4$. The product was purified by column chromatography on SiO$_2$ eluting with EtOAc/hexanes to afford 1.7 g (16%) of 20a: LCMS RT 4.44 min, M+H.

step 3—20a was converted to 20b as described in step 2 of Example 1. The product was used in the next step without further purification.

step 4—20b was converted to 21a as described in step 3 of Example 1. The product was used in the next step without further purification.

step 5—21a was converted to 21b (0.420 g, 43% for the previous three steps, LCMS RT 2.09 min, M+H) as described in step 4 of Example 1. The product was used in the next step without further purification.

step 6—The condensation of thiazine acetic acid ester 21b (0.20 g, 0.69 mmol) and 1-(4-fluorobenzyl)-6-fluoro-isatoic anhydride (22) was carried out as described in Example 2 except thiazine 4 was replaced by 21b to afford 0.310 g (68%) of 23 (I-19): LCMS RT 2.56 min, M–H.

step 7—To a solution of 23 (220 mg, 0.38 mmol) in DCM (10 mL) at 0° C. was added N,N-dimethylaniline (280 mg, 2.3 mmol) and AlCl₃ (410 mg, 3.1 mmol). The reaction stirred at 0° C. for 30 min. The mixture was poured into 1N NaOH (50 mL). The aqueous layer was washed with EtOAc. The aqueous layer was acidified with 1N HCl and the product was extracted into EtOAc. The combined organic phase was washed with brine, dried (MgSO₄) and the solvent was removed in vacuo to afford 0.159 g (81%) of 24a (I-18): LCMS RT 2.51 min, M–H).

step 8—To a solution of 24a (0.054 g, 0.112 mmol) in acetone (10 mL) was added 2-bromoacetamide (0.046 g, 0.336 mmol) and K₂CO₃ (0.309 g, 3.2 mmol). The reaction was heated at reflux for 2 h. The mixture was poured into water (50 mL). The product was extracted with EtOAc. The combined extracts were washed with 1N HCl and brine, dried (MgSO₄) and the solvent was removed in vacuo to afford 0.035 g (58%) of 24b (I-20): LCMS RT 2.37 min, M–H.

Using the procedure in step 8 but replacing 2-bromoacetamide with N-methyl-2-chloroacetamide there was obtained 0.070 g (30.5%) of 2-{3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-N-methyl-acetamide (I-42): ms [M–H]=552.2.

Using the procedure in step 8 but replacing 2-bromoacetamide with N,N-dimethyl-2-bromoacetamide there was obtained 0.160 g (90.7%) of 2-{3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-N,N-dimethyl-acetamide (I-34): ms [M–H]=566.2.

EXAMPLE 7

N-{3-[6-Fluoro-1-(4-fluoro-benzyl)-4-hydroxy-2-oxo-1,2-dihydro-quinolin-3-yl]-1,1-dioxo-1,4-dihydro-1⁶-benzo[1,4]thiazin-7-yl}-methanesulfonamide (I-24)

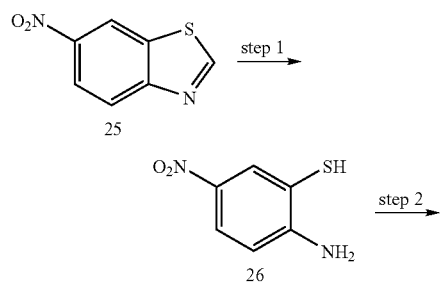

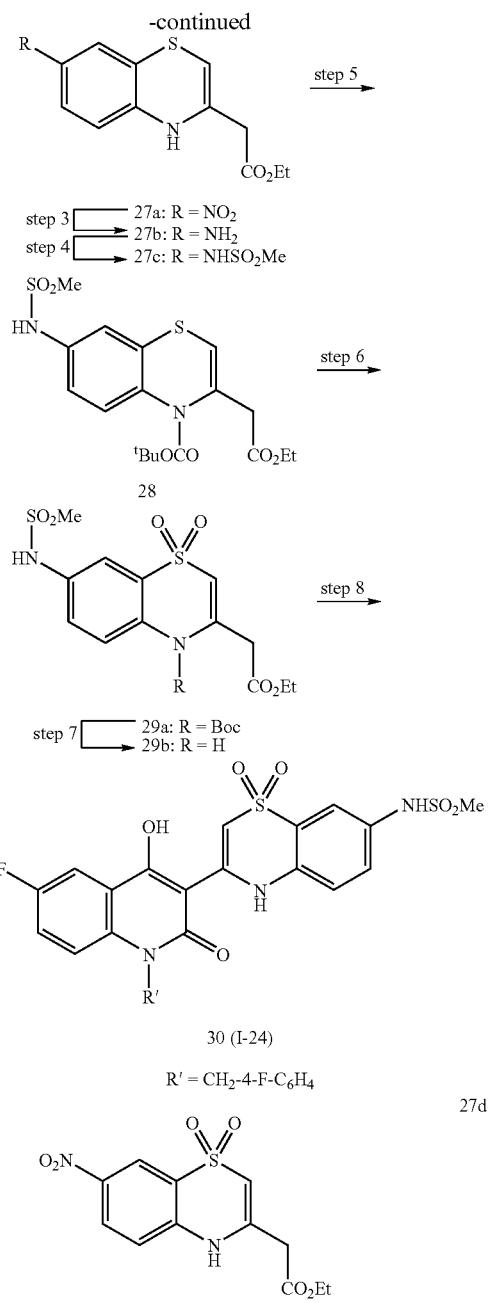

step 1—To a solution of 6-nitro-benzothiazole (25, 2.0 g, 11 mmol) and EtOH (20 mL) was added hydrazine monohydrate (5.0 mL, 161 mmol). After stirring at RT for 3 h the EtOH was removed under reduced pressure. The resulting red solid was dissolved in EtOAc and washed with a 0.1 M HCl solution. The organic phase was washed with brine and dried over MgSO₄. The solid was triturated with Et₂O and dried under reduced pressure to afford 1.8 g (94%) of 26: ¹H-NMR (400 MHz, CDCl₃): δ 8.35 (s, 1H), 8.00 (d, 1H), 6.7 (d, 1H), 4.9 (broad, 2H), 3.0 (s, 1H).

step 2—To a solution of 26 (0.50 g, 2.9 mmol) in THF (30 mL) was added TEA (0.82 mL, 5.9 mmol). Ethyl chloroacetoacetate (7, 0.52 g, 3.2 mmol) was added and the mixture stirred at RT for 12 h. The solvent was removed under reduced pressure and the residue was dissolved in EtOAc. The mixture was heated at 80° C. for 2 h. The mixture was cooled to RT, washed with brine and dried (MgSO$_4$). The product was triturated with Et$_2$O and dried under reduced pressure to afford 0.61 g (70%) of 27a: LCMS RT 3.48 min, M+H.

step 3—To a solution of 27a (2.00 g, 7.1 mmol) in EtOH (25 mL) was added tin (II) chloride (6.8 g, 36 mmol) and 1N HCl (1 mL). The mixture was heated at 100° C. for 3 h. The mixture was cooled to RT and the EtOH was removed under reduced pressure. The residue was dissolved in EtOAc and 6N NaOH (30 mL) was added. The mixture was filtered and the solid was washed with copious amounts of EtOAc. The filtrate was washed with brine and dried over Na$_2$SO$_4$. The product was purified by column chromatography on SiO$_2$ eluting with EtOAc/hexanes to afford 1.7 g (80%) of 27b: LCMS RT 2.84 min, M+H.

step 4—A solution of 27b (0.50 g, 1.9 mmol) in DCM (20 mL) and TEA (1 mL, 6.2 mmol) was cooled to 0° C. Methanesulfonyl chloride (0.22 g, 1.9 mmol) was added dropwise over 30 min and the resulting mixture was stirred at RT for an additional 30 min. The solvent was removed under reduced pressure and the residue was dissolved in EtOAc. The organic phase was washed with brine, dried (Na$_2$SO$_4$) and the solvent was removed in vacuo. The product was purified by column chromatography on SiO$_2$ eluting with EtOAc/hexanes to afford 0.591 g (90%) 27c: LCMS RT 2.87 min, M+H.

step 5-step 7—Protection of the nitrogen atom (step 5), oxidation of the sulfide (step 6) and deprotection of the nitrogen (step 7) to afford 29b were carried out as described in example 1, steps 2-4 without purification of the intermediate products to afford 0.420 g (78% overall) of 29b: LCMS RT 1.81 min, M−H.

step 8—The condensation of thiazine acetic acid ester 29b (0.20 g, 0.69 mmol) and 1-(4-fluorobenzyl)-6-fluoro-isatoic anhydride 22 was carried out as described in Example 2 except thiazine 4 was replaced by 29b to afford 0.090 g (29%) of 30 (I-24): LCMS RT 2.55 min, M−H.

Compounds I-69 (6,7-difluoro-1-(4-fluoro-benzyl)-1H-benzo[d][1,3]oxazine-2,4-dione), I-44 (1-methyl-1H-benzo[d][1,3]oxazine-2,4-dione), I-45 (6-fluoro-1-(4-fluoro-benzyl)-1H-benzo[d][1,3]oxazine-2,4-dione), I-48 (6-fluoro-1-(4-fluoro-3-methyl-benzyl)-1H-benzo[d][1,3]oxazine-2,4-dione, I-49 (1-(3-chloro-4-fluoro-benzyl)-6-fluoro-1H-benzo[d][1,3]oxazine-2,4-dione, I-50 (6-fluoro-1-pyridin-3-ylmethyl-1H-benzo[d][1,3]oxazine-2,4-dione), I-51 (1-cyclohexylmethyl-6-fluoro-1H-benzo[d][1,3]oxazine-2,4-dione), I-52 (6-fluoro-1-(3-methyl-butyl)-1H-benzo[d][1,3]oxazine-2,4-dione, I-54 (1-(3,4-difluoro-benzyl)-6-fluoro-1H-benzo[d][1,3]oxazine-2,4-dione, I-55 (6-fluoro-1-(4-fluoro-3-trifluoromethyl-benzyl)-1H-benzo[d][1,3]oxazine-2,4-dione, I-58 (1-(4-fluoro-benzyl)-6-methoxy-1H-benzo[d][1,3]oxazine-2,4-dione, I-59 (6-chloro-1-(4-fluoro-benzyl)-1H-benzo[d][1,3]oxazine-2,4-dione), I-66 (6-fluoro-1-pyridin-4-ylmethyl-1H-benzo[d][1,3]oxazine-2,4-dione) and I-67 (7-chloro-1-(4-fluoro-benzyl)-1H-benzo[d][1,3]oxazine-2,4-dione)were prepared as described in Example 7 except in step 8, 1-(4-fluorobenzyl)-6-fluoroisatoic anhydride 22 was replaced by the appropriate 1-substituted 1H-benzo[d][1,3]oxazine-2,4-dione indicated in parentheses. Methods for the preparation of 1-substituted 1H-benzo[d][1,3]oxazine-2,4-dione (isatoic anhydrides) are described in example 24.

EXAMPLE 8

3-(1,1-Dioxo-1,4-dihydro-1-$^6$-benzo[1,4]thiazin-3-yl)-1-(4-fluoro-benzyl)-isoquinolin-4-ol (IV-1; see SCHEME 3, R$^2$=CH$_2$-p-C$_6$H$_4$F)

step 1—Phosphorous oxychloride (40 mL) was added to a flask containing 4-hydroxy-1-oxo-1,2-dihydro-isoquinoline-3-carboxylic acid methyl ester (31, 5.00 g, 22.8 mmol). After stirring at 70° C. for 3 h, the POCl$_3$ was removed under reduced pressure, and water was added to the residue. The resulting solid was collected by filtration, and the solid was further washed with water and hexanes then dissolved in dichloromethane. The organic phase was dried (MgSO$_4$), filtered and the solvent was removed in vacuo to afford 5.10 g, (94% theory) of 32a: LCMS RT 3.6 min, M+H.

step 2—To a suspension of the phenol 32a (1.20 g, 5.05 mmol) in DMF (15 mL) was added Cs$_2$CO$_3$ (1.97 g, 6.06 mmol) followed by methyl iodide (1.57 mL, 25.5 mmol). After stirring at RT for 20 h, the reaction mixture was diluted with EtOAc and washed with water (2×) and brine (2×). The organic extracts were dried (MgSO$_4$), filtered and the solvent was removed in vacuo to afford 1.25 g (98% theory) of 32b LCMS RT 3.0 min, M+H.

step 3—The methyl ether 32b (0.500 g, 1.99 mmol) was dissolved in THF (5 mL) and Pd(PPh$_3$)$_4$ (0.230 g, 0.200 mmol) and 4-fluorobenzylzinc bromide (4.8 mL, 0.5M in THF, 2.38 mmol) were added sequentially. This mixture was stirred vigorously for 18 h at 60° C. and quenched with an aqueous solution of NH$_4$Cl. The product was twice extracted into EtOAc and the combined organic layers were washed with brine, dried (MgSO$_4$), filtered and the solvent was removed in vacuo. The product was purified by column chromatography on SiO$_2$ eluting with EtOAc/hexanes to afford 0.400 g, (62% theory) of 33: LCMS RT 3.7 min, M+H.

step 4—To a solution of 2-(methylsulfonyl)benzenamine hydrochloride (34, 182 mg, 1.66 mmol) in THF (2 mL) cooled to −78° C. was added n-BuLi (1.8 mL, 2.9 mmol; 1.6M solution in hexanes). The yellow reaction mixture was stirred at −78° C. for 1 h, and a solution of the ester 33 (190 mg, 0.58 mmol) in THF (1.5 mL) was added. The reaction mixture was allowed to slowly warm to RT overnight, and the dark reaction mixture was diluted with EtOAc. The organic layer was washed sequentially with 10% HCl, water, and brine. The combined organic layers were dried (MgSO$_4$), filtered and the solvent removed in vacuo. The crude mixture containing 35a was used directly in the next step.

step 5—To a solution of the crude product from step 4 in DCM (1 mL) and cooled to 0° C. was added a 1.0M BBr$_3$ solution in DCM (6.0 mL, 6.0 mmol). The reaction mixture was stirred at RT for 18 h then concentrated in vacuo. Water was added to the residue, and the resulting solid was collected by filtration and washed with water. The product was purified by chromatography on SiO$_2$ eluting with EtOAc/hexanes to afford 4 mg (20% theory) of 35b (IV-1): LCMS RT 4.0 min, M+H.

1-(4-Fluoro-benzyl)-3-(4-methyl-1,1-dioxo-1,4-dihydro-1$^6$-benzo[1,4]thiazin-3-yl)-isoquinolin-4-ol was prepared in similar fashion except N-methyl-2-(methylsulfonyl)benzenamine hydrochloride was substituted for 2-(methylsulfonyl) benzenamine in step 4 to afford 70 mg o(24% theory) IV-2: LCMS RT 3.6 min, M+H.

3-(7-Chloro-4-methyl-1,1-dioxo-1,4-dihydro-1λ$^6$-benzo [1,4]thiazin-3-yl)-6-fluoro-1-(4-fluoro-benzyl)-isoquinolin-4-ol was prepared in similar fashion except 1-chloro-6-fluoro-4-methoxy-isoquinoline-3-carboxylic acid methyl ester was substituted for 1-chloro-4-methoxy-isoquinoline- 3-carboxylic acid methyl ester in step 3 and 4-chloro-N-methyl-2-(methylsulfonyl)benzenamine was substituted for 2-(methylsulfonyl)benzenamine hydrochloride in step 4 to afford 7 mg (14% theory) of IV-4: LCMS RT 1.6 min, M+H.

EXAMPLE 9

3-(7-Chloro-4-methyl-1,1-dioxo-1,4-dihydro-1λ⁶-benzo[1,4]thiazin-3-yl)-1-(4-fluoro-benzyl)-isoquinolin-4-ol (IV-3)

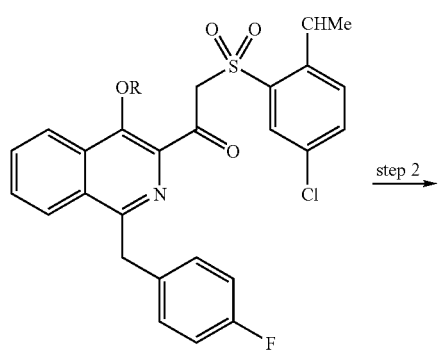

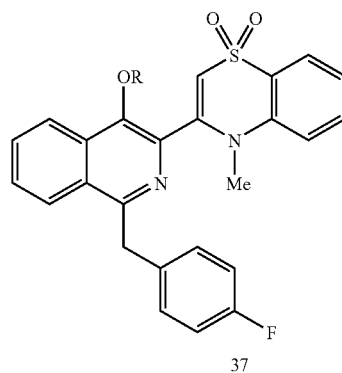

2-(5-Chloro-2-methylamino-benzenesulfonyl)-1-[1-(4-fluoro-benzyl)-4-hydroxy-isoquinolin-3-yl]-ethanone (36a) was prepared from 1-(4-fluoro-benzyl)-4-methoxy-isoquinoline-3-carboxylic acid methyl ester and (4-chloro-2-methanesulfonyl-phenyl)-methyl-amine as described in steps 1-4 of Example 8.

step 1—To a solution of ether 36a (50 mg, 0.073 mmol) in DCM (1 mL) cooled to 0° C. was added a 1.0M BBr₃ solution in DCM (1.0 mL, 1.0 mmol). The reaction mixture was stirred at RT for 18 h then concentrated in vacuo. Water was added to the residue, and the resulting solid was collected by filtration and washed with water and hexanes. The crude material containing 36b was used directly in the next step.

step 2—To a suspension of a crude product step 1 in EtOH (1 mL) was added H₂SO₄ (0.041 mL, 0.80 mmol). The reaction mixture was heated at reflux for 2.5 h then concentrated in vacuo. Water was added to the residue, and the resulting solid was collected by filtration and washed sequentially with water, hexanes and ether to afford 25 mg (65% theory) of 37: LCMS RT 4.4 min, M+H.

EXAMPLE 10

6-Hydroxy-1,3-diisobutyl-5-(4-methyl-1,1-dioxo-1,4-dihydro-1λ⁶-benzo[1,4]thiazin-3-yl)-1H-pyrimidine-2,4-dione

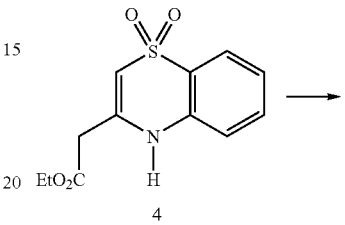

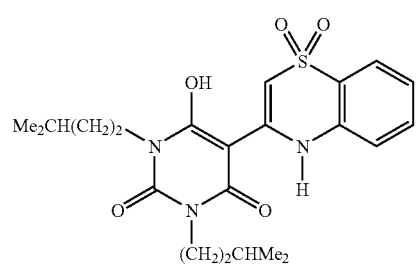

Sodium hydride (0.054 g, 2.25 mmol, 60% in mineral oil) is added to a stirred solution of (4-methyl-1,1-dioxo-1,4-dihydro-1λ⁶-benzo[1,4]thiazin-3-yl)-acetic acid ethyl ester (4, 0.20 g, 0.750 mmol) in dioxane (50 mL) under an Ar atmosphere. After hydrogen evolution ceases the solution is stirred for an addition 5 min, 3-methylbutylisocyanate (0.241 g, 2.43 mmol) is added and the mixture is heated to reflux for 2 h, is cooled and is poured into 20 mL 1 N HCl and 25 mL of ice. The solid precipitate is filtered and is purified by flash chromatography on SiO₂ which affords 38.

EXAMPLE 11

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-N-methyl-methanesulfonamide (I-35)

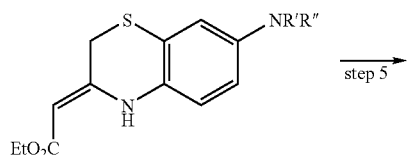

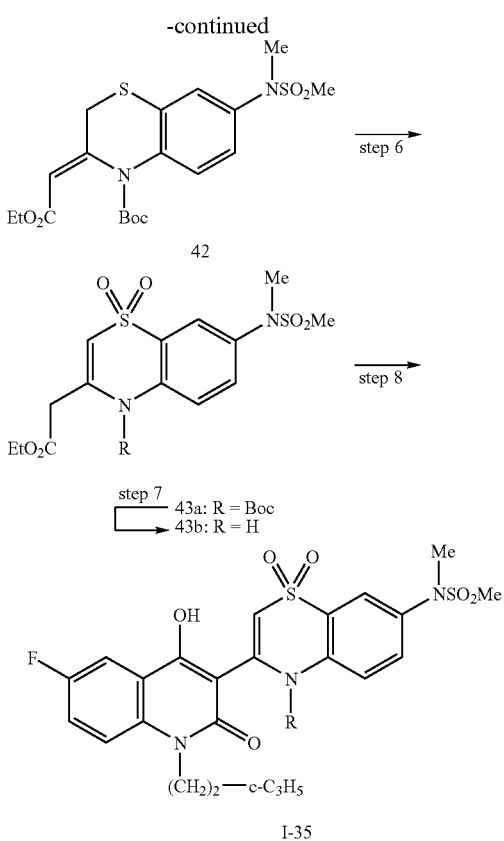

steps 5 to 7—Step 5-7 of the current example were carried out as described in steps 2-4 of Example 1.

step 8—Using the procedure described in step 5 of Example 1 but replacing 4 with [7-(methanesulfonyl-methyl-amino)-1,1-dioxo-1,4-dihydro-1λ⁶-benzo[1,4]thiazin-3-yl]-acetic acid ethyl ester (43b) there was obtained N-{3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-N-methyl-methanesulfonamide (I-35: mp 208-212° C., ms [M+H]=534.1.

N-{3-[6-Fluoro-1-(4-fluoro-benzyl)-4-hydroxy-2-oxo-1,2-dihydro-quinolin-3-yl]-1,1-dioxo-1,4-dihydro-1λ6-benzo[1,4]thiazin-7-yl}-N-methyl-methanesulfonamide (I-47) was prepared as described above except in step 8, 1-(2-cyclopropyl-ethyl)-6-fluoro-1H-benzo[d][1,3]oxazine-2,4-dione was replaced by 6-fluoro-1-(4-fluoro-benzyl)-1H-benzo[d][1,3]oxazine-2,4-dione

EXAMPLE 12

3-(7-Amino-1,1-dioxo-1,4-dihydro-1λ6-benzo[1,4]thiazin-3-yl)-1-(2-cyclopropyl-ethyl)-4-hydroxy-1H-quinolin-2-one (I-21)

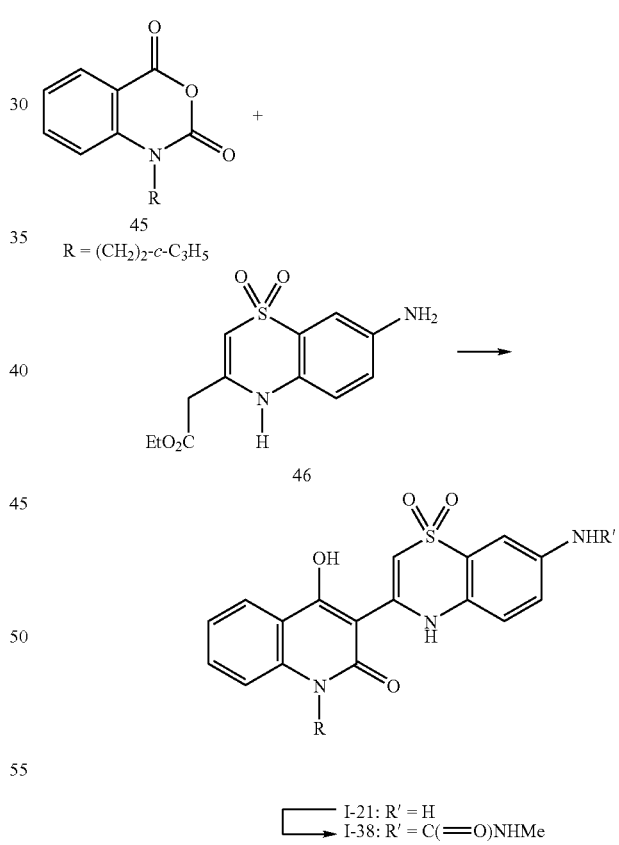

step 1—To a solution of 40a (0.320 g, 1.28 mmol), DIPEA (0.455 mL, 2.56 mmol) and DCM (15 mL) was added TFAA (1.28 mL, 1.28 mmol, 1.0 M in DCM). The reaction was stirred at RT for 30 min. HPLC indicated some starting material remained and an addition 2 drops of TFAA was added. The reaction was stirred for several minutes and the volatile solvents were removed in vacuo. The crude product was passed through a SiO₂ plug with 25% EtOAc/hexane and the solvents were evaporated and the resulting trifluoroacetamide 40b was used directly in step 2.

step 2—To a solution of 40b (0.420 g, 1.21 mmol) and DMF (12 mL) were added K₂CO₃ (0.251 g, 1.82 mmol) and methyl iodide (0.091 mL, 1.46 mmol). The reaction was stirred for 8 h. The reaction was diluted with 50 mL of water and extracted with Et₂O. The combined extracts were washed witth water, dried (MgSO₄), filtered and evaporated to afford 40c step 3—The trifluoroacetamide 40c (0.430 g, 1.19 mmol) was dissolved in MeOH (50 mL) and water (20 mL). To this solution was added K₂CO₃ (1.10 g, 7.95 mmol) and the resulting solution was stirred at RT for 1 h. The volatile solvents were removed in vacuo, diluted with water and extracted with EtOAc. The combined extracts were washed with brine, dried (MgSO₄), filtered and evaporated to afford 0.260 g of 40d.

step 4—To a solution of 40d (0.260 g 0.984 mmol), DIPEA (0.343 mL, 1.97 mmol) and DCM (20 mL) cooled to 0° C. was added a solution of mesyl chloride (0.113 g, 0.984 mmol) and DCM. After 5 min no starting material was evident and the reaction was diluted with water and extracted with EtOAc, The combined extracts were was with brine, dried (MgSO₄), filtered and evaporated. The crude product was purified by passing through a plug of SiO₂ eluting with a EtOAc/hexane gradient (25 to 50% EtOAc) to afford 0.310 g of 40e.

To a solution of 46 (0.078 g, 0.276 mmol) and anhydrous THF (10 mL) was added NaH (0.0265 g, 1.11 mmol). After gas evolution ceased the isatoic anhydride 45 (0.0639 g, 0.276 mmol) was added and the reaction mixture was heated at reflux. After 5 h the reaction was complete and several drops of HOAc was added to quench residual NaH and induce cyclization of the adduct. The reaction mixture was partitioned between water and EtOAc. The combined extracts were washed with saturated NaHCO$_3$ and brine, dried (MgSO$_4$), filtered and evaporated. The crude product was purified by SiO$_2$ chromatography and eluted with EtOAc/hexane (1:1) to afford 0.080 g of I-21 as a yellow powder: mp>250° C.; ms [M+H]$^+$=424.1.

To a solution of I-21 (0.027 g, 0.0612 mmol), DCM (2 mL) and DMF (0.5 mL) was added methyl isocyanate (MIC, 67.3 μL, 0.0673 mmol, 1M solution in DCM). The resulting solution was stirred in a sealed tube and progress of the reaction was monitored by hplc. After several hours the reaction appeared to slow and an additional aliquot of MIC was added and stirring continued. The reaction mixture was partitioned between Et$_2$O and water and the Et$_2$O extracts were washed with dil. HCl. Analysis of the organic extracts indicated the presence of both starting material and product. A solid precipitated from the aqueous phase which was collected, washed with Et$_2$O and dried to afford I-38: mp 220° C. (decomp), [M+H]=499.1.

EXAMPLE 13

3-(7-Amino-1,1-dioxo-1,4-dihydro-1λ$^6$-benzo[1,4]thiazin-3-yl)-6-fluoro-1-(4-fluoro-benzyl)-4-hydroxy-1H-quinolin-2-one (I-22), N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-acetamide (I-23) and N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide (I-24)

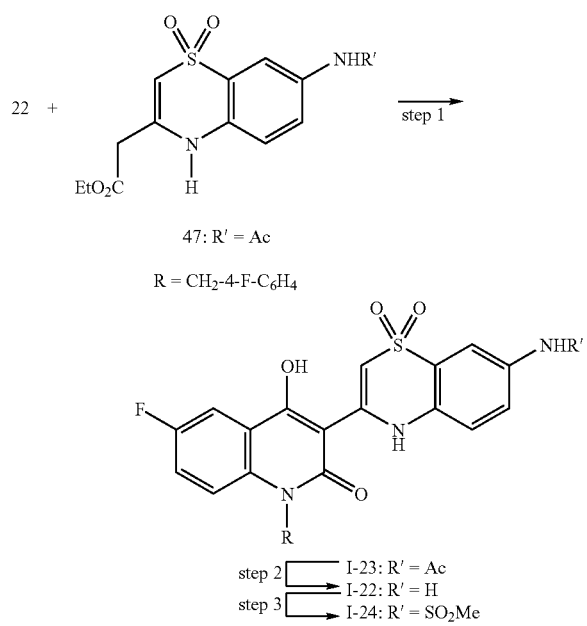

step 1—Thiazine 47 (0.300 g, 0.925 mmol) and anhydrous THF (10 mL) was added NaH (0.185 g, 4.62 mmol). The reaction mixture was warmed to 75° C. for 15 min to produce a homogenous solution. The isotoic anhydride 22 (0.265 g, 0.925 mmol) was added and heating was continued for 1.5 h. The reaction was cooled to RT and HOAc (1 mL) was added and heating at 75° C. resumed for 15 min. The reaction mixture was diluted with 1N HCl and extracted with EtOAc. The combined extracts were washed with saturated NaHCO$_3$ and brine, dried (MgSO$_4$), filtered and concentrated in vacuo. The crude product was triturated with toluene and re-evaporated. The residue was triturated with Et$_2$O to afford 0.150 g (31%) of I-23: mp>250° C.; ms [M−H]=522.3.

step 2—A solution of I-23 (0.050 g, 0.0955 mmol) EtOH (10 mL) and 5N NaOH (10 mL) was heated at reflux. The reaction mixture was cooled to RT and the reaction mixture was concentrated in vacuo. The residue was neutralized with 1N HCl and extracted with Et$_2$O. The combined extracts were washed with brine, dried (MgSO$_4$), filtered and concentrated in vacuo. The residue was triturated with Et$_2$O, filtered and dried in vacuo to afford 0.045 g of I-22: mp>250° C.; ms [M−H]=480.4.

step 3—To a solution of I-22 (0.100 g, 0.208 mmol) and DCM (15 mL) was added sequentially DIPEA (0.2684 g, 2.077 mmol) and mesyl chloride (0.0476 g, 0.415 mmol). The reaction mixture was monitored by tlc which exhibited a new major spot and several minor components. The reaction mixture was concentrated in vacuo and partitioned between EtOAc and 1 N HCl. The EtOAc extract was washed with brine, dried (MgSO$_4$), filtered and evaporated. The crude product was purified by SiO$_2$ chromatography eluting with EtOAc. The recovered product was further purified by preparative tlc to afford I-24: [M−H]=558.2. (Example 7 provides an alternative route to I-24) The sodium salt I-24a was prepared as described above for I-9a in Example 1.

EXAMPLE 14

N-{3-[1-(2-Cyclopropyl-ethyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-methane-sulfonamide, sodium salt (I-28a)

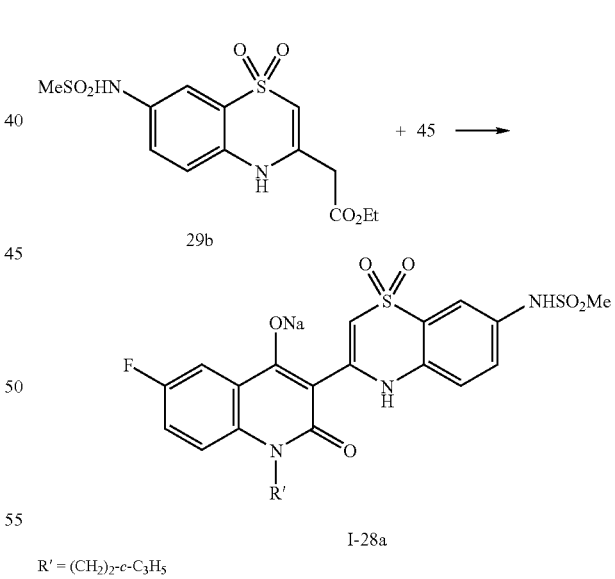

To a solution of 29b (0.128 g, 0.3552 mmol) and THF (15 mL) was added NaH (0.0511 g, 2.13 mmol). After stirring for 5 min at RT 45 (0.097 g, 0.39 mmol) was added and the resulting solution heated at reflux for 3 h. The reaction was quenched with HOAc and partitioned between water and EtOAc. The organic extracts were washed with brine, dried (Na$_2$SO$_4$), filtered and concentrated in vacuo. The crude product was triturated with Et$_2$O, filtered and chromatographed on SiO₂ eluting with EtOAc/hexanes (1:1) to afford I-28 as a yellow solid. The solid was dissolved in MeCN and 1 equivalent of 0.1M NaOH was added and the reaction stirred for 1 h. The sodium salt was isolated by lyophilisation of the aqueous solution to afford I-28a: ms [M+H]=520.1.

Using the same procedure but replacing 29b with [1,1-dioxo-7-(propane-1-sulfonylamino)-1,4-dihydro-1λ⁶-benzo[1,4]thiazin-3-yl]-acetic acid ethyl ester there was obtained 0.124 mg (62.8%) of propane-1-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ6-benzo[1,4]thiazin-7-yl}-amide (I-29: mp 145-150° C., ms [M+H]=548.1. The corresponding sodium salt I-29a was available as described above.

Using the same procedure but replacing 29b with (7-ethanesulfonylamino-1,1-dioxo-1,4-dihydro-1λ⁶-benzo[1,4]thiazin-3-yl)-acetic acid ethyl ester there was obtained 0.0891 g (41.7%) of ethanesulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ6-benzo[1,4]thiazin-7-yl}-amide (I-32): mp 140-142° C., ms [M+H]=534.1.

Using the same procedure but replacing 29b with (7-cyclopropanesulfonylamino-1,1-dioxo-1,4-dihydro-1λ⁶-benzo[1,4]thiazin-3-yl)-acetic acid ethyl ester there was obtained 0.123 g (58.1%) of cyclopropane-1-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ6-benzo[1,4]thiazin-7-yl}-amide (I-33): mp 145-155° C., ms [M+H]=546.1.

Using the same procedure but replacing 29b with [7-(3,5-dimethyl-isoxazole-4-sulfonylamino)-1,1-dioxo-1,4-dihydro-1λ⁶-benzo[1,4]thiazin-3-yl]-acetic acid ethyl ester there was obtained 0.013 g (9.64%) of 3,5-dimethyl-isoxazole-4-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide (I-36): mp 150-157° C., ms [M+H]=601.1.

Using the same procedure but replacing 29b with (7-benzenesulfonylamino-1,1-dioxo-1,4-dihydro-1λ⁶-benzo[1,4]thiazin-3-yl)-acetic acid ethyl ester there was obtained N-{3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-benzenesulfonamide (I-37): mp>200° C., ms [M+H]=582.1.

EXAMPLE 15

6-Fluoro-1-(4-fluoro-benzyl)-4-hydroxy-3-(7-methoxy-1,1-dioxo-1,4-dihydro-1λ6-benzo[1,4]thiazin-3-yl)-1H-quinolin-2-one (I-30)

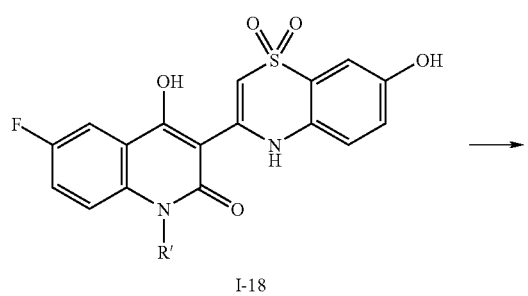

I-18

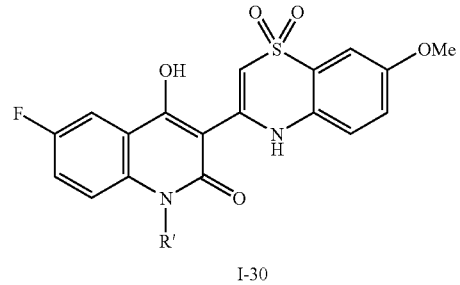

I-30

R' = CH₂-4-F-C₆H₄

To a solution of I-18 (0.15 g, 0.311 mmol) and acetone (10 mL) was added K₂CO₃ (0.86 g, 6.2 mmol) and MeI (0.078 mL, 1.24 mmol) and the resulting mixture was stirred at RT overnight. The reaction was concentrated in vacuo and the resulting residue partitioned between water and EtOAc. The organic extracts were combined, dried (MgSO₄), filter and evaporated. The crude product was purified by SiO₂ chromatography eluting with a DCM/EtOAc gradient (0 to 10% EtOAc) to afford 0.060 g of I-30 as a solid: mp>250° C., ms [M+H]=497.1.

Using the same procedure but replacing methyl iodide with methyl bromoacetate there was obtained 90 mg (39%) of {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-acetic acid methyl ester (I-31: mp 200-207° C., ms [M+H]=555.1.

EXAMPLE 16

3-{3-[1-(2-Cyclopropyl-ethyl)-6-fluoro-4-hydroxy-2-oxo-1,2-dihydro-quinolin-3-yl]-1,1-dioxo-1,4-dihydro-1λ6-benzo[1,4]thiazin-7-yloxy}-propionamide (I-39)

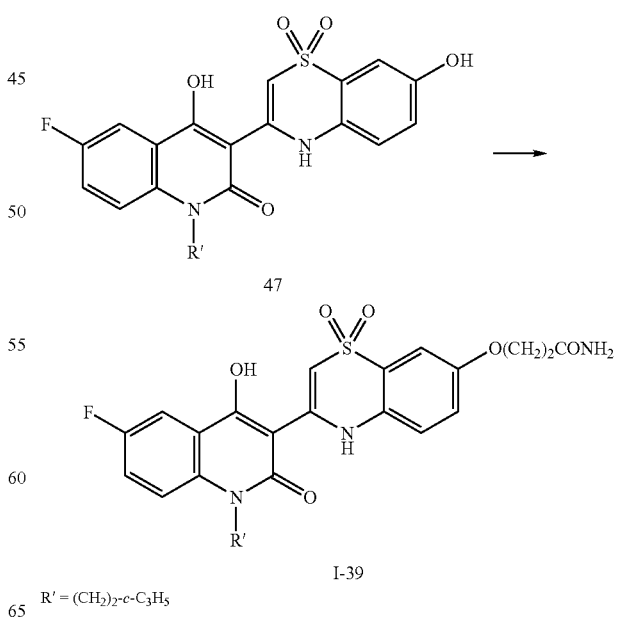

I-39

R' = (CH₂)₂-c-C₃H₅

Thiazine 47 was prepared as described for I-18 in example 6 except in step 6, 22 was replaced with 1-(2-cyclopropyl-ethyl)-6-fluoro-1H-benzo[d][1,3]oxazine-2,4-dione.

To a solution of 47 (0.13 g, 0.59 mmol) in THF was added NaH (0.026 g, 0.65 mmol) and the solution was stirred for 20 min at RT. To the solution of the sodium phenolate salt was added acrylamide (0.042 g, 0.59 mmol) and the solution was stirred at RT overnight. The solution was concentrated in vacuo and the residue partitioned between 1N HCl and EtOAc. The organic phase was dried (MgSO$_4$), filtered and evaporated and the residue purified by SiO$_2$ chromatography eluting with 4% MeOH/DCM to afford to I-39 which was approximately 90% pure: ms [M+H]=514.1.

EXAMPLE 17

1-{3-[1-(2-cyclopropyl-ethyl)-6-fluoro-4-hydroxy-2-oxo-1,2-dihydro-quinolin-3-yl]-1,1-dioxo-1,4-dihydro-1$\lambda^6$-benzo[1,4]thiazin-7-yl}-sulfamide (I-40)

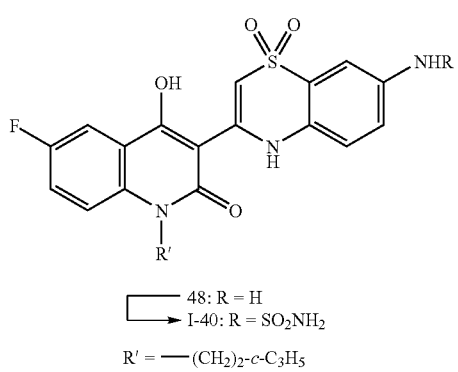

To a solution of 48 (0.200 g, 0.45 mmol) and DCM (50 mL) at RT was added dropwise a DCM solution of N-tert-butyl-chlorosulfonylcarbamate (0.12 g, 0.54 mmol). The reaction mixture was stirred overnight at RT and the solvent removed in vacuo and the crude product was purified by SiO$_2$ chromatography eluting with an acetone/hexane gradient containing 0.5% HCO$_2$H (10-50% acetone). The purified material was dissolved in DCM/MeOH (3:1) and TFA (2 mL) was added. The reaction was stirred at RT overnight and 0.1 mL of water was added and the reaction was stirred at 50° C. for 4 h. The reaction was concentrated and DCM (50 mL) was added. The suspension was sonicated and the solid was filtered and air dried to afford 52 mg of I-40:

EXAMPLE 18

N-{3-[(S)-5-tert-Butyl-1-(4-fluoro-benzyl)-4-hydroxy-2-oxo-2,5-dihydro-1H-pyrrol-3-yl]-1,1-dioxo-1,4-dihydro-1$\lambda^6$-benzo[1,4]thiazin-7-yl}-methane-sulfonamide (II-8)

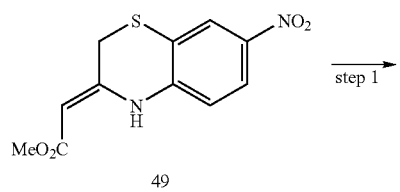

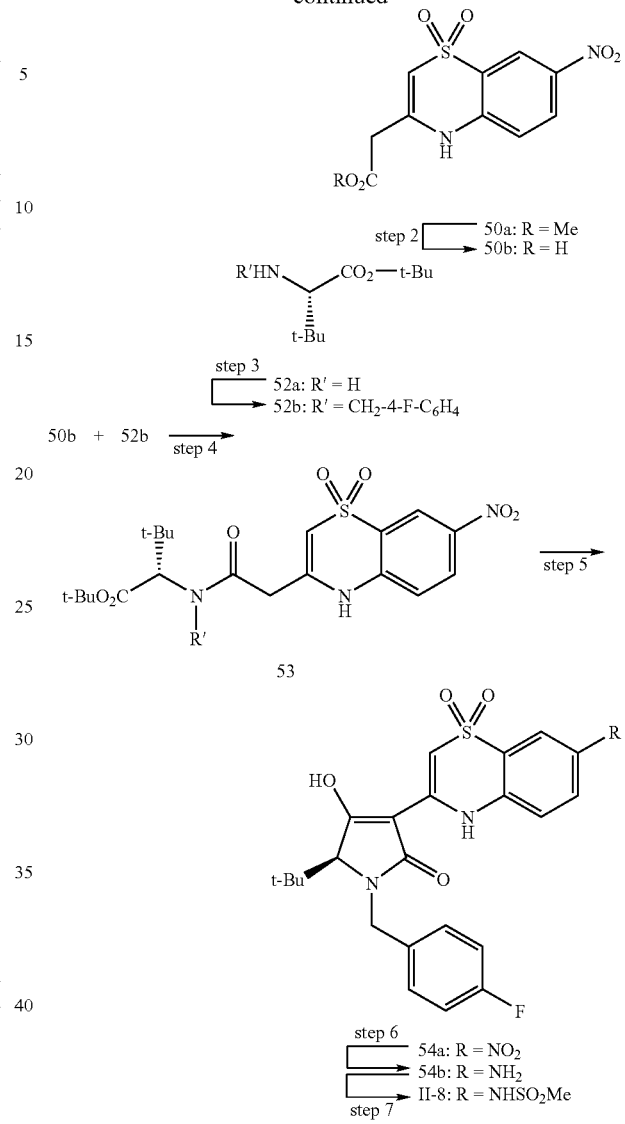

(7-Nitro-4H-benzo[1,4]thiazin-3-yl)-acetic acid ethyl ester (49) was prepared as described in in step 2 of example 7 except ethyl chloro acetocetate was replaced with methyl chloro acetoacetate.

step 1—To a mixture of acetone (250 mL) and THF (50 mL) was added the 49 (5 g, 16.4 mmol) and HCO$_2$H (7.6 g, 164 mmol). The mixture was cooled to 2° C. using an ice bath and KMnO$_4$ (6.5 g, 41 mmol) was added with vigorous stirring. No exotherm was observed. The reaction was warmed to 10° C. and maintained there with an 8° C. water bath. A slight exotherm was observed for approximately 30 min. The reaction was warmed to RT over 1 h, and stirred for an additional 2 h. The acetone and formic acid were removed under reduced pressure. Water (200 mL) and EtOAc (200 mL) were added. The mixture was filtered and the solid was washed with water and EtOAc. The filtrate was poured into a separatory funnel and the layers separated. The organic layer was washed with 1M HCl, saturated NaHCO$_3$ and brine, dried (MgSO$_4$), filtered and evaporated. The product was purified by column chromatography on SiO$_2$ eluting with DCM/MeOH to afford 2.75 g (50%) of 50a:LCMS RT 2.26 min, [M+H].

step 2—A solution of 50a (2.75 g, 9.22 mmol) in MeOH (28 mL) and 1N NaOH (28 mL) was stirred at RT for 30 min. The methanol was removed under reduced pressure, and the mixture was carefully acidified. The resulting solid was collected, washed with water and EtOAc, and dried to afford 1.75 g (67%) of 50b: LCMS RT 2.11 min, does not ionize.

step 3—To a solution of 52a (1.0 g, 4.5 mmol) in DCM (50 mL) containing 5% HOAc was added 4-fluorobenzaldehyde (0.83 g, 6.7 mmol). This mixture was stirred at RT for 4 h. NaBH(OAc)$_3$ (1.89 g, 8.94 mmol) was added and the mixture stirred at RT for an additional 1 h. The reaction mixture was evaporated and dissolved in EtOAc (100 mL). The organic phase was washed with 1N NaOH (100 mL), brine (100 mL), and dried (MgSO$_4$). The solvent was removed under reduced pressure to afford 0.73 g (55%) of 52b: LCMS RT 2.75 min, [M+H].

step 4—To a solution of 50b (0.104 mg, 0.35 mmol) and 52b (0.100 mg. 0.35 mmol) in DMF (20 mL) was added DCC (0.044 mg, 0.35 mmol). The mixture was stirred at RT for 1 h, poured into 1N HCl (50 mL), and extracted into EtOAc (100 mL). The organic phase was washed with brine, dried (MgSO$_4$), filtered and evaporated to afford 0.20 g (100%) of 53: LCMS RT 3.66 min, [M−H].

step 5—To a suspension of 53 (0.20 mg, 0.35 mmol) in IPA (10 mL) was added sodium tert-butoxide (0.84 mg, 0.88 mmol). The reaction mixture was stirred at RT overnight and poured into 1N HCl (20 mL). The resulting solid was collected, washed with DCM, and the mother liquid was collected. The organic layer was washed with acidic brine, dried (MgSO$_4$), filtered and the solvents evaporated under reduced pressure. A solid was collected from DCM/hexane to afford 0.085 g (45%) of 54a: LCMS RT 2.68 min, [M−H].

step 6—The nitro compound 54a (0.51 g, 1.05 mmol) was dissolved in absolute EtOH (45 mL), and activated Raney Nickel (1 mL, suspension in water) was added. The reaction flask was thrice purged with nitrogen. Hydrogen was added and removed three times. The mixture was rapidly stirred for 30 min under hydrogen balloon. The mixture was filtered and the solvent was removed under reduced atmosphere to afford 0.41 g (85%) of 54b: LCMS RT 2.52 min, [M−H].

step 7—A solution of 54b (0.200 g, 0.44 mmol) in pyridine (20 mL) was cooled to 0° C. Methanesulfonyl chloride (0.100 g, 0.87 mmol) was added and the mixture stirred at 0° C. for 1 h. The mixture was acidified with 1N HCl, and the product was extracted into EtOAc. The organics were washed with brine, dried (MgSO$_4$), filtered and concentrated under reduced pressure. The product was purified by column chromatography on SiO$_2$ eluting with EtOAc/hexanes, and then re-purified on an SiO$_2$ column eluting with DCM/MeOH to afford 70 mg (55%) of II-8: LCMS RT 2.39 min, [M−H].

N-{3-[5-tert-Butyl-1-(4-fluoro-3-methyl-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide was prepared by a similar procedure except 4-fluoro-benzaldehyde was replaced with 4-fluoro-3-methyl-benzaldehyde which afforded II-9.

N-{3-[(S)-5-tert-Butyl-1-(4-fluoro-3-methoxy-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide was prepared by a similar procedure except 4-fluoro-benzaldehyde was replaced with 4-fluoro-3-methoxy-benzaldehyde which afforded II-10.

N-{3-[(S)-5-tert-Butyl-1-(3-chloro-4-fluoro-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide was prepared by a similar procedure except 4-fluoro-benzaldehyde was replaced with 3-chloro-4-fluoro-benzaldehyde which afforded II-11.

EXAMPLE 19

1-tert-Butyl-4-(1,1-dioxo-1,4-dihydro-1λ$^6$-benzo[1,4]thiazin-3-yl)-2-(4-fluoro-benzyl)-5-hydroxy-1,2-dihydro-pyrazol-3-one (II-17)

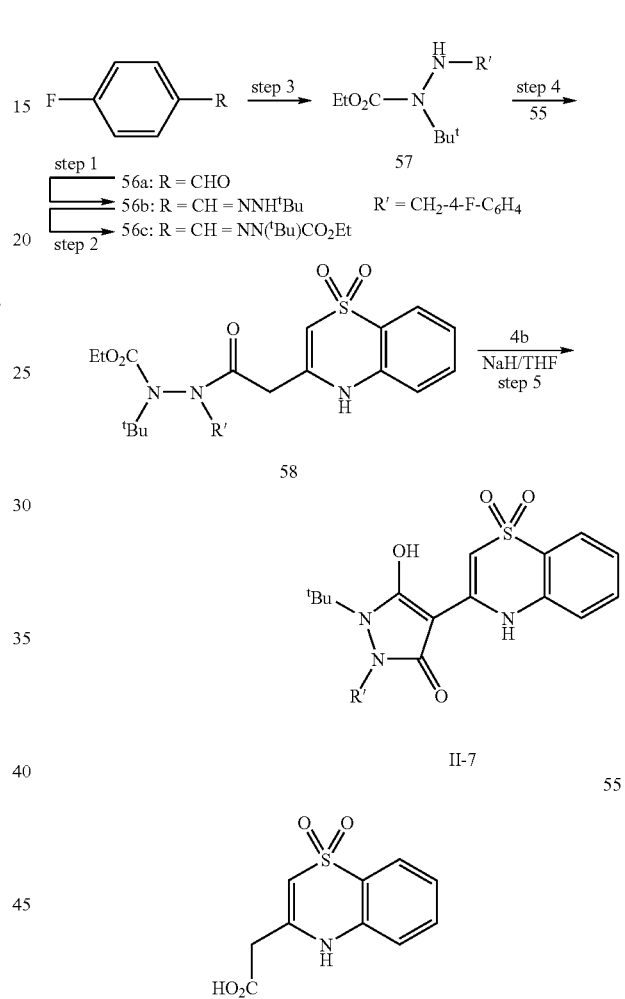

step 1—To a suspension of 1-tert-butylhydrazine hydrochloride (5.0 g, 40 mmol) in ether (200 mL) was added TEA (5.6 mL, 40 mmol) and 4-fluorobenzaldehyde (5.0 g, 40 mmol). After stirring at RT for 30 min, MgSO$_4$ (5.8 g, 48 mmol) was added. The resulting reaction mixture was stirred at RT for 2 days and filtered. The filtrate was evaporated under reduced pressure to afford 7.0 g (90%) of 56b which was taken directly into the next step.

step 2—To a solution of the hydrazone 56b (3.97 g, 20.5 mmol) in EtOAc (100 mL) was added pyridine (1.6 g, 20.5 mmol) followed by ethyl chloroformate (1.96 mL, 20.5 mmol). After stirring at RT for 1 h, the reaction mixture was filtered. The filtrate was evaporated under reduced pressure to afford 5.2 g (96%) of 56c which was taken directly into the next step: LCMS RT 3.8 min, M-(tert-butyl).

step 3—To a solution of the hydrazone 56c (2.0 g, 7.5 mmol) and MeOH (50 mL) was added 10% Pd/C (80 mg, 0.75 mmol). The reaction mixture was hydrogenated at RT for 2 h under 1 atm of hydrogen. After removal of the palladium hydride by filtration, the MeOH was removed under reduced pressure. The resulting yellow oil was taken up in EtOAc, washed with water, dried (MgSO$_4$), filtered and the solvent was removed under reduced pressure. The product was purified by column chromatography on SiO$_2$ eluting with EtOAc/hexanes to afford 1.6 g (80%) of 57: LCMS RT 3.8 min, [M+H].

step 4—To a solution of (1,1-dioxo-1,4-dihydro-1λ$^6$-benzo[1,4]thiazin-3-yl)-acetic acid (55, 240 mg, 1.0 mmol) and a 1:1 mixture of DCM:DMF (5 mL) was added DCC (210 mg, 1.0 mmol) followed by hydrazine 57 (228 mg, 0.85 mmol). After stirring for 2 h at RT, the urea by-product was filtered off and the filtrate concentrated under reduced pressure. The product was purified by column chromatography on SiO$_2$ eluting with EtOAc/hexanes to afford 0.052 g (12%) of 58: LCMS RT 3.5 min, [M–H].

step 5—To a solution of 58 (100 mg, 0.20 mmol) in THF (1 mL) was added NaH (25 mg, 0.61 mmol). The reaction mixture was heated at reflux for 30 min, quenched with saturated aqueous NH$_4$Cl and extracted into EtOAc (2×). The combined organics were dried (Na$_2$SO$_4$), filtered and the solvent was removed under reduced pressure. The product was purified by reverse-phase column chromatography eluting with MeCN/water to afford 55 mg (61%) of II-17: LCMS RT 2.2 min, [M–H].

EXAMPLE 20

N-{3-[7-(4-fluoro-benzyl)-4-hydroxy-2-methyl-6-oxo-6,7-dihydro-thieno[2,3-b]pyridin-5-yl]-1,1-dioxo-1,4-dihydro-1λ$^6$-benzo[1,4]thiazin-7-yl}-methanesulfonamide (I-74)

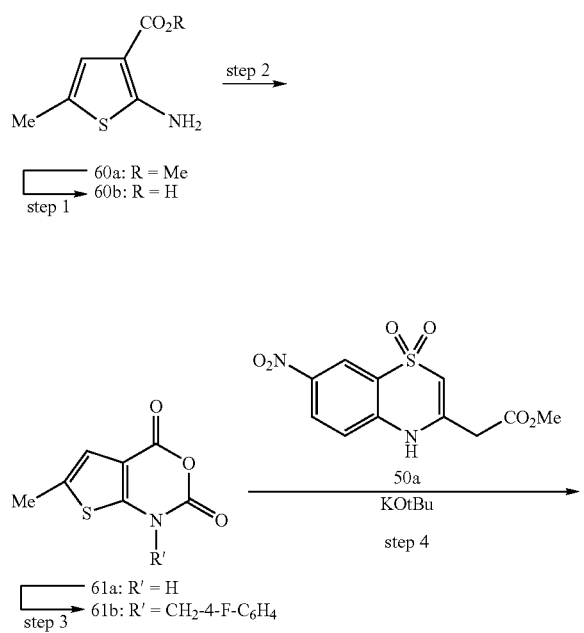

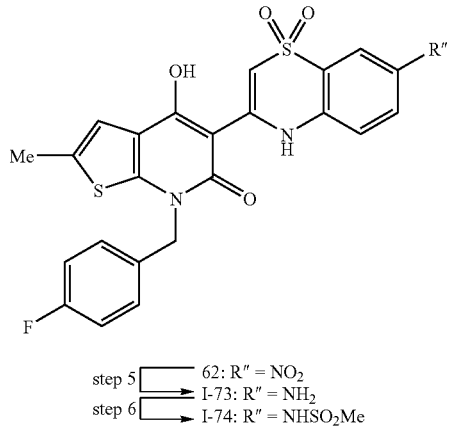

step 5 ⎡ 62: R″ = NO$_2$
       ⎣→ I-73: R″ = NH$_2$
step 6 ⎣→ I-74: R″ = NHSO$_2$Me step 1—2-Amino-5-methyl-thiophene-3-carboxylic acid methyl ester (60a, 5.0 g, 29.2 mmol) was placed in a 250 mL round-bottom flask equipped with a stir bar and suspended in 100 mL of a 3:2:1 mixture of THF, MeOH and water. Lithium hydroxide monohydrate was dissolved in 85 mL of water and added to the flask with stirring. The flask was equipped with a condenser and the mixture was heated at 85° C. for 2 h. After cooling, the THF and MeOH were evaporated, EtOAc was added, and the organic and aqueous layers were separated. The aqueous layer was acidified to pH 4 with 1M HCl and extracted with EtOAc. The organic layer was dried (Na$_2$SO$_4$), filtered and concentrated to give 4.0 g (87%) of 2-amino-5-methyl thiophene-3-carboxylic acid (60b) which was used without purification: ms [M–H]=156.

step 2—A suspension of 60b (4.0 g, 25.5 mmol) and dioxane (65 mL) was cooled to 5° C. Phosgene (22.5 mL of a 20% solution in toluene, 45.9 mmol) was added dropwise through a septum. The flask was equipped with a condenser and the mixture was refluxed for 4 h. After cooling the solvents were evaporated in vacuo to afford 5.0 g (100%) of 6-methyl-1H-thieno[2,3-d][1,3]oxazine-2,4-dione (61a) which was used without purification: ms [M–H]=182.

step 3—Sodium hydride (1.5 g of a 60% dispersion in mineral oil, 37.5 mmol) was suspended in DMF (50 mL) in a 250 mL round-bottom flask equipped with a stir bar, and cooled to 0° C. and maintained under a nitrogen atmosphere. A solution of 61a (4.6 g, 25 mmol) dissolved in DMF (50 mL) was added dropwise through a septum. The flask was removed from the ice bath and the mixture was stirred at RT for 30 m. The reaction was cooled to 10° C. and 1-bromomethyl-4-fluoro-benzene (3.74 mL, 30 mmol) was added through the septum. The flask was removed from the ice bath and the mixture was stirred at RT for 2 h. The reaction was poured into ice and 1N HCl, extracted twice with EtOAc, dried (Na$_2$SO$_4$), filtered and concentrated. A solid was precipitated from the EtOAc by addition of Et$_2$O and hexanes to afford 3.0 g (41%) of 1-(4-fluoro-benzyl)-6-methyl-1H-thieno[2,3-d][1,3]oxazine-2,4-dione (61b): ms 2[M+Na]=605.

step 4—A 50 mL RB flask was charged with 50a (387 mg, 1.3 mmol) and THF (15 mL). The flask was purged with argon, the solution was cooled to 0° C. and of potassium t-butoxide (1.6 mL of a 1M solution in THF) was added. The mixture was stirred at RT for 10 min. To the THF solution was added solid 1-(4-fluoro-benzyl)-6-methyl-1H-thieno[2,3-d][1,3]oxazine-2,4-dione (416 mg, 1.4 mmol). The reaction was stirred at RT under argon overnight. The reaction was quenched by adding HCO₂H (0.5 mL) and Et₂O (13 mL) was added. The resulting precipitate was filtered and washed with Et₂O. The mother liquor was concentrated and precipitated solid was again filtered and washed with Et₂O. This process was repeated once again to afford 637 mg (95%) of 62 which was used without purification: ms [M–H]=512.

step 5—To a suspension of 62 (636 mg, 1.24 mmol) and absolute EtOH (10 mL) was added Sn(II)Cl₂ (1.17 g, 6.2 mmol) and 1M HCl (0.5 mL) and the resulting mixture heated at reflux for 3 h. After cooling, the EtOH was evaporated and 10 mL each of EtOAc and TEA were added to the flask. The mixture was stirred at RT for several min, filtered through CELITE®, and the pad washed with several portions of EtOAc. The filtrate was concentrated, redissolved in EtOAc, and filtered again through CELITE®. The filtrate was washed with saturated aqueous NaHCO₃, water and brine. The extracts were dried (Na₂SO₄), concentrated, and triturated with diethyl ether to afford 208 mg (35%) of I-73 which was used without further purification: ms [M–H]=482.

step 6—To a suspension of I-73 (208 mg, 0.43 mmol) in pyridine (2 mL) cooled to 0° C. was added solid DMAP (53 mg, 0.43 mmol) and MeSO₂Cl (67 µL, 0.86 mmol) was added dropwise through a septum. The reaction was stirred at 0° C. for 30 min. The pyridine was evaporated and the residue partitioned between EtOAc and 1M HCl. The organic layer was washed with water and brine, dried (Na₂SO₄), filtered and concentrated. Preparative TLC plates were run in 10% MeOH/DCM to remove an undesired higher molecular weight side product. The remaining material was extracted from the silica with 10% MeOH/DCM and the solution concentrated. The residue was dissolved in THF (2 mL) and a solution of NaOH (40 mg in 1 mL of H₂O) was added to hydrolyze a portion of the crude reaction mixture which was bis-sulfonylated. The solution was stirred at RT for 2 h, acidified with 1M HCl, extracted with EtOAc, dried (Na₂SO₄), filtered and concentrated. The residue was triturated with diethyl ether to afford 30 mg (12%) of N-{3-[7-(4-fluoro-benzyl)-4-hydroxy-2-methyl-6-oxo-6,7-dihydro-thieno[2,3-b]pyridin-5-yl]-1,1-dioxo-1,4-dihydro-1λ⁶-benzo[1,4]thiazin-7-yl}-methanesulfonamide (I-74) as a yellow powder: ms [M+H]=562.

Compounds I-43, I-46, I-53, I-56, I-60 and I-61 were prepared as described in Example 20 except in step 4, 61b was replaced by 6-fluoro-1-(4-fluoro-benzyl)-1H-benzo[d][1,3]oxazine-2,4-dione and in step 7 methanesulfonyl chloride was replaced by ethylsulfonyl chloride, n-propylsulfonyl chloride, cyclopropylsulfonyl chloride, benzylsulfonyl chloride, iso-propylsulfonyl chloride and n-butylsulfonyl chloride respectively.

EXAMPLE 21

N-{3-[7-(4-fluoro-benzyl)-4-hydroxy-6-oxo-6,7-dihydro-thieno[2,3-b]pyridin-5-yl]-1,1-dioxo-1,4-dihydro-1λ⁶-benzo[1,4]thiazin-7-yl}-methanesulfonamide (I-75)

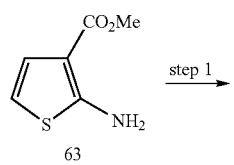

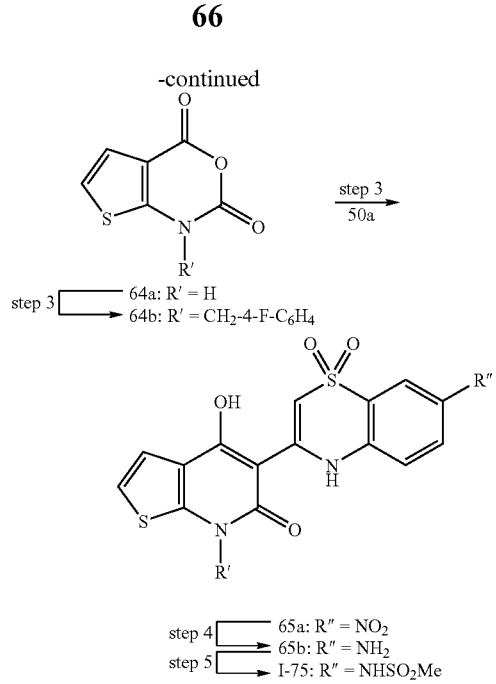

1H-thieno[2,3-d][1,3]oxazine-2,4-dione was prepared as described in *Tetrahedron* 1998 54:10789-10800 which afforded 1.08 g (64%) of 64a which was used without further purification: ms [M–H]=168. 1-(4-Fluoro-benzyl)-1H-thieno[2,3-d][1,3]oxazine-2,4-dione was prepared as described in *Tetrahedron* 1999 55:6167-7174 except benzyl bromide was replaced with 1-bromomethyl 4-fluoro-benzene to afford 850 mg (47%) of 64b which was used without further purification.

step 3—A 50 mL RB flask was charged with 50a (0.500 g, 1.68 mmol) and THF (17 mL). The flask was purged with argon and cooled to 0° C. A solution of potassium t-butoxide in THF (2.0 mL of a 1M solution) was added dropwise. The mixture was stirred at RT for 30 min. To the resulting solution was added 64b (464 mg, 1.68 mmol). The reaction was stirred at RT under argon for 24 h. The reaction was quenched with 0.1 mL of formic acid and 20 mL of Et₂O was added. The precipitate which formed was filtered and washed with Et₂O to afford 415 mg (50%) of 65a: ms [M–H]=498.

step 4—A flask was charged with 65a (400 mg, 0.8 mmol) and 2.0M ammonia in MeOH (8 mL). The flask was purged thoroughly with argon. A quantity of Raney nickel was added to the flask with a pipette and the flask was purged with hydrogen three times. The reaction was stirred at RT under a hydrogen balloon overnight. After purging the flask with argon, the reaction mixture was filtered through filter paper and washed with MeOH and water. The solvents were evaporated and 1M HCl and EtOAc were added. The layers were separated and the organic layer was dried (Na₂SO₄), concentrated and triturated with Et₂O to afford 75 mg (20%) of 65b which was used without purification: ms [M–H]=468.

step 5—To a suspension of 65b (0.069 g, 0.15 mmol) and MeCN (1.5 mL) was added methanesulfonic anhydride (64 mg, 0.36 mmol) and the reaction was heated at reflux for 2 h, then stirred at RT overnight. The mixture was partitioned between saturated aqueous NaHCO₃ and EtOAc. The organic layer was dried (Na₂SO₄), filtered and concentrated. Preparative TLC plates were run in 10% MeOH/DCM. The product was extracted from the silica with 10% MeOH/DCM, concentrated and triturated with Et$_2$O to afford 13 mg (16%) of I-75: ms [M–H]=546.

EXAMPLE 22

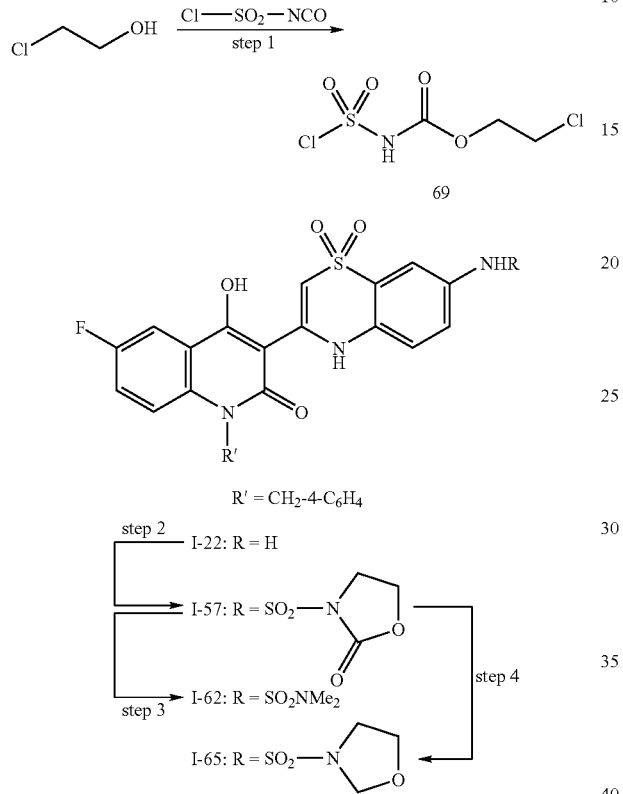

step 1—To a solution of the sulfonyl isocyanate (1.35 g, 9.7 mmol) in MeCN (10 mL) cooled to 0° C. was added chloroethanol (0.65 mL, 9.74 mmol) in one portion. The reaction was stirred at 0° C. for 30 min then at RT for an additional 1 h. The MeCN solution of 69 was used in the next reaction.

step 2—To a solution of the I-22 (0.7 g, 1.5 mmol) in MeCN (100 mL) was added the solution of 69 from step 1 (1.5 mL), followed by N-methyl morpholine (0.44 g, 4.4 mmol). The reaction was stirred at RT for 1 h and heated to 50° C. for 4 h. The reaction was diluted with EtOAc, and the organics washed with brine, dried (MgSO$_4$), and concentrated under reduced pressure. The product was purified by SiO$_2$ chromatography eluting with acetone/HCO$_2$H/hexanes to afford 0.57 g (62%) of I-57: LCMS RT 2.92 min, [M–H].

step 3—To a solution of I-57 (0.050 g, 0.08 mmol) in THF (20 mL) was added a solution of dimethylamine (0.4 mL, 0.8 mmol) in THF. The reaction was heated at 140° C. in a sealed tube for 16 h, cooled, and then the solvents removed under reduced pressure. The crude mixture was purified by HPLC (Horizon): first with a C$_{18}$ column and a linear 5-80% acetonitrile/water gradient (TFA buffered), and then with a silica column and a linear 0-10% MeOH/DCM gradient to afford 4.6 mg (9.8%) of I-62: LCMS RT 2.93 min, [M–H].

step 4—I-65 was prepared by the method described in step 2 except dimethylamine was replaced by pyrrolidine to afford 0.6 mg (1.23%) of I-65: LCMS RT 3.08 min, [M–H].

EXAMPLE 23

6-Fluoro-1-(4-fluoro-benzyl)-4-hydroxy-3-(7-methoxymethyl-1,1-dioxo-1,4-dihydro-1$\lambda^6$-benzo[1,4]thiazin-3-yl)-1H-quinolin-2-one (I-68)

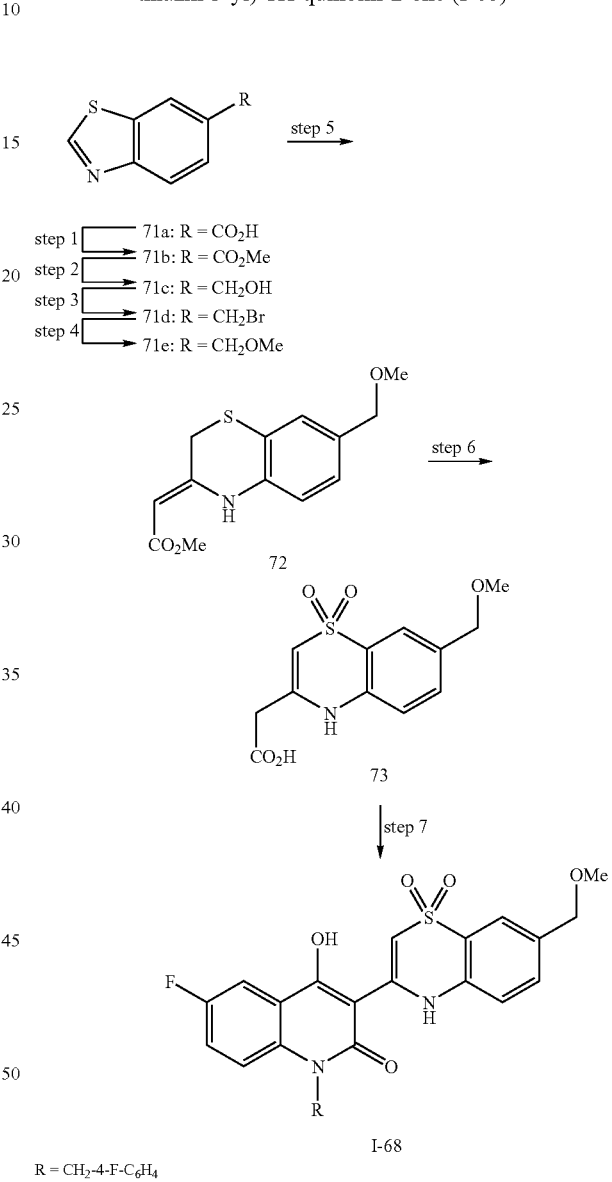

step 1—Benzothiazole-6-carboxylic acid (71a, 5.0 g, 27.93 mmol) was dissolved in DCM (96 mL) and MeOH (32 mL) and cooled to 0° C. A solution of trimethylsilyl-diazomethane (28 mL, 2.0M in hexane) was added dropwise and the resulting solution was gradually warmed to RT and stirred overnight. The reaction was quenched slowly by careful addition of HOAc (2 mL) and stirred for 30 min. The solution was concentrated, diluted with EtOAc and washed with saturated NaHCO$_3$ solution. The organic extracts were dried (Na$_2$SO$_4$), filtered and concentrated in vacuo. The crude residue was purified by SiO$_2$ chromatographed eluting with 15% EtOAc/ hexane to afford 4.44 g (82%) of 71b as a white solid: $^1$H NMR (300 MHz, CDCl$_3$): 9.15 (s, 1H), 8.68 (m, 1H), 8.16 (m, 2H), 3.97 (s, 3H).

step 2—To a solution of 71b (194 mg, 1.01 mmol) and DCM (4 mL) cooled to −78° C. was added dropwise DIBAL-H (3.0 mL, 1.0M in DCM) and the resulting solution was gradually warmed to RT and stirred overnight. The reaction mixture was cooled to 0° C., carefully quenched with a saturated sodium potassium tartrate solution and stirred for 1 h. The solution was thrice extracted with DCM and the combined organic extracts were dried (Na$_2$SO$_4$), filtered and concentrated in vacuo. The crude residue was chromatographed on SiO$_2$ eluting with 35% EtOAc/hexane to afford 100 mg (61%) of 71c as a yellow oil (61%): $^1$H NMR (300 MHz, CDCl$_3$): 8.95 (s, 1H), 8.07 (d, 1H, J=8.4 Hz), 7.96 (s, 1H), 7.47 (dd, 1H, J=8.4, 1.7 Hz), 4.84 (s, 2H).

step 3—To an ice-cold solution of 71c (607 mg, 3.68 mmol), CBr$_4$ (1.33 g, 4.02 mmol) and DCM (4 mL) was added dropwise a solution of triphenylphosphine (1.05 g, 4.01 mmol) in DCM (4 mL). The resulting solution was gradually warmed to RT and stirred overnight. The crude reaction mixture was concentrated and chromatographed on SiO$_2$ eluting with a EtOAc/hexane gradient (10 to 15% EtOAc) to afford 430 mg (51%)of 71d as white solid: $^1$H NMR (300 MHz, CDCl$_3$): 9.02 (s, 1H), 8.10 (d, 1H, J=8.5 Hz), 7.99 (d, 1H, J=1.8 Hz), 7.55 (1H, dd, J=8.5 Hz, 1.8 Hz), 4.65 (s, 2H).

step 4—A solution of 71d (430 mg, 1.89 mmol) and MeOH (7.5 mL) was cooled to 0° C. and a solution of sodium methoxide (7.5 mL, 0.5M in methanol) was added dropwise. The resulting solution was stirred overnight at RT. The reaction mixture was concentrated, diluted with EtOAc and neutralized with 1N HCl. The organic layer was separated, dried (Na$_2$SO$_4$), filtered and concentrated in vacuo to afford 308 mg (91%) of 71e as a tan oil: $^1$H NMR (300 MHz, CDCl$_3$): 8.99 (s, 1H), 8.10 (d, 1H, J=8.4 Hz), 7.94 (m, 1H), 7.47 (dd, 1H, J=8.4 Hz, 1.7 Hz), 4.60 (s, 2H), 3.42 (s, 3H).

step 5—To a solution of 71e (308 mg, 1.676 mmol) and EtOH (5 mL) was added freshly powdered KOH (228 mg, 4.071 mmol). The solution was heated at reflux overnight. The solution was cooled to 0° C. and 4-chloro-acetoaceticacid methyl ester (220 μL, 1.900 mmol) was added dropwise via syringe. The resulting solution was gradually warmed to RT and stirred overnight. The reaction mixture was concentrated, diluted with EtOAc, and washed with 1N HCl and brine. The organic extracts were dried (Na$_2$SO$_4$) and concentrated in vacuo. The crude product was purified by SiO$_2$ chromatography eluting with a EtOAc/hexane gradient (1% to 5% EtOAc) to afford 266 mg (60%) of 72 as a colorless oil which solidified on standing (60%): $^1$H NMR (300 MHz, CDCl$_3$): 10.61 (s, 1H), 7.19 (d, 1H, J=1.8 Hz), 7.09 (dd, 1H, J=6.1 Hz, 1.9 Hz), 6.86 (d, 1H, J=8.1 Hz), 4.71 (s, 1H), 4.35 (s, 2H), 3.72 (s, 3H), 3.41 (s, 2H), 3.37 (s, 3H).

step 6—The thiazine ester 72 was oxidized with KMnO$_4$ as described in step 1 of example 18 to afford 73: ms [M+H]=298, [M−H]=296.

step 7—The condensation of 22 and 73 was carried out as described in example 2 to afford I-68: ms [M+H]=511, [M−H]=509.

EXAMPLE 24

3-(1,1-Dioxo-1,4-dihydro-1λ$^6$-benzo[1,4]thiazin-3-yl)-4-hydroxy-6-methyl-5-phenyl-1H-pyridin-2-one (III-1)

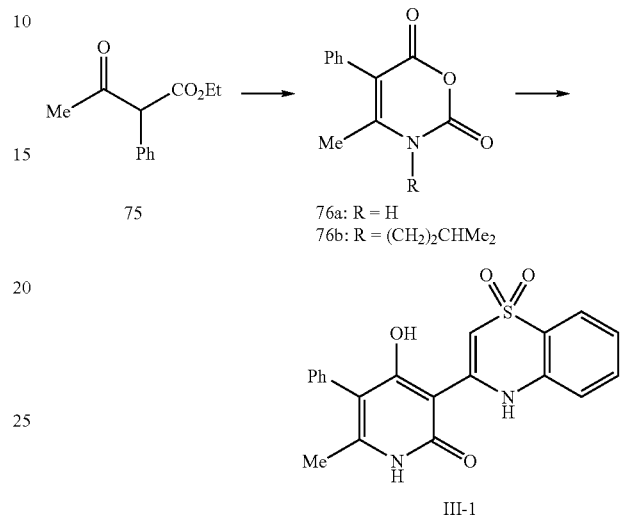

step 1—A 100 mL RB flask was charged with 75 (2.5 g, 12.6 mmol), urethane (1.08 g, 12.1 mmol) and POCl$_3$ (10 mL). The reaction was heated to 90° C. for 2.5 h at which time the starting material undetectable by TLC. The volatiles components were removed in vacuo (80° C. bath temperature) and the purple residue was partitioned between toluene (100 mL) and water (100 mL) with sonication. The aqueous layer was extracted with EtOAc (3×100 mL). The combined organic phases were concentrated to afford 1.715 g (70%) of 76a as a light yellow solid: LCMS RT 1.95 min, [M−H].

step 2—The oxazine-2,6-dione 76a (406 mg, 2 mmol) was weighed into a 50 mL 1-neck flask and dissolved in DMA (20 mL). The solution was maintained under a N$_2$ atmosphere and NaH (80 mg, 2 mmol, 60% dispersion in mineral oil) was added in one portion. The reaction mixture was stirred for 20 min after which isoamyl bromide (302 mg, 2 mmol) was added and the resulting mixture was heated to 80° C. overnight. The reaction was then quenched with water (2 mL), stirred for 20 minutes at RT, then loaded directly to a SiO$_2$ column and eluted wit 20% EtOAc/hexanes, to afford 398 mg (73%) of 76b as a yellow oil: LCMS RT 3.21 min, [M−H].

step 3—To a solution of 76b (91 mg, 0.33 mmol), 4 (89 mg, 0.33 mmol) and THF (3.5 mL) was added in one portion NaH (26 mg, 0.66 mmol) was then added in one portion. After the evolution of N$_2$ subsided the flask was fitted with a reflux condenser, and heated to 80° C. under a N$_2$ atmosphere. The reaction was subsequently monitored by LCMS. When 76b was not longer detectable by hplc the reaction was cooled to RT and glacial HOAc (500 μL) and 1 N HCl (5.0 mL) were added sequentially. The aqueous phase was then extracted with Et$_2$O (3×50 mL). The combined organic phases were dried (Na$_2$SO$_4$), filtered and concentrated. The crude was then purified by SiO$_2$ chromatography eluting with a EtOAc/ hexane gradient (25-40% EtOAc) to afford 61 mg (41%) of III-1 as a yellow semi-solid: LCMS RT 2.34 min, [M−H].

EXAMPLE 25

Preparation of N-Substituted Isatoic Anhydrides

A. Copper-Catalyzed Displacement

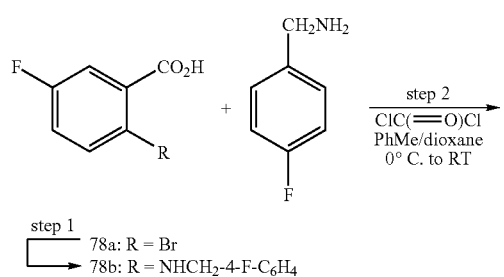

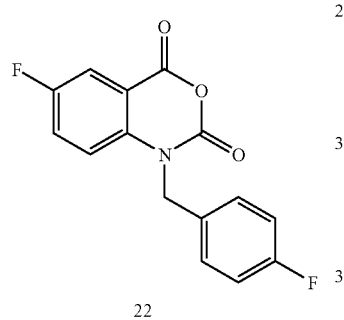

step 1—To a stirred solution of 78a (5 g, 22.8 mmol) in THF (47 mL) maintained under a $N_2$ atmosphere was added $K_2CO_3$ (9.4 g, 68.4 mmol), CuBr (0.25 g, 1.14 mmol); and p-fluorobenzylamine (3 g, 24 mmol) and the mixture stirred at 60° C. overnight. The reaction was cooled in an ice bath and a solution of EDTA.2H$_2$O (0.604 g) and water (22 mL) was added dropwise via addition funnel. The mixture was stirred at RT for an additional 0.5 h after which the THF was evaporated. The residual aqueous solution was cooled to 0° C. and 6N HCl (29 mL) was added dropwise with vigorous stirring. The resulting heterogeneous mixture was stirred overnight, the solid was filtered and washed with copious amounts of H$_2$O then isooctane. The solid was dried in vacuo to afford 5.05 g (84%) of 78b.

step 2—To a solution of 78 (0.5 g, 1.9 mmol) in dioxane (5 mL) under a $N_2$ atmosphere and cooled to 0° C., was added dropwise phosgene (5 mL, 20% solution in toluene). The solution was allowed to stir to RT overnight. The phosgene was evaporated and EtOAc/hexane (10 mL, 1:4) was added with vigorous stirring. Stirring was continued overnight and the resulting solid was filtered, washed with hexane, air dried and recrystallized from hexane/EtOAc to afford 0.467 g (85%) of 22.

B. N-alkylation

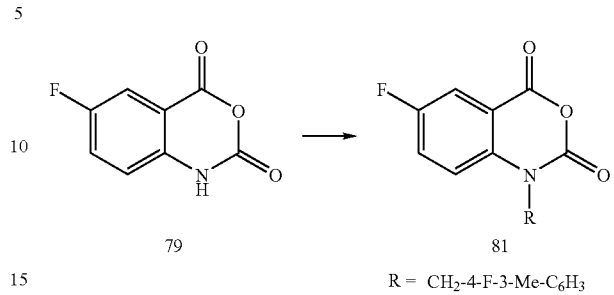

6-fluoroisatoic anhydride (79, 0.6 g, 3.3 mmol) was dissolved in anhydrous N,N-dimethylacetamide (16 mL). The solution was stirred under an $N_2$ atmosphere and NaH (0.146 g, 3.64 mmol, 60% dispersion in mineral oil) was added. The mixture was stirred for 10 min and then 4-fluoro-3-methylbenzyl bromide (0.74 g, 3.64 mmol) was added. The reaction was heated to 70° C. for 2 h, cooled to RT, and then in an ice bath. The cold reaction mixture was poured into a cold saturated NH$_4$Cl solution (100 mL) and extracted twice with Et$_2$O/EtOAc (100 mL). The combined ether solutions were washed with water (30 mL), saturated NaCl solution and dried (Na$_2$SO$_4$). The extracts were filtered and evaporated and the solid was triturated with 10% Et$_2$O/hexanes and vacuum dried to afford 900 mg (90%) of 80: ms [M]$^+$=303; $^1$H NMR (300 MHz, DMSO-d$_6$):δ 7.84 ppm (1H, dd, J=7.4, 3 Hz); 7.37 ppm (1H, m); 7.1 ppm (3H, m); 6.99 ppm (1H, dd, J~9 Hz); 5.22 ppm (2H, s); 2.26 ppm (3H, s).

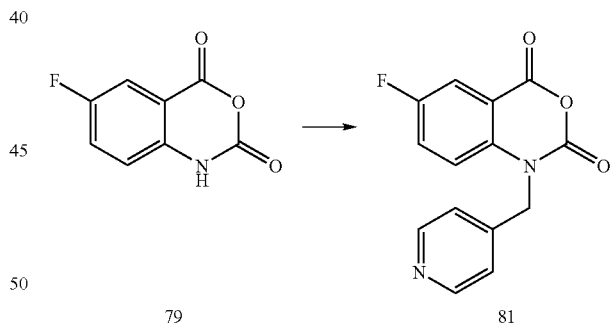

6-fluoroisatoic anhydride (79, 0.3 g, 1.65 mmol) was dissolved in anhydrous DMA (8 mL). The solution was stirred under an $N_2$ atmosphere and NaH (0.073 g, 1.82 mmol, 60% dispersion in mineral oil) was added. The mixture was stirred for 10 min and additional sodium hydride (0.066 g, 1.65 mmol) was added followed by a solution of 4-(bromomethyl)pyridine hydrobromide (0.46 g, 1.82 mmol) and DMA (10 mL). The reaction was heated to 70° C. for 3 h, cooled to room temperature and finally in an ice bath. The reaction mixture was poured into a cold saturated NH$_4$Cl solution (150 mL) and thrice extracted with EtOAc (75 mL). The combined organic layers were washed with water (40 mL), brine. The solution was dried (Na$_2$SO$_4$), filtered and evaporated to afford a solid which was dried in a vacuum then triturated with Et$_2$O/hexane (1:2) to afford 300 mg (66%) of 81: ms [M+H]$^+$ =273.

EXAMPLE 26

HCV NS5B RNA Polymerase Activity

The enzymatic activity of HCV NS5B570n-BK is measured as incorporation of radiolabeled nucleotide monophosphates into acid insoluble RNA products. Unincorporated radiolabel substrate is removed by filtration and scintillant is added to the washed and dried filter plate containing radiolabeled RNA product. The light emitted by the scintillant is proportional to the amount of RNA product generated by NS5B570n-BK at the endpoint of the reaction.

The N-terminally histidine tagged HCV polymerase, derived from HCV BK strain, genotype 1b (NS5B570n-BK) contains a 21 amino acid deletion at the C-terminus relative to the full-length HCV polymerase and is purified from *E. coli* strain M15. The construct containing the coding sequence of HCV BK strain amino acid residues 2421-2999 (GenBank accession number M58335) downstream of a Taq promoter expression cassette was inserted into plasmid constructs. The plasmid constructs are transformed in *E. coli* and colonies are inoculated and grown overnight in 10 L of Terrific broth (Tartoff and Hobbs) supplemented with 100 µg/mL ampicillin at 37° C. Protein expression is induced by addition of 1 mM isopropyl-β-D-thiogalactopyranoside (IPTG), when optical densities reaches between 1.5 and 3.5 OD$_{600}$ and the culture is then incubated for 16- to 18 h at 22° C. NS5B570n-BK is purified to homogeneity using a three step protocol including subsequent column chromatography on Ni-NTA, SP-Sepharose HP and Superdex 75 resins.

Each 50 µl enzymatic reaction contains 8:4 µg/mL polyA: oligo U$_{16}$ (template:primer), 20 nM or 200 nM NS5B570n-BK enzyme, 1 µCi of tritiated UTP (Perkin Elmer catalog no. TRK412; specific activity: 30 to 60 Ci/mmol; stock solution concentration from 7.5×10$^{-5}$ M to 20.6×10$^{-6}$ M), 40 mM Tris-HCl pH 8.0, 2 to 40 mM NaCl, 4 mM DTT (dithiothreitol), 4 mM MgCl$_2$, and 5 µl of compound serial diluted in DMSO. Reaction mixtures are assembled in MADVNOB 96-well filter plates (Millipore Co.) and incubated for 2 h at 30° C. Reactions are stopped by addition of 10% (v/v) trichloroacetic acid and incubated for 40 min at 4° C. Reactions are filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) is added to each reaction well.

The amount of light emitted from the scintillant is converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data is analyzed with GraphPad® Prism® and/or Microsoft® Excel®. The reaction in the absence of enzyme is used to determine the background signal, which is subtracted from the enzymatic reactions. Positive control reactions are performed in the absence of compound, from which the background corrected activity is set as 100% polymerase activity. All data is expressed as a percentage of the positive control. The compound concentration at which the enzyme-catalyzed rate of RNA synthesis is reduced by 50% (IC$_{50}$) is calculated by fitting equation (i) to $$Y = \% \text{ Min} + \frac{(\% \text{ Max} - \% \text{ Min})}{\left[1 + \frac{X}{(IC_{50})^S}\right]} \quad \text{(i)}$$

the data, where "Y" corresponds to the relative enzyme activity (in %), "% Min" is the residual relative enzymatic activity at saturating compound concentration, "% Max" is the maximal relative enzymatic activity compared to positive control, X corresponds to the compound concentration, and "S" is the Hill coefficient (or slope).

Alternatively the assay can be run as described above with the following modifications. The polyA:oligo U$_{16}$ homopolymeric RNA template:primer is replaced by the heteropolymeric cIRES RNA template at concentrations of 20 nM or 200 nM. The cIRES RNA template is derived from the complementary sequence of the Internal Ribosome Entry site of the HCV genome (nucleotide 1 through 378 at the 5'-end of the negative strand of the HCV genome (EMBL database accession number AJ238799). The reaction mixture is supplemented with 1 µM ATP, CTP, and GTP

EXAMPLE 27

*Renilla* Luciferase Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla* luciferase gene was introduced into the first open reading frame of a replicon construct NK5.1 (Krieger et al., *J. Virol.* 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 contain replicative HCV subgenomic RNA, and the activity of *Renilla* luciferase expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation.

*Renilla* luciferase HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using Dual-Luciferase reporter assay system (Promega cat no. E1960). All the reagents described in the following paragraph were included in the manufacturer's kit, and the manufacturer's instructions were followed for preparations of the reagents. The cells were washed twice with 200 µl of phosphate buffered saline (pH 7.0) (PBS) per well and lysed with 25 µl of 1× passive lysis buffer prior to incubation at room temperature for 20 min. One hundred microliter of LAR II reagent was added to each well. The plate was then inserted into the LB 96V microplate luminometer (MicroLumatPlus, Berthold), and 100 µl of Stop & Glo® reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microliter of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

TABLE 5

| Compound Number | Polymerase Assay $IC_{50}$ (µM) | LuciferaseActivity $IC_{50}$ (µM) |
| --- | --- | --- |
| I-24 | 0.1507[1], 0.067[2], 0.0055[3] | 0.013 |
| I-20 | 0.15[1] | 1.053 |
| I-32 | 0.22[1], 0.0073[3] | 0.005 |
| I-40 | 0.35[1] | 0.009 |
| I-69 | 0.0144[3] | 0.015 |
| II-11 | 0.0046[3] | 0.009 |

[1]200 nM polyA: oligo $U_{16}$,
[2]200 nM cIRES,
[3]20 nM cIRES

EXAMPLE 28

Pharmaceutical compositions of the subject Compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | q.s. to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 mL |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

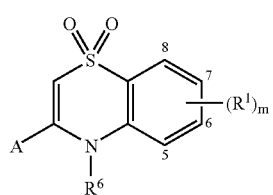

(I)

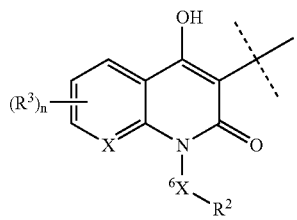

A-1

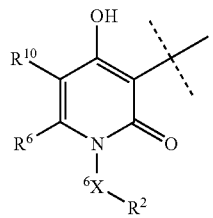

A-2

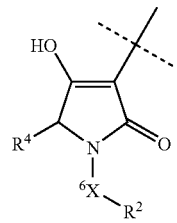

A-3

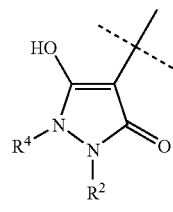

A-4

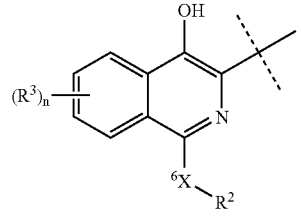

A-5

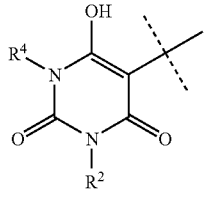

A-6

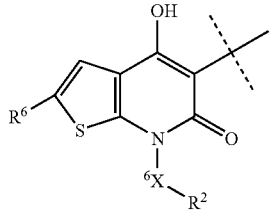

A-7

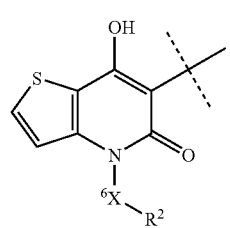

A-8 wherein:

A is selected from the grouping consisting of A-1, A-2, A-3, A-4, A-5, A-6, A-7 and A-8;

X is CH or N;

$X^6$ is —O—, —$NR^6$— or $X^6$ is absent;

$R^1$ in each incidence is independently selected from the group consisting of $C_{1-6}$ alkyl, $C_{2-6}$ alkenyl, $C_{2-6}$ alkynyl, $C_{3-7}$ cycloalkyl, $C_{3-7}$ cycloalkyl-$C_{1-4}$ alkyl, $C_{1-6}$ alkoxy, optionally substituted phenyl, optionally substituted phenyl-$C_{1-6}$ alkyl, $C_{1-6}$hydroxyalkyl, $C_{1-3}$ alkoxy-$C_{1-6}$ alkyl, optionally substituted phenoxy, optionally substituted phenyl-$C_{1-3}$ alkoxy, $C_{1-6}$ heteroalkoxy, hydroxyl, halogen —$X^1(CH_2)_oCOR^5$, —$(CH_2)_oCOR^5$, —$X^1(CH_2)_oSO_2R^7$, —$(CH_2)_oSO_2R^7$, —$X^5C(=O)R^9$, —$NR^6SO_2R^7$, —$X^4(CH_2)_rNR^aR^{b'}$, —$CO_2R^6$, $X^4NR^aR^b$, nitro, and cyano wherein said optionally substituted phenyl groups are substituted with one to three substituents independently selected from the group consisting of $C_{1-3}$ alkyl, $C_{2-4}$ alkenyl, $C_{2-4}$ alkynyl, $C_{1-3}$ alkoxy, phenoxy, $C_{1-3}$ haloalkyl, hydroxy, halogen, $NR^aR^b$, cyano and nitro;

$R^2$ is independently selected from the group consisting of $C_{1-6}$ alkyl, $C_{3-6}$ alkenyl, $C_{3-6}$ alkynyl, pyridinylmethyl, imidazolinylmethyl, $C_{3-7}$ cycloalkyl, $C_{3-7}$ cycloalkyl-$C_{1-3}$ alkyl, $C_{1-6}$ heteroalkyl and phenyl-$C_{1-3}$ alkyl said phenyl optionally substituted with one to three substituents independently selected from the group consisting of $C_{1-3}$ alkyl, $C_{2-4}$ alkenyl, $C_{2-4}$ alkynyl, $C_{1-3}$ alkoxy, phenoxy, $C_{1-3}$ haloalkyl, hydroxy, halogen, $NR^aR^b$, cyano and nitro;

$R^3$ in each incidence is independently selected from the group consisting of $C_{1-6}$ alkyl, $C_{2-6}$ alkenyl, $C_{2-6}$ alkynyl, $C_{3-7}$ cycloalkyl, $C_{3-7}$ cycloalkyl-$C_{1-4}$alkyl, $C_{1-6}$ alkoxy, halogen, $R^4$ is hydrogen, $C_{1-6}$ alkyl, $C_{3-7}$ cycloalkyl, $C_{3-7}$ cycloalkyl-$C_{1-4}$alkyl, $C_{1-6}$ heteroalkyl, phenyl or phenyl-$C_{1-4}$ alkyl said phenyl optionally substituted independently with one to three $R^3$ radicals;

$R^4$ is hydrogen, $C_{1-6}$ alkyl, $C_{3-7}$ cycloalkyl, $C_{3-7}$ cycloalkyl-$C_{1-4}$alkyl, $C_{1-6}$ heteroalkyl, phenyl or phenyl-$C_{1-4}$ alkyl said phenyl optionally substituted independently with one to three $R^3$ radicals;

$R^5$ is hydroxyl, $C_{1-6}$ alkoxy, —$NR^aR^b$, phenyl or $C_{1-6}$ heteroalkoxy;

$R^6$ is hydrogen or $C_{1-6}$ alkyl;

$R^7$ is $C_{1-6}$ alkyl, $C_{3-7}$ cycloalkyl, $C_{3-7}$ cycloalkyl-$C_{1-4}$ alkyl, —$NR^aR^b$, —$NR^6(CH_2)_p$-phenyl, —NHBoc, $C_{1-6}$ heteroalkyl, —$X^2(CH_2)_oCOR^5$, optionally substituted isoxazole, phenyl or phenyl-$C_{1-3}$ alkyl wherein said phenyl and said isoxazole are each optionally substituted independently with one to three $C_{1-3}$ alkyl, $C_{1-3}$ alkoxy, halogen, nitro or cyano;

$R^8$ is $R^6$ or $C_{1-6}$ acyl;

$R^9$ is $C_{1-6}$ alkyl, $C_{3-7}$ cycloalkyl, phenyl, $NR^aR^b$ or $OR^4$ wherein $R^4$ is not hydrogen and said phenyl is optionally substituted with one to three $R^3$ radicals;

$R^{10}$ is phenyl or pyridinyl said phenyl and said pyridinyl are optionally substituted with one to three substituents selected from the group consisting of $C_{1-3}$ alkyl, $C_{1-3}$ alkoxy, $C_{1-3}$ haloalkyl, halogen, $NR^aR^b$, cyano and nitro;

$R^a$ and $R^b$ are (i) independently hydrogen, $C_{1-6}$ alkyl or $C_{1-6}$ heteroalkyl, or (ii) taken together are $(CH_2)_q$, —$(CH_2)_2OC(=O)$— or $(CH_2)_2X^3(CH_2)_2$;

$R^{a'}$ and $R^{b'}$ independently are (i) hydrogen, $C_{1-6}$ alkyl or $C_{1-6}$ heteroalkyl, or (ii) $R^{a'}$ is —$SO_2R^4$, —$SO_2NR^aR^b$ or —$COR^9$ and $R^{b'}$ is hydrogen; or (iii) $R^{a'}$ and $R^{b'}$ taken together are $(CH_2)_q$ or $(CH_2)_2X^3(CH_2)_2$;

$X^1$ is O, $S(O)_p$, $C(=O)$ or $NR^6$;

$X^2$ is $NR^6$ or a bond;

$X^3$ is —O—, C=O or $NR^8$;

$X^4$ is $X^1$ or a bond;

$X^5$ is $NR^6$ or O;

m and n are independently zero to three;

o and r are independently one to six;

p is zero to two;

q is four to seven; and, pharmaceutically acceptable salts thereof.

2. A compound according to claim 1 wherein:

A is A-1-A-5, A-7 or A-8;

$X^6$ is absent;

$R^1$ in each incidence is independently selected from the group consisting of halogen, nitro, cyano, hydroxyl, benzyloxy, $C_{1-3}$ alkoxy, $C_{1-6}$ alkoxy-$C_{1-6}$ alkyl, amino, $C_{1-3}$ alkylamino, $C_{1-6}$ acylamino, $C_{1-6}$ alkylsulfonylamino, $C_{1-6}$ alkylsulfonyl-$C_{1-3}$ alkylamino, $C_{3-7}$ cycloalkylsulfonylamino, amino-$C_{1-3}$ alkyl, $C_{1-3}$ alkylamino-$C_{1-3}$ alkyl, phenylsulfonylamino, benzylsulfonylamino, 3,5-dimethyl-isoxazol-4-yl-sulfonyl-amino, —$OCH_2CONR^cR^d$, $O(CH_2)_2CONR^cR^d$ —$OCH_2CO_2R^c$, —$NHCONR^c$, $NHCO_2$-tert-Bu, and $NHSO_2NR^eR^f$;

wherein:

$R^c$ and $R^d$ are independently hydrogen or $C_{1-3}$ alkyl; and $R^e$ and $R^f$ are independently hydrogen, $C_{1-3}$ alkyl or $CO_2$-tert-Bu or $R^e$ and $R^f$ together are $(CH_2)_4$ and $(CH_2)_2OC(=O)$;

$R^2$ is $C_{1-6}$ alkyl, $C_{1-3}$ alkyl-$C_{3-7}$ cycloalkyl, pyridinylmethyl or phenyl-$C_{1-3}$ alkyl said phenyl optionally substituted with one to three groups independently selected from halogen, cyano, $C_{1-6}$ alkyl, $C_{1-6}$-haloalkyl, $C_{1-6}$ alkoxy;

$R^3$ in each incidence is independently selected in each incidence from the group consisting of halogen, $C_{1-6}$ alkyl or $C_{1-6}$ alkoxy;

m and n are independently zero to two.

3. The compound according to claim 1 wherein A is A-1.

4. The compound according to claim 3 wherein:

$R^1$ in each incidence is independently selected from the group consisting of —$X^1(CH_2)_oCOR^5$, —$(CH_2)_oCOR^5$, —$X^1(CH_2)_oSO_2R^7$, —$(CH_2)_oSO_2R^7$, —$NR^6SO_2R^7$, —$X^4(CH_2)_rNR^aR^{b'}$, —$X^5C(=O)R^9$, $CONR^aR^b$, —$CO_2R^6$, —$NR^aR^b$, halogen, nitro, and hydroxyl;

$R^2$ is $C_{1-6}$ alkyl, optionally substituted phenyl-$C_{1-4}$ alkyl or $C_{3-7}$ cycloalkyl-$C_{1-4}$ alkyl;

$R^3$ in each incidence is independently selected from the group consisting of $C_{1-6}$ alkyl, $C_{1-6}$ alkoxy, halogen, —$NR^aR^b$, $C_{1-6}$ acylamino, $NR^6SO_2R^7$, cyano and nitro;

$R^7$ is $C_{1-6}$ alkyl, $C_{3-7}$ cycloalkyl, $NR^aR^b$, optionally substituted phenyl or phenyl $C_{1-3}$ alkyl;

X is CH;

$X^6$ is absent; and, $X^1$ is O.

5. The compound according to claim 4 wherein $R^1$ in each incidence is independently selected from the group consisting of —$X^1(CH_2)_oCOR^5$, —$NR^6SO_2R^7$, —$X^4(CH_2)_rNR^aR^{b'}$, —$X^5C(=O)R^9$, nitro, —$NR^aR^b$, halogen and hydroxyl.

6. A compound according to claim 4 wherein m is one or two and the 7 and/or the 8 positions is(are) substituted.

7. A compound according to claim 6 wherein $R^1$ in each incidence is independently selected from the group consisting of —$X^1(CH_2)_oCOR^5$, —$NR^6SO_2R^7$, —$X^4(CH_2)_rNR^aR^{b'}$, —$X^5C(=O)R^9$, nitro, —$NR^aR^b$, halogen and hydroxyl.

8. A compound of claim 6 wherein m is one and the 7-position is substituted.

9. A compound according to claim 8 wherein $R^1$ is selected from the group consisting of —$X^1(CH_2)_oCOR^5$, —NR$^6$SO$_2$R$^7$, —X$^4$(CH$_2$)$_r$NR$^a$'R$^{b'}$, —X$^5$C(=O)R$^9$, halogen and hydroxyl, —NR$^a$R$^b$ and nitro.

10. A compound according to claim 9 wherein R$^1$ is NR$^6$SO$_2$R$^7$, nitro or NR$^a$R$^b$.

11. The compound of claim 1 wherein A is A-3.

12. The compound according to claim 11 wherein:
R$^1$ in each incidence is independently selected from the group consisting of —X$^1$(CH$_2$)$_o$COR$^5$, —(CH$_2$)$_o$COR$^5$, —X$^1$(CH$_2$)$_o$SO$_2$R$^7$, —(CH$_2$)$_o$SO$_2$R$^7$, —NR$^6$SO$_2$R$^7$, —X$^4$(CH$_2$)$_r$NR$^a$'R$^{b'}$, —X$^5$C(=O)R$^9$, —CONR$^a$R$^b$, —CO$_2$R$^6$, halogen, nitro, —NR$^a$R$^b$ and hydroxyl;
R$^2$ is C$_{1-6}$ alkyl, phenyl-C$_{1-4}$ alkyl or C$_{3-7}$ cycloalkyl-C$_{1-4}$ alkyl;
R$^7$ is C$_{1-6}$ alkyl, C$_{3-7}$ cycloalkyl, NR$^a$R$^b$, optionally substituted phenyl or phenyl C$_{1-3}$ alkyl;
X$^6$ is absent; and,
X$^1$ is O.

13. A compound according to claim 12 wherein m is one or two and the 7 and/or the 8 position(s) is(are) substituted.

14. A compound according to claim 13 wherein R$^1$ in each incidence is independently selected from the group consisting of —X$^1$(CH$_2$)$_o$COR$^5$, —NR$^6$SO$_2$R$^7$, —X$^4$(CH$_2$)$_r$NR$^a$'R$^{b'}$, —X$^5$C(=O)R$^9$, —NR$^a$R$^b$, nitro, halogen and hydroxyl.

15. A compound according to claims 14 wherein m is one, the 7-position is substituted and R$^1$ is nitro, NR$^a$R$^b$ or NR$^6$SO$_2$R$^7$.

16. The compound according to claim 1 wherein A is A-2 and R$^{10}$ is phenyl optionally substituted with one to three substituents independently selected from the group consisting of C$_{1-3}$ alkyl, C$_{1-3}$ alkoxy, C$_{1-3}$ haloalkyl, halogen, NR$^a$R$^b$, cyano and nitro.

17. The compound according to claim 16 wherein:
R$^1$ in each incidence is independently selected from the group consisting of —X$^1$(CH$_2$)$_o$COR$^5$, —NR$^6$SO$_2$R$^7$, —X$^4$(CH$_2$)$_r$NR$^a$'R$^{b'}$, —X$^5$C(=O)R$^9$, halogen and hydroxyl;
R$^2$ is C$_{1-6}$ alkyl, phenyl-C$_{1-4}$ alkyl or C$_{3-7}$ cycloalkyl-C$_{1-4}$ alkyl;
X$^1$ is O; and,
X$^6$ is absent.

18. The compound according to claim 1 wherein A is A-4.

19. The compound according to claim 18 wherein:
R$^1$ in each incidence is independently selected from the group consisting of —X$^1$(CH$_2$)$_o$COR$^5$, —NR$^6$SO$_2$R$^7$, —X$^4$(CH$_2$)$_r$NR$^a$R$^b$, —X$^5$C(=O)R$^9$, halogen and hydroxyl;
R$^2$ is C$_{1-6}$ alkyl, phenyl-C$_{1-4}$ alkyl or C$_{3-7}$ cycloalkyl-C$_{1-4}$ alkyl; and,
X$^1$ is O.

20. The compound according to claim 1 wherein A is A-5.

21. The compound according to claim 20 wherein:
R$^1$ in each incidence is independently selected from the group consisting of —X$^1$(CH$_2$)$_o$COR$^5$, —(CH$_2$)$_o$COR$^5$, —X$^1$(CH$_2$)$_o$SO$_2$R$^7$, —(CH$_2$)$_o$SO$_2$R$^7$, —NR$^6$COR$^5$, —NR$^6$SO$_2$R$^7$, —X$^4$(CH$_2$)$_r$NR$^a$'R$^{b'}$, —X$^5$C(=O)R$^9$, CONR$^a$R$^b$, —CO$_2$R$^6$, NR$^a$R$^b$, halogen, nitro, or hydroxyl;
R$^2$ is C$_{1-6}$ alkyl, optionally substituted phenyl-C$_{1-4}$ alkyl or C$_{3-7}$ cycloalkyl-C$_{1-4}$ alkyl;
R$^3$ is C$_{1-6}$ alkyl, C$_{1-6}$ alkoxy, halogen, —NR$^a$R$^b$, C$_{1-6}$ acylamino, NR$^6$SO$_2$R$^7$, cyano or nitro;
X$^6$ is absent; and,
X$^1$ is O.

22. The compound according to claim 1 wherein A is A-6.

23. The compound according to claim 1 wherein A is A-7 or A-8.

24. The compound according to claim 23 wherein:
R$^1$ in each incidence is independently selected from the group consisting of —X$^1$(CH$_2$)$_o$COR$^5$, —(CH$_2$)$_o$COR$^5$, —X$^1$(CH$_2$)$_o$SO$_2$R$^7$, —(CH$_2$)$_o$SO$_2$R$^7$, —NR$^6$SO$_2$R$^7$, —X$^4$(CH$_2$)$_r$NR$^a$'R$^{b'}$, —X$^5$C(=O)R$^9$, CONR$^a$R$^b$, —CO$_2$R$^6$, —NR$^a$R$^b$, halogen, nitro, and hydroxyl;
R$^2$ is C$_{1-6}$ alkyl, optionally substituted phenyl-C$_{1-4}$ alkyl or C$_{3-7}$ cycloalkyl-C$_{1-4}$ alkyl;
R$^7$ is C$_{1-6}$ alkyl, C$_{3-7}$ cycloalkyl, NR$^a$R$^b$, optionally substituted phenyl or phenyl C$_{1-3}$ alkyl;
X is CH;
X$^6$ is absent; and,
X$^1$ is O.

25. The compound according to claim 24 wherein R$^1$ in each incidence is independently selected from the group consisting of —X$^1$(CH$_2$)$_o$COR$^5$, —NR$^6$SO$_2$R$^7$, —X$^4$(CH$_2$)$_r$NR$^a$'R$^{b'}$, —X$^5$C(=O)R$^9$, nitro, —NR$^a$R$^b$, halogen and hydroxyl.

26. A compound according to claim 24 wherein m is one or two and the seven- and/or eight-positions is(are) substituted.

27. A compound according to claim 26 wherein R$^1$ in each incidence is independently selected from the group consisting of —X$^1$(CH$_2$)$_o$COR$^5$, —NR$^6$SO$_2$R$^7$, —X$^4$(CH$_2$)$_r$NR$^a$'R$^{b'}$, —X$^5$C(=O)R$^9$, nitro, —NR$^a$R$^b$, halogen and hydroxyl.

28. A compound of claim 26 wherein m is one and the 7-position is substituted.

29. A compound according to claim 28 wherein R$^1$ is selected from the group consisting of —X$^1$(CH$_2$)$_o$COR$^5$, —NR$^6$SO$_2$R$^7$, —X$^4$(CH$_2$)$_r$NR$^a$'R$^{b'}$, —X$^5$C(=O)R$^9$, halogen or hydroxyl, —NR$^a$R$^b$ and nitro.

30. A compound according to claim 29 wherein R$^1$ is NR$^6$SO$_2$R$^7$, nitro or NR$^a$R$^b$.

31. A compound according to claim 1 wherein the compound is selected from the group consisting of:
3-(1,1-Dioxo-1,4-dihydro-1λ$^6$-benzo[1,4]thiazin-3-yl)-4-hydroxy-1-(3-methyl-butyl)-1H-quinolin-2-one;
1-(2-Cyclopropyl-ethyl)-3-(1,1-dioxo-1,4-dihydro-1λ$^6$-benzo[1,4]thiazin-3-yl)-6-fluoro-4-hydroxy-1H-quinolin-2-one;
6-Chloro-3-(1,1-dioxo-1,4-dihydro-1λ$^6$-benzo[1,4]thiazin-3-yl)-4-hydroxy-1-(3-methyl-butyl)-1H-quinolin-2-one;
1-(2-Cyclopropyl-ethyl)-3-(1,1-dioxo-1,4-dihydro-1λ$^6$-benzo[1,4]thiazin-3-yl)-4-hydroxy-6-methyl-1H-quinolin-2-one;
1-(2-Cyclopropyl-ethyl)-3-(1,1-dioxo-1,4-dihydro-1λ$^6$-benzo[1,4]thiazin-3-yl)-4-hydroxy-6-methoxy-1H-quinolin-2-one;
6-Chloro-1-(2-cyclopropyl-ethyl)-3-(1,1-dioxo-1,4-dihydro-1λ$^6$-benzo[1,4]thiazin-3-yl)-4-hydroxy-1H-quinolin-2-one;
3-(6-Chloro-1,1-dioxo-1,4-dihydro-1λ$^6$-benzo[1,4]thiazin-3-yl)-4-hydroxy-1-(3-methyl-butyl)-1H-quinolin-2-one;
3-(1,1-Dioxo-1,4-dihydro-1λ$^6$-benzo[1,4]thiazin-3-yl)-1-(2-fluoro-benzyl)-4-hydroxy-1H-quinolin-2-one;
3-(1,1-Dioxo-1,4-dihydro-1λ$^6$-benzo[1,4]thiazin-3-yl)-1-(4-fluoro-benzyl)-4-hydroxy-1H-quinolin-2-one;
3-(1,1-Dioxo-1,4-dihydro-1λ6-benzo[1,4]thiazin-3-yl)-1-(4-fluoro-benzyl)-4-hydroxy-1H-quinolin-2-one, sodium salt;
1-(2-Cyclopropyl-ethyl)-3-(1,1-dioxo-1,4-dihydro-1λ$^6$-benzo[1,4]thiazin-3-yl)-4-hydroxy-1H-[1,8]naphthyridin-2-one;
3-(1,1-Dioxo-1,4-dihydro-1λ$^6$-benzo[1,4]thiazin-3-yl)-4-hydroxy-1-(3-methyl-butyl)-1H-[1,8]naphthyridin-2-one;

3-(1,1-Dioxo-1,4-dihydro-1λ⁶-benzo[1,4]thiazin-3-yl)-6-fluoro-4-hydroxy-1-(3-methyl-butyl)-1H-[1,8]naphthyridin-2-one;

3-(1,1-Dioxo-1,4-dihydro-1λ⁶-benzo[1,4]thiazin-3-yl)-6-fluoro-1-(4-fluoro-benzyl)-4-hydroxy-1H-quinolin-2-one;

3-(1,1-Dioxo-1,4-dihydro-1λ⁶-benzo[1,4]thiazin-3-yl)-6-fluoro-1-(4-fluoro-benzyl)-4-hydroxy-1H-quinolin-2-one, sodium salt;

3-(1,1-Dioxo-1,4-dihydro-1λ⁶-benzo[1,4]thiazin-3-yl)-1-(4-fluoro-benzyl)-4-hydroxy-6-methyl-1H-quinolin-2-one;

3-(1,1-Dioxo-1,4-dihydro-1λ⁶-benzo[1,4]thiazin-3-yl)-1-(4-fluoro-benzyl)-4-hydroxy-6-methyl-1H-quinolin-2-one, sodium salt;

1-(2-Cyclopropyl-ethyl)-6-fluoro-4-hydroxy-3-(7-nitro-1,1-dioxo-1,4-dihydro-1λ⁶-benzo[1,4]thiazin-3-yl)-1H-quinolin-2-one;

3-(6-Cyano-1,1-dioxo-1,4-dihydro-1λ⁶-benzo[1,4]thiazin-3-yl)-4-hydroxy-1-(3-methyl-butyl)-1H-quinolin-2-one;

3-(6-Aminomethyl-1,1-dioxo-1,4-dihydro-1λ⁶-benzo[1,4]thiazin-3-yl)-4-hydroxy-1-(3-methyl-butyl)-1H-quinolin-2-one;

6-Fluoro-1-(4-fluoro-benzyl)-4-hydroxy-3-(7-hydroxy-1,1-dioxo-1,4-dihydro-1λ⁶-benzo[1,4]thiazin-3-yl)-1H-quinolin-2-one;

3-(7-Benzyloxy-1,1-dioxo-1,4-dihydro-1λ⁶-benzo[1,4]thiazin-3-yl)-6-fluoro-1-(4-fluoro-benzyl)-4-hydroxy-1H-quinolin-2-one;

2-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-acetamide;

3-(7-Amino-1,1-dioxo-1,4-dihydro-1λ⁶-benzo[1,4]thiazin-3-yl)-1-(2-cyclopropyl-ethyl)-4-hydroxy-1H-quinolin-2-one;

3-(7-Amino-1,1-dioxo-1,4-dihydro-1λ⁶-benzo[1,4]thiazin-3-yl)-6-fluoro-1-(4-fluoro-benzyl)-4-hydroxy-1H-quinolin-2-one;

N-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-acetamide;

N-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-methanesulfonamide, sodium salt;

1-(3,4-Difluoro-benzyl)-3-(1,1-dioxo-1,4-dihydro-1λ⁶-benzo[1,4]thiazin-3-yl)-6-fluoro-4-hydroxy-1H-quinolin-2-one;

1-(3,4-Difluoro-benzyl)-3-(1,1-dioxo-1,4-dihydro-1λ⁶-benzo[1,4]thiazin-3-yl)-6-fluoro-4-hydroxy-1H-quinolin-2-one, sodium salt;

3-(1,1-Dioxo-1,4-dihydro-1λ⁶-benzo[1,4]thiazin-3-yl)-6-fluoro-1-(4-fluoro-3-methyl-benzyl)-4-hydroxy-1H-quinolin-2-one;

3-(1,1-Dioxo-1,4-dihydro-1λ⁶-benzo[1,4]thiazin-3-yl)-6-fluoro-1-(4-fluoro-3-methyl-benzyl)-4-hydroxy-1H-quinolin-2-one, sodium salt;

3-[3-(1,1-Dioxo-1,4-dihydro-1λ⁶-benzo[1,4]thiazin-3-yl)-6-fluoro-4-hydroxy-2-oxo-2H-quinolin-1-ylmethyl]-benzonitrile;

3-[3-(1,1-Dioxo-1,4-dihydro-1λ⁶-benzo[1,4]thiazin-3-yl)-6-fluoro-4-hydroxy-2-oxo-2H-quinolin-1-ylmethyl]-benzonitrile, sodium salt;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-methanesulfonamide;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-methanesulfonamide, sodium salt;

Propane-1-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

Propane-1-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide, sodium salt;

6-Fluoro-1-(4-fluoro-benzyl)-4-hydroxy-3-(7-methoxy-1,1-dioxo-1,4-dihydro-1λ⁶-benzo[1,4]thiazin-3-yl)-1H-quinolin-2-one;

{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-acetic acid methyl ester;

Ethanesulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

Cyclopropanesulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

2-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-N,N-dimethyl-acetamide;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-N-methyl-methanesulfonamide;

3,5-Dimethyl-isoxazole-4-sulfonic acid {3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-amide;

N-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-benzenesulfonamide;

1-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-3-methyl-urea;

3-{3-[1-(2-Cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yloxy}-propionamide;

N-{3-[1-(2-cyclopropyl-ethyl)-6-fluoro-4-hydroxy-2-oxo-1,2-dihydro-quinolin-3-yl]-1,1-dioxo-1,4-dihydro-1λ⁶-benzo[1,4]thiazin-7-yl}-sulfamide (I-40);

Pyrrolidine-1-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide (I-65);

2-{3-[6-Fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yloxy}-N-methyl-acetamide;

Ethanesulfonic acid {3-[6-fluoro-1-(4-fluoro-benzyl)-4-hydroxy-2-oxo-1,2-dihydro-quinolin-3-yl]-1,1-dioxo-1,4-dihydro-1λ⁶-benzo[1,4]thiazin-7-yl}-amide;

N-[3-(4-Hydroxy-1-methyl-2-oxo-1,2-dihydro-quinolin-3-yl)-1,1-dioxo-1,4-dihydro-1λ⁶-benzo[1,4]thiazin-7-yl]-methanesulfonamide;

N-{3-[1-(4-Fluoro-benzyl)-4-hydroxy-6-methyl-2-oxo-1,2-dihydro-quinolin-3-yl]-1,1-dioxo-1,4-dihydro-1λ⁶-benzo[1,4]thiazin-7-yl}-methanesulfonamide;

Propane-1-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-amide;

N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-N-methyl-methanesulfonamide;

N-{3-[6-Fluoro-1-(4-fluoro-3-methyl-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-{3-[1-(3-Chloro-4-fluoro-benzyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-[3-(6-Fluoro-4-hydroxy-2-oxo-1-pyridin-3-ylmethyl-1,2-dihydro-quinolin-3-yl)-1,1-dioxo-1,4-dihydro-1λ$^6$-benzo[1,4]thiazin-7-yl]-methanesulfonamide;

N-{3-(1-Cyclohexylmethyl-6-fluoro-4-hydroxy-2-oxo-1,2-dihydro-quinolin-3-yl)-1,1-dioxo-1,4-dihydro-1λ$^6$-benzo[1,4]thiazin-7-yl}-methanesulfonamide;

N-{3-[6-Fluoro-4-hydroxy-1-(3-methyl-butyl)-2-oxo-1,2-dihydro-quinolin-3-yl]-1,1-dioxo-1,4-dihydro-1λ$^6$-benzo[1,4]thiazin-7-yl}-methanesulfonamide;

Cyclopropanesulfonic acid {3-[6-fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-amide;

N-{3-[1-(3,4-Difluoro-benzyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-{3-[6-Fluoro-1-(4-fluoro-3-trifluoromethyl-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-{3-[6-Fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-C-phenyl-methanesulfonamide;

2-Oxo-oxazolidine-3-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-amide;

N-{3-[1-(4-Fluoro-benzyl)-4-hydroxy-6-methoxy-2-oxo-1,2-dihydro-quinolin-3-yl]-1,1-dioxo-1,4-dihydro-1λ$^6$-benzo[1,4]thiazin-7-yl}-methanesulfonamide;

N-{3-[6-Chloro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

Propane-2-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-amide;

Butane-1-sulfonic acid {3-[6-fluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-amide;

N-{3-[1-(4-Fluoro-benzyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-sulfamide (I-64);

1-{3-[1-(4-Fluoro-benzyl)-6-fluoro-4-hydroxy-2-oxo-1,2-dihydro-quinolin-3-yl]-1,1-dioxo-1,4-dihydro-1λ$^6$-benzo[1,4]thiazin-7-yl}-3,3-dimethyl-sulfamide (I-62);

N-{3-[6,7-Difluoro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

N-[3-(6-Fluoro-4-hydroxy-2-oxo-1-pyridin-4-ylmethyl-1,2-dihydro-quinolin-3-yl)-1,1-dioxo-1,4-dihydro-1λ$^6$-benzo[1,4]thiazin-7-yl]-methanesulfonamide; compound with trifluoro-acetic acid;

N-{3-[7-Chloro-1-(4-fluoro-benzyl)-4-hydroxy-2-oxo-1,2-dihydro-quinolin-3-yl]-1,1-dioxo-1,4-dihydro-1λ$^6$-benzo[1,4]thiazin-7-yl}-methanesulfonamide;

6-Fluoro-1-(4-fluoro-benzyl)-4-hydroxy-3-(7-methoxymethyl-1,1-dioxo-1,4-dihydro-1λ$^6$benzo[1,4]thiazin-3-yl)-1H-quinolin-2-one;

5-(7-Amino-1,1-dioxo-1,4-dihydro-1λ$^6$-benzo[1,4]thiazin-3-yl)-7-(4-fluoro-benzyl)-4-hydroxy-2-methyl-7H-thieno[2,3-b]pyridin-6-one;

N-{3-[7-(4-Fluoro-benzyl)-4-hydroxy-2-methyl-6-oxo-6,7-dihydro-thieno[2,3-b]pyridin-5-yl]-1,1-dioxo-1,4-dihydro-1λ$^6$-benzo[1,4]thiazin-7-yl}-methanesulfonamide;

N-{3-[7-(4-Fluoro-benzyl)-4-hydroxy-6-oxo-6,7-dihydro-thieno[2,3-b]pyridin-5-yl]-1,1-dioxo-1,4-dihydro-1λ$^6$-benzo[1,4]thiazin-7-yl}-methanesulfonamide;

(S)-5-tert-Butyl-3-(1,1-dioxo-1,4-dihydro-1λ$^6$-benzo[1,4]thiazin-3-yl)-4-hydroxy-1-(3-methyl-butyl)-1,5-dihydro-pyrrol-2-one;

(S)-5-Cyclohexyl-3-(1,1-dioxo-1,4-dihydro-1λ$^6$-benzo[1,4]thiazin-3-yl)-4-hydroxy-1-(3-methyl-butyl)-1,5-dihydro-pyrrol-2-one;

(S)-5-((S)-sec-Butyl)-3-(1,1-dioxo-1,4-dihydro-1λ$^6$-benzo[1,4]thiazin-3-yl)-4-hydroxy-1-(3-methyl-butyl)-1,5-dihydro-pyrrol-2-one;

(S)-1-Benzyl-5-((S)-sec-butyl)-3-(1,1-dioxo-1,4-dihydro-1λ$^6$-benzo[1,4]thiazin-3-yl)-4-hydroxy-1,5-dihydro-pyrrol-2-one;

(S)-3-(1,1-Dioxo-1,4-dihydro-1λ$^6$-benzo[1,4]thiazin-3-yl)-1-(4-fluoro-benzyl)-4-hydroxy-5-isobutyl-1,5-dihydro-pyrrol-2-one;

(S)-5-Cyclohexyl-3-(1,1-dioxo-1,4-dihydro-1λ$^6$-benzo[1,4]thiazin-3-yl)-1-(4-fluoro-benzyl)-4-hydroxy-1,5-dihydro-pyrrol-2-one;

(S)-5-Cyclohexyl-3-(1,1-dioxo-1,4-dihydro-1λ$^6$-benzo[1,4]thiazin-3-yl)-1-(4-fluoro-benzyl)-4-hydroxy-1,5-dihydro-pyrrol-2-one; sodium salt;

N-{3-[(S)-5-tert-Butyl-1-(4-fluoro-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide;

N-{3-[(S)-5-tert-Butyl-1-(4-fluoro-3-methyl-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide;

N-{3-[(S)-5-tert-Butyl-1-(4-fluoro-3-methoxy-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfohydro-1H-pyrrol-3-yl]-1,1-dioxo-1,4-dihydro-1λ$^6$-benzo[1,4]thiazin-7-yl}-methanesulfonamide;

(S)-5-tert-Butyl-1-(4-fluoro-benzyl)-4-hydroxy-3-(7-nitro-1,1-dioxo-1,4-dihydro-1λ$^6$-benzo[1,4]thiazin-3-yl)-1,5-dihydro-pyrrol-2-one;

(S)-3-(7-Amino-1,1-dioxo-1,4-dihydro-1λ$^6$-benzo[1,4]thiazin-3-yl)-5-tert-butyl-1-(4-fluoro-benzyl)-4-hydroxy-1,5-dihydro-pyrrol-2-one;

N-{3-[(S)-5-tert-Butyl-1-(4-fluoro-benzyl)-4-hydroxy-2-oxo-2,5-dihydro-1H-pyrrol-3-yl]-1,1-dioxo-1,4-dihydro-1λ$^6$-benzo[1,4]thiazin-7-yl}-sulfamide (II-14);

(S)-3-(7-Amino-1,1-dioxo-1,4-dihydro-1λ$^6$-benzo[1,4]thiazin-3-yl)-5-tert-butyl-1-(2-cyclopropyl-ethyl)-4-hydroxy-1,5-dihydro-pyrrol-2-one;

N-{3-[(S)-5-tert-Butyl-1-(2-cyclopropyl-ethyl)-4-hydroxy-2-oxo-2,5-dihydro-1H-pyrrol-3-yl]-1,1-dioxo-1,4-dihydro-1λ$^6$-benzo[1,4]thiazin-7-yl}-methanesulfonamide;

1-tert-Butyl-4-(1,1-dioxo-1,4-dihydro-1λ⁶-benzo[1,4]thiazin-3-yl)-2-(4-fluoro-benzyl)-5-hydroxy-1,2-dihydro-pyrazol-3-one;

N-{3-[4-(4-fluoro-benzyl)-7-hydroxy-5-oxo-4,5-dihydro-thieno[3,2-b]pyridin-6-yl]-1,1-dioxo-1,4-dihydro-1λ6-benzo[1,4]thiazin-7-yl}-methanesulfonamide; and, N-{3-[2-Ethyl-7-(4-fluoro-benzyl)-4-hydroxy-6-oxo-6,7-dihydro-thieno[2,3-b]pyridin-5-yl]-1,1-dioxo-1,4-dihydro-1λ6-benzo[1,4]thiazin-7-yl}-methanesulfonamide.

32. A method for treating a disease caused by Hepatitis C Virus (HCV) infection comprising administering to a patient in need thereof, a therapeutically effective quantity of a compound according to claim 1.

33. The method of claim 32 wherein A in the compound of formula I is A-1, A-7 or A-8.

34. The method of claim 33 wherein A in the compound of formula I is A-3.

35. The method of claim 34 further comprising administering at least one immune system modulator which immune system modulator is an interferon, interleukin, tumor necrosis factor or colony stimulating factor and/or at least one antiviral agent which antiviral agent is HCV protease inhibitor, another HCV polymerase inhibitor, a HCV helicase, HCV primase inhibitor or a HCV fusion inhibitor or ribavirin.

36. The method of claim 35 wherein the immune system modulator is an interferon-α2a or interferon-α2b or an interferon-α2a or interferon-α2b covalently derivatized with polyethyleneglycol (PEG).

37. The method of claim 35 comprising administering ribavirin, an HCV protease inhibitor, or another HCV polymerase inhibitor.

38. The method of claim 35 wherein the antiviral compound is selected from the group consisting of an a HCV helicase, HCV primase inhibitor or a HCV fusion inhibitor.

39. A pharmaceutical composition comprising a therapeutically effective quantity of a compound according to claim 1 admixed with at least one pharmaceutically acceptable carrier, diluent or excipient.

40. A process for preparing a compound according to claim 1 wherein A is A-1, A-2 or A-7 comprising the steps of:
(i) contacting an optionally substituted (1,1-dioxo-1,4-dihydro-1λ⁶-benzo[1,4]thiazin-3-yl)-acetic acid alkyl ester with a base whose $pK_b$ is sufficiently great to abstract a proton under conditions sufficient to convert V to the corresponding conjugate base Va;

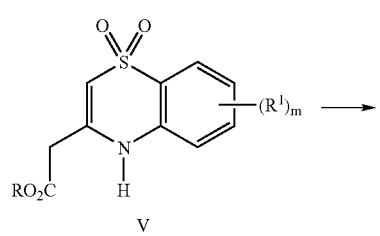

(ii) contacting Va with an optionally ring fused 3-substituted-3H-[1,3]-oxazine-2,6-dione VI under conditions sufficient to result in condensation with Va and cyclization to afford VII

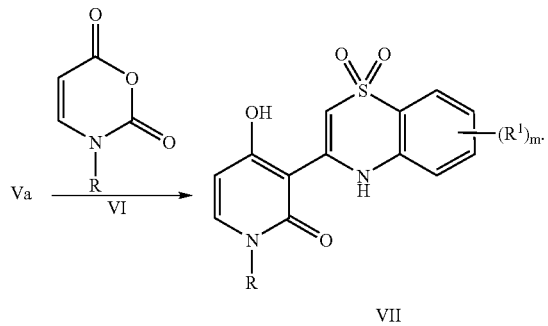

41. A process for preparing a compound according to claim 1 wherein A is A-3 comprising the steps of:
(i) contacting an optionally substituted (1,1-dioxo-1,4-dihydro-1λ⁶-benzo[1,4]thiazin-3-yl)-acetic acid derivative V wherein R is OH, Cl, O—$C_{1-6}$ alkyl with an amino acid ester VIII wherein R" is $C_{1-6}$ alkyl, and $R^1$, $R^2$ and $R^4$ are as defined in claim 1 under conditions sufficient to promote amide bond formation;

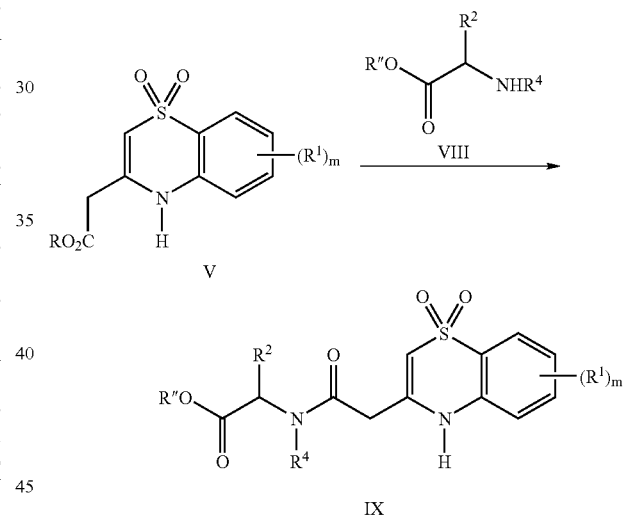

(ii) contacting IX with a base whose $pK_b$ is sufficient to abstract a proton from the methylene linked to the thiazine ring under conditions sufficient to convert IX to the corresponding conjugate base and induce intra-molecular cyclization to produce X

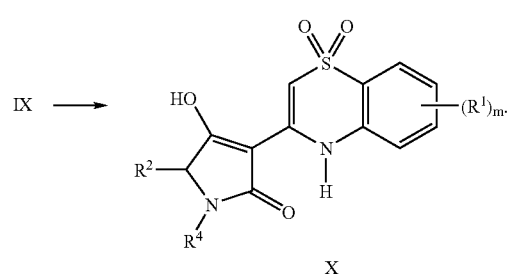

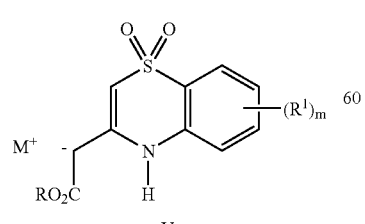

* * * * *